(12) United States Patent
Choi et al.

(10) Patent No.: US 9,966,538 B2
(45) Date of Patent: May 8, 2018

(54) COMPOUND, LIGHT-EMITTING ELEMENT AND ELECTRONIC DEVICE COMPRISING SAME

(71) Applicant: LMS Co., Ltd., Pyeongtaek-si (KR)

(72) Inventors: Jeong Og Choi, Seoul (KR); Joon Ho Jung, Hwaseong-si (KR); Oh Kwan Kwon, Anyang-si (KR)

(73) Assignee: LMS CO., LTD., Pyeongtaek-si (KR)

( * ) Notice: Subject to any disclaimer, the term of this patent is extended or adjusted under 35 U.S.C. 154(b) by 302 days.

(21) Appl. No.: 14/441,034

(22) PCT Filed: Nov. 7, 2013

(86) PCT No.: PCT/KR2013/010062
§ 371 (c)(1),
(2) Date: Sep. 30, 2015

(87) PCT Pub. No.: WO2014/073875
PCT Pub. Date: May 15, 2014

(65) Prior Publication Data
US 2016/0181544 A1    Jun. 23, 2016

(30) Foreign Application Priority Data

Nov. 7, 2012 (KR) .................. 10-2012-0125672

(51) Int. Cl.
*H01L 51/00* (2006.01)
*C09K 11/06* (2006.01)
(Continued)

(52) U.S. Cl.
CPC ........ *H01L 51/0071* (2013.01); *C07D 277/66* (2013.01); *C07D 417/04* (2013.01);
(Continued)

(58) Field of Classification Search
CPC combination set(s) only.
See application file for complete search history.

(56) References Cited

U.S. PATENT DOCUMENTS

2005/0274961 A1*  12/2005  Iou ................... H01L 51/5088
                                                      257/82
2006/0162099 A1*  7/2006  Lim ........................ A61K 8/49
                                                       8/405
(Continued)

FOREIGN PATENT DOCUMENTS

JP    2000222771 A    8/2000
KR    1020110134581 A    12/2011

OTHER PUBLICATIONS

Shi et al.; "Synthesis, photophysical and electrochemical properties of a carbazole dimer-based derivative with benzothiazole units"; Spectrochimica Acta Part A; Jul. 31, 2012; pp. 19-25, vol. 93.
(Continued)

*Primary Examiner* — Jennifer A Chriss
*Assistant Examiner* — Sean M DeGuire
(74) *Attorney, Agent, or Firm* — Polsinelli PC

(57) ABSTRACT

A novel compound for improving the power efficiency and the lifespan of a light-emitting element, and a light-emitting element and an electronic device including the same are provided. And the new compound may provide excellent light-emitting efficiency and extended lifespan, and may improve thermal stability (heat resistance) for the electronic device.

14 Claims, 3 Drawing Sheets

(51) Int. Cl.
*C07D 417/14* (2006.01)
*H05B 33/10* (2006.01)
*C07D 277/66* (2006.01)
*C07D 417/04* (2006.01)
*C09K 11/02* (2006.01)
*H01L 51/50* (2006.01)

(52) U.S. Cl.
CPC .......... *C07D 417/14* (2013.01); *C09K 11/025* (2013.01); *C09K 11/06* (2013.01); *H01L 51/006* (2013.01); *H01L 51/0059* (2013.01); *H01L 51/0067* (2013.01); *H01L 51/0072* (2013.01); *H01L 51/0073* (2013.01); *H01L 51/0074* (2013.01); *H01L 51/0085* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1037* (2013.01); *C09K 2211/1044* (2013.01); *C09K 2211/1088* (2013.01); *C09K 2211/1092* (2013.01); *C09K 2211/185* (2013.01); *H01L 51/0061* (2013.01); *H01L 51/506* (2013.01); *H01L 51/5016* (2013.01); *H01L 51/5064* (2013.01); *H01L 51/5076* (2013.01); *H01L 51/5096* (2013.01); *H01L 2251/308* (2013.01); *H01L 2251/558* (2013.01)

(56) References Cited

U.S. PATENT DOCUMENTS

2009/0197862 A1     8/2009   Steinig et al.
2010/0326526 A1*   12/2010   Zheng ................. C07D 235/18
                                                              136/263

OTHER PUBLICATIONS

Ying; "3, 6-Disubstituted carbazole chroMophores containing thiazole and benzothiazole units: Synthesis, characterization and first-order hyperpolarizabilities"; Dyes and Pigments; 2008; pp. 277-281; vol. 76.

* cited by examiner

[Fig.1]
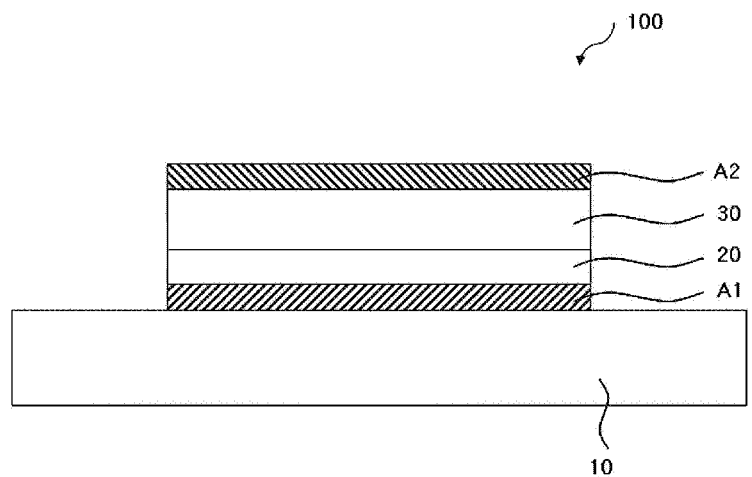
[Fig.2]
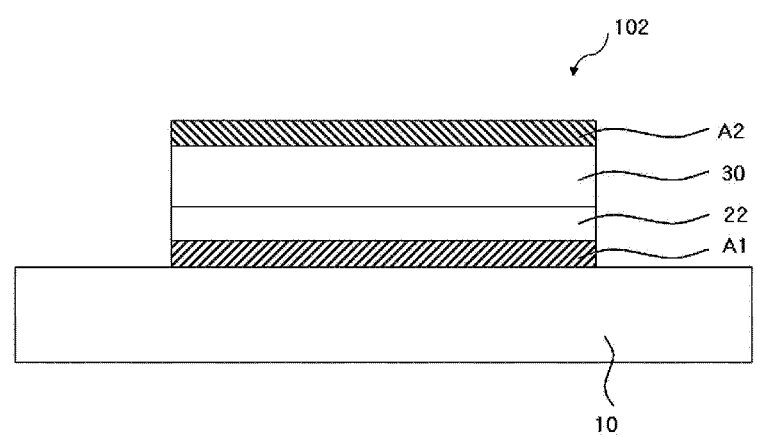

[Fig.3]
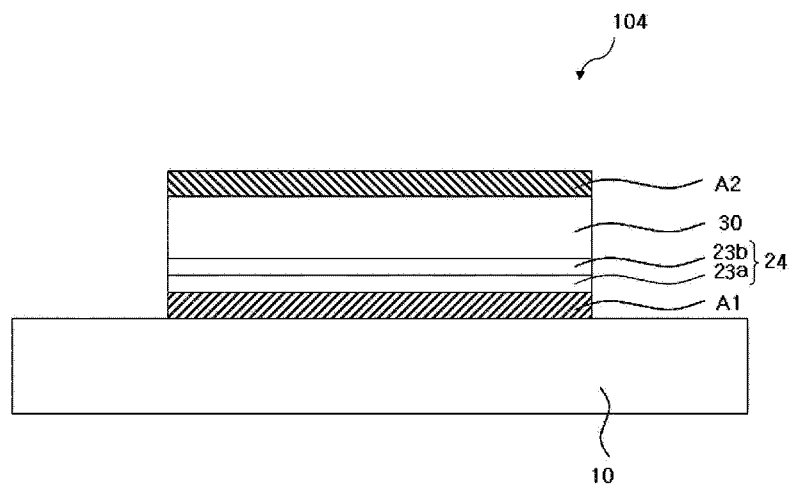
[Fig.4]
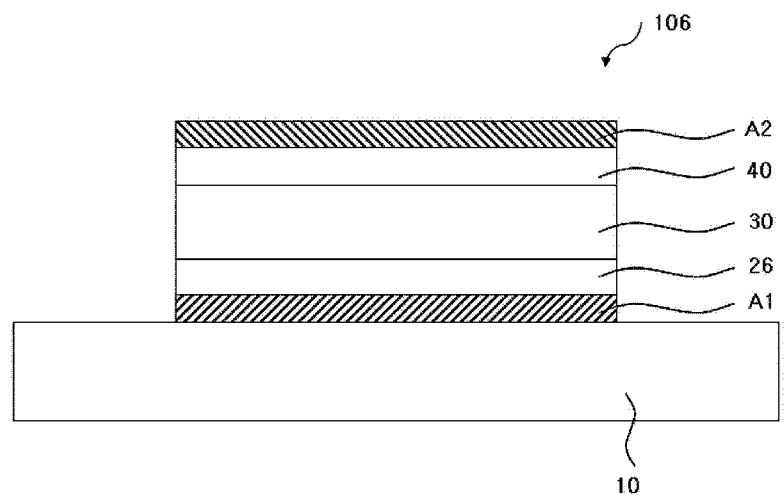

[Fig.5]
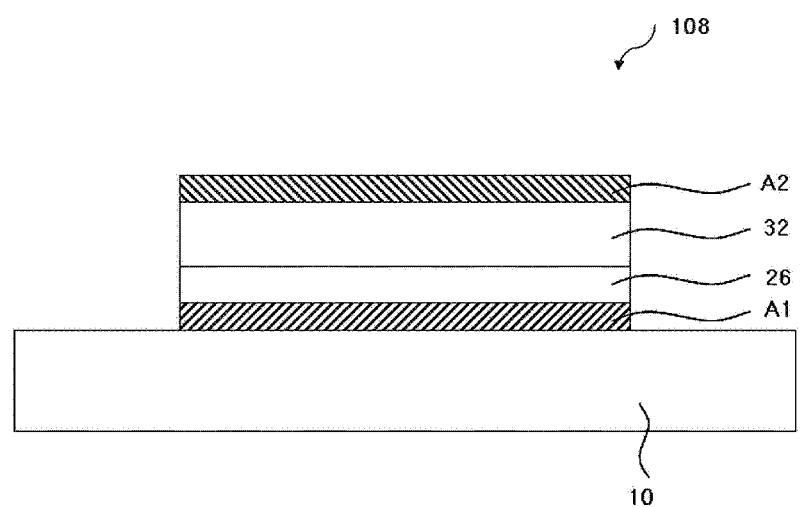

COMPOUND, LIGHT-EMITTING ELEMENT AND ELECTRONIC DEVICE COMPRISING SAME

CROSS-REFERENCE TO RELATED APPLICATIONS

This application is the United States national phase of International Application No. PCT/KR2013/010062 filed Nov. 7, 2013, and claims priority to Korean Patent Application No. 10-2012-0125672 filed Nov. 7, 2012, the disclosures of which are hereby incorporated in their entirety by reference.

BACKGROUND

Field of the Invention

The present invention relates to a novel compound, and a light-emitting element and an electronic device including the same, and more particularly, to a compound for an organic light-emitting element, and a light-emitting element and an electronic device including the same.

Background Art

In general, a light-emitting element includes two electrodes facing each other and a light-emitting layer including a light-emitting compound interposed between the electrodes. When current flows between the electrodes, the light-emitting compound produces light. The light-emitting element may further include a hole transporting layer disposed between an anode and the light-emitting layer, or an electron transporting layer disposed between a cathode and the light-emitting layer. The hole transporting layer or the electron transporting layer may stabilize the interface between an electrode and a light-emitting layer, and minimize an energy barrier between the electrode and the light-emitting layer.

A display device using the light-emitting element does not need a separate light source device, and thus may decrease the weight, size or thickness of the display device. Further, the display device using the light-emitting element has advantages in that the viewing angle, the contrast ratio, the color reproducibility, and the like are excellent and power consumption is low as compared to a display device using a backlight and a liquid crystal.

In order to maximize the advantage of the light-emitting element, it is preferred that materials used for manufacturing the light-emitting element have a chemically or electrically stable state, and a suitable compound is selected according to the function of a thin film which constitutes the light-emitting element, such as a light-emitting layer, a hole transporting layer, and a charge transporting layer. However, the light-emitting element still has problems in that the lifespan for light emission is short, the power efficiency is low, and thermal stability (heat resistance) is low. In order to solve these problems, various compounds have been developed as a material for the light-emitting element, but there is a limitation in manufacturing a light-emitting element which satisfies all in respect to the lifespan of light emission, power efficiency, and thermal stability.

SUMMARY OF THE INVENTION

Technical Problem

Thus, a technical problem of the present invention has been contrived in view of these circumstances, and an object of the present invention is to provide a novel compound for enhancing the power efficiency and lifespan of a light-emitting element.

Another object of the present invention is to provide a light-emitting element including the compound.

Still another object of the present invention is to provide an electronic device including the light-emitting element.

Technical Solution

A compound according to an exemplary embodiment for realizing the object of the present invention is represented by the following Formula 1.

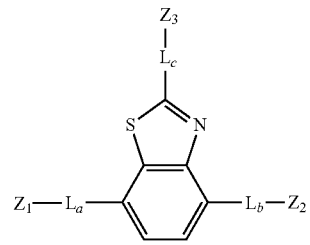

<Formula 1>

In Formula 1, $Z_1$, $Z_2$, and $Z_3$ each independently represent an aryl group having 6 to 60 carbon atoms, or any one structure of the following Formulae 2 to 6,

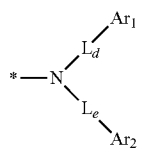

<Formula 2>

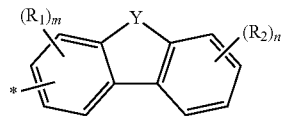

<Formula 3>

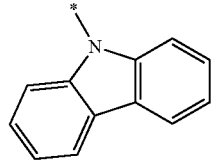

<Formula 4>

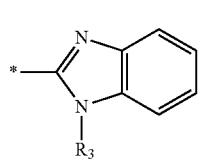

<Formula 5>

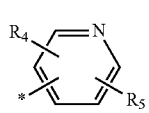

<Formula 6>

Y represents S, O, or N-$L_f$-$Ar_3$, $L_a$, $L_b$, $L_c$, $L_d$, $L_e$, and $L_f$ each independently represent *-$L_1$-$L_2$-$L_3$-$L_4$-*, $L_1$, $L_2$, $L_3$, and $L_4$ each independently represent a single bond, —O—, —S—, a linear or branched alkylene group (—$(CH_2)_j$—, here, j is an integer of 1 to 60) having 1 to 60 carbon atoms, an arylene group having 6 to 60 carbon atoms, a heteroarylene group having 2 to 60 carbon atoms, an alkenylene group having 2 to 60 carbon atoms, an alkynylene group having 2 to 60 carbon atoms, a cycloalkylene group having 3 to 60 carbon atoms, a heterocycloalkylene group 2 to 60 carbon atoms, an adamantylene group, or a bicycloalkylene group having 7 to 60 carbon atoms, $Ar_1$, $Ar_2$, and $Ar_3$ each independently represent hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, an alkenyl group having 2 to 60 carbon atoms, or an alkynyl group having 2 to 60 carbon atoms, $R_1$ and $R_2$ each independently represent an aryl group having 6 to 60 carbon atoms, a heteroaryl group having 2 to 60 carbon atoms, an alkenyl group having 2 to 60 carbon atoms, or an alkynyl group having 2 to 60 carbon atoms, $R_3$, $R_4$, and $R_5$ each independently represent an alkyl group having 1 to 3 carbon atoms, or an aryl group having 6 to 30 carbon atoms, m and n each independently represent an integer of 0 to 3, and the hydrogen atoms of $Z_1$, $Z_2$, $Z_3$, $L_a$, $L_b$, and $L_c$ of Formula 1 are each independently unsubstituted or substituted with an alkyl group having 1 to 8 carbon atoms, an alkoxy group having 1 to 8 carbon atoms, a halogen group, a cyano group, or a trimethylsilyl group.

Further, the present invention may include a light-emitting element including the compound represented by Formula 1.

In an exemplary embodiment, the light-emitting element may include: a first electrode; a second electrode; a light-emitting layer disposed between the first electrode and the second electrode; and a hole transporting layer disposed between the first electrode and the light-emitting layer, and the hole transporting layer may include the hole transport compound represented by Formula 1.

In an exemplary embodiment, the light-emitting element may include: a first electrode; a second electrode; a light-emitting layer disposed between the first electrode and the second electrode; and an electron transporting layer disposed between the second electrode and the light-emitting layer, and the electron transporting layer may include the electron transport compound represented by Formula 1.

In an exemplary embodiment, the light-emitting element may include: a first electrode; a second electrode; and a light-emitting layer disposed between the first electrode and the second electrode, and the light-emitting layer may include the light-emitting compound represented by Formula 1.

In addition, the present invention provides an electronic device including the light-emitting element.

Effect of the Invention

According to the novel compound, the light-emitting element and the electronic device including the same, a light-emitting element to which the novel compound of the present invention is applied may provide excellent light-emitting efficiency and extended lifespan, and may enhance thermal stability (heat resistance).

BRIEF DESCRIPTION OF DRAWINGS

FIG. 1 is a cross-sectional view for describing a light-emitting element according to an exemplary embodiment of the present invention.

FIG. 2 is a cross-sectional view for describing a light-emitting element according to another exemplary embodiment of the present invention.

FIG. 3 is a cross-sectional view for describing a light-emitting element according to still another exemplary embodiment of the present invention.

FIG. 4 is a cross-sectional view for describing a light-emitting element according to yet another exemplary embodiment of the present invention.

FIG. 5 is a cross-sectional view for describing a light-emitting element according to still yet another exemplary embodiment of the present invention.

DETAILED DESCRIPTION OF THE INVENTION

Hereinafter, a novel compound according to the present invention will be first described, and a light-emitting element including the compound will be described in more detail with reference to the accompanying drawings.

The compound according to the present invention is represented by the following Formula 1.

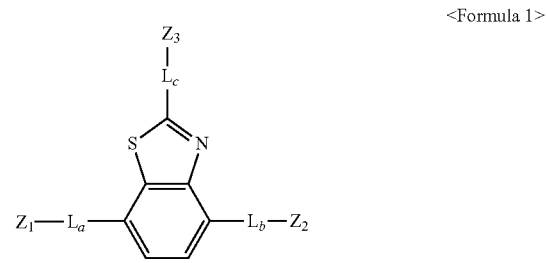

<Formula 1>

In Formula 1, $Z_1$, $Z_2$, and $Z_3$ each independently represent any one structure of the following Formulae 2 to 6,

<Formula 2>

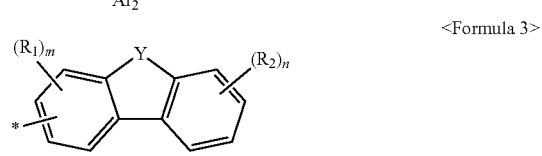

<Formula 3>

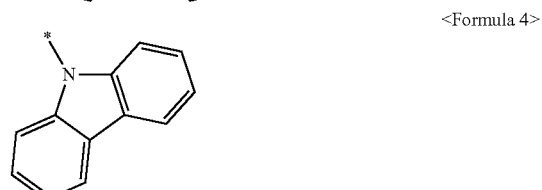

<Formula 4>

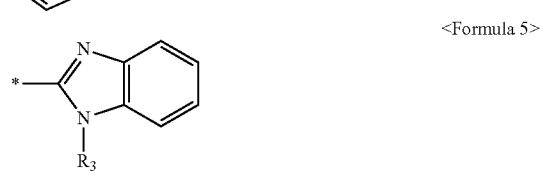

<Formula 5>

-continued

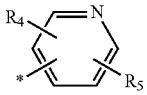
<Formula 6>

Y represents S, O, or N-L$_f$-Ar$_3$,

L$_a$, L$_b$, L$_c$, L$_d$, L$_e$, and L$_f$ each independently represent *-L$_1$-L$_2$-L$_3$-L$_4$-*, L$_1$, L$_2$, L$_3$, and L$_4$ each independently represent a single bond, —O—, —S—, a linear or branched alkylene group (—(CH$_2$)$_j$—, here, j is an integer of 1 to 60) having 1 to 60 carbon atoms, an arylene group having 6 to 60 carbon atoms, a heteroarylene group having 2 to 60 carbon atoms, an alkenylene group having 2 to 60 carbon atoms, an alkynylene group having 2 to 60 carbon atoms, a cycloalkylene group having 3 to 60 carbon atoms, a heterocycloalkylene group 2 to 60 carbon atoms, an adamantylene group, or a bicycloalkylene group having 7 to 60 carbon atoms, Ar$_1$, Ar$_2$, and Ar$_3$ each independently represent hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, an alkenyl group having 2 to 60 carbon atoms, or an alkynyl group having 2 to 60 carbon atoms, R$_1$ and R$_2$ each independently represent an aryl group having 6 to 60 carbon atoms, a heteroaryl group having 2 to 60 carbon atoms, an alkenyl group having 2 to 60 carbon atoms, or an alkynyl group having 2 to 60 carbon atoms, R$_3$, R$_4$, and R$_5$ each independently represent an alkyl group having 1 to 3 carbon atoms, or an aryl group having 6 to 30 carbon atoms, m and n each independently represent an integer of 0 to 3, and the hydrogen atoms of Z$_1$, Z$_2$, Z$_3$, L$_a$, L$_b$, and L$_c$ of Formula 1 are each independently unsubstituted or substituted with an alkyl group having 1 to 8 carbon atoms, an alkoxy group having 1 to 8 carbon atoms, a halogen group, a cyano group, or a trimethylsilyl group.

In the present invention, "an aryl group" is defined as a monovalent substituent derived from an aromatic hydrocarbon.

Specific examples of the aryl group include a phenyl group, a naphthyl group, an anthracenyl group, a phenanthryl group, a naphthacenyl group, a pyrenyl group, a tolyl group, a biphenylyl group, a terphenylyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

"A heteroaryl group" represents "an aromatic heterocyclic ring" or "a heterocyclic" derived from a monocyclic or fused ring. The heteroaryl group may include at least one of nitrogen (N), sulfur (S), oxygen (O), phosphorus (P), selenium (Se), and silicon (Si) as a heteroatom.

Specific examples of the heteroaryl group include: a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolyl group, a quinolizinyl group, a phthalazinyl group, a naphthyridinyl group, a quinoxalinyl group, a quinazolinyl group, a cinnolinyl group, a pteridinyl group, an imidazotriazinyl group, a pyrazinopyridazinyl group, an acridinyl group, a phenanthridinyl group, a carbazolyl group, a carbazolinyl group, a pyrimidinyl group, a phenanthrolinyl group, a phenazinyl group, an imidazopyridinyl group, an imidazopyrimidinyl group, a pyrazolopyridinyl group, and the like; a sulfur-containing heteroaryl group including a thienyl group, a benzothienyl group, a dibenzothienyl group, and the like; an oxygen-containing heteroaryl group including a furyl group, a pyranyl group, a cyclopentapyranyl group, a benzofuranyl group, an isobenzofuranyl group, a dibenzofuranyl group, and the like; and the like. Furthermore, specific examples of the heteroaryl group include compounds including at least two heteroatoms, such as a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, a benzoxazolyl group, an oxadiazolyl group, a pyrazoloxazolyl group, an imidazothiazolyl group, a thienofuranyl group, a furopyrrolyl group, and a pyridoxazinyl group.

The "alkyl group" is defined as a functional group derived from a linear or branched, saturated hydrocarbon.

Specific examples of the alkyl group include a methyl group, an ethyl group, an n-propyl group, an iso-propyl group, an n-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

Further, "an arylene group" may mean a divalent substituent derived from the aryl group described above.

In addition, "a heteroarylene group" may mean a divalent substituent derived from the heteroaryl group described above.

In an exemplary embodiment, the novel compound according to the present invention may be a compound in which Z$_1$ and Z$_2$ each independently have the structure of Formula 2.

For example, Z$_3$ in Formula 1 may be selected from the structures of the following Table 1.

TABLE 1

| No. | Substituent structure |
|---|---|
| 1 | *–phenyl |
| 2 | *–biphenyl |
| 3 | *–N(phenyl)$_2$ |

TABLE 1-continued

| No. | Substituent structure |
|---|---|
| 4 | 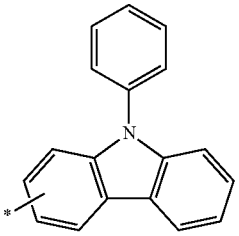 |
| 5 | 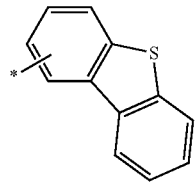 |
| 6 | 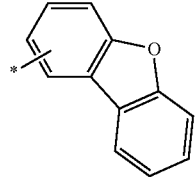 |
| 7 | 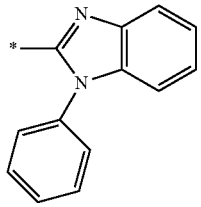 [SMILES: *c1nc2ccccc2n1-c1ccccc1] |
| 8 | 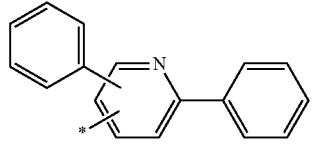 |
| 9 | 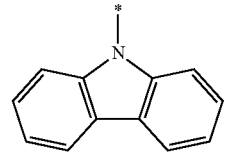 [SMILES: *n1c2ccccc2c2ccccc21] |

In this case, $Z_1$ and $Z_2$ in Formula 1 may be each independently selected from the structures of the following Table 2.

TABLE 2

| No. | Substituent structure |
|---|---|
| 1 | 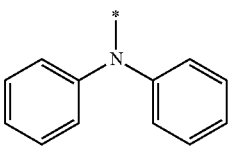 |
| 2 | 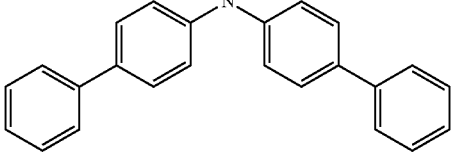 |

Furthermore, $L_a$, $L_b$, and $L_c$ in Formula 1 may be each independently selected from a single bond or the structures of the following Table 3.

TABLE 3

| No. | Substituent structure |
|---|---|
| 1 | 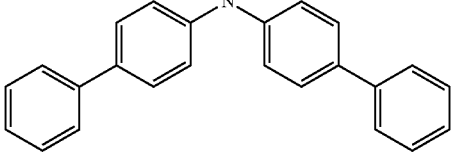 |
| 2 |  |

For example, Substituent No. 4 in Table 1 may be specifically represented by the following Formula 1-4a or the following Formula 1-4b.

<Formula 1-4a>

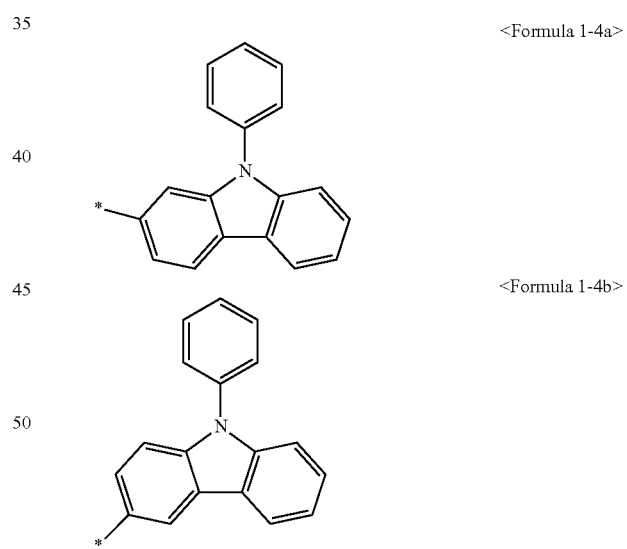

<Formula 1-4b>

Substituent No. 5 in Table 1 may be represented by the following Formula 1-5a or the following Formula 1-5b.

<Formula 1-5a>

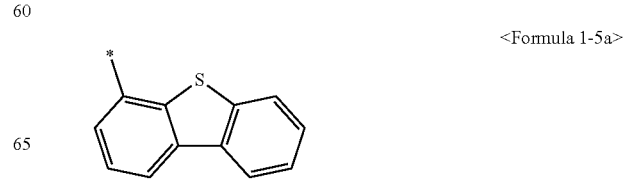

-continued

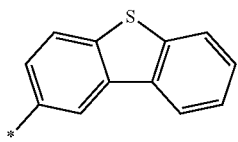
<Formula 1-5b>

Substituent No. 6 in Table 1 may be represented by the following Formula 1-6a or the following Formula 1-6b.

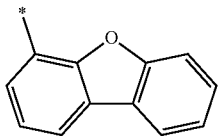
<Formula 1-6a>

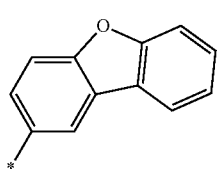
<Formula 1-6b>

Further, Substituent No. 8 in Table 1 may be represented by the following Formula 1-8a or the following Formula 1-8b.

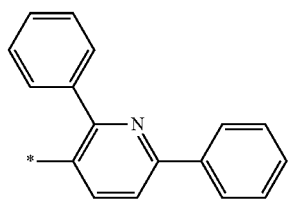
<Formula 1-8a>

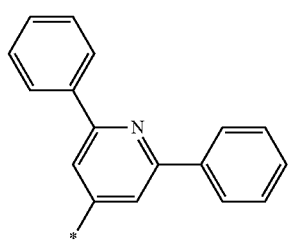
<Formula 1-8b>

Hereinafter, since substituents represented by Nos. 4 to 6 and 8 in Table 1 are represented to be substantially the same as those described above, respectively, the overlapping specific description thereof will be omitted.

More specifically, the compound represented by Formula 1 may be selected from the structures of the following Table 4.

TABLE 4

| No. | Compound |
|---|---|
| 1 | |
| 2 | |

TABLE 4-continued
| No. | Compound |
|-----|----------|
| 3 | 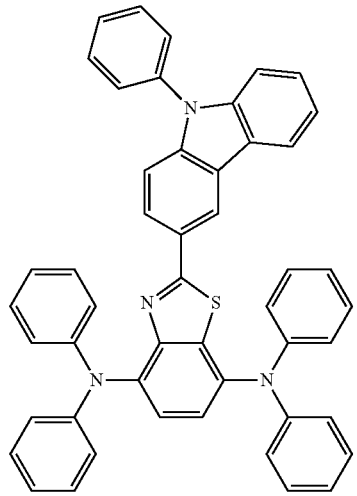 [SMILES: c1ccc(N(c2ccccc2)c2ccc(N(c3ccccc3)c3ccccc3)c3sc(-c4ccc5c(c4)c4ccccc4n5-c4ccccc4)nc23)cc1] |
| 4 | 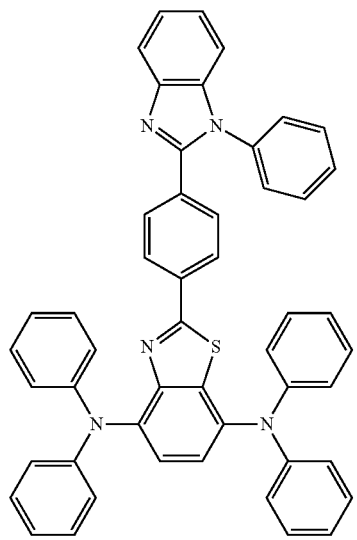 [SMILES: c1ccc(N(c2ccccc2)c2ccc(N(c3ccccc3)c3ccccc3)c3sc(-c4ccc(-c5nc6ccccc6n5-c5ccccc5)cc4)nc23)cc1] |
| 5 | 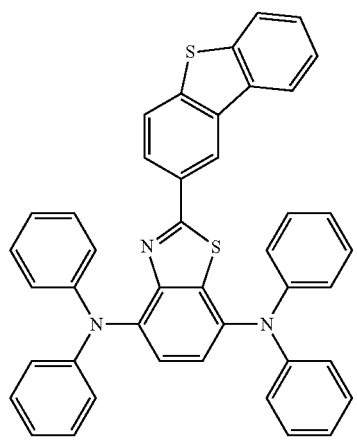 [SMILES: c1ccc(N(c2ccccc2)c2ccc(N(c3ccccc3)c3ccccc3)c3sc(-c4ccc5sc6ccccc6c5c4)nc23)cc1] |

TABLE 4-continued
| No. | Compound |
|---|---|
| 6 | 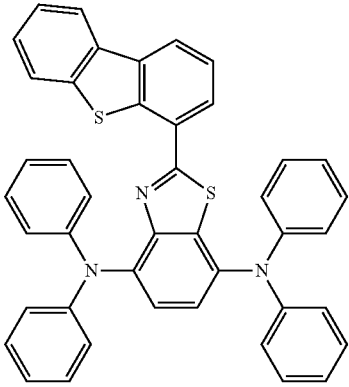 |
| 7 | 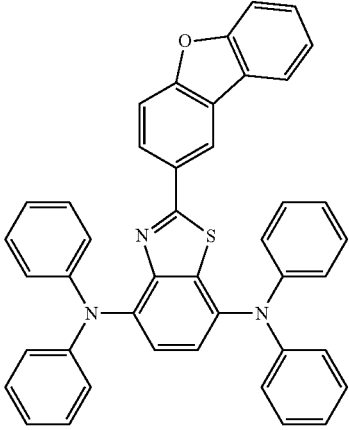 |
| 8 | 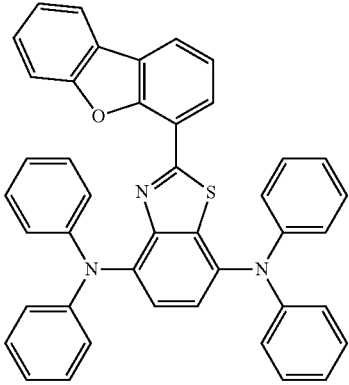 [SMILES: c1ccc(N(c2ccccc2)c2ccc(N(c3ccccc3)c3ccccc3)c3sc(-c4cccc5c4sc4ccccc45)nc23)cc1] |
| 9 | 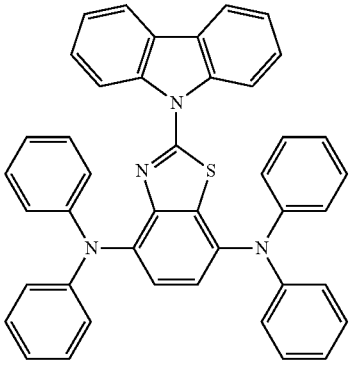 [SMILES: c1ccc(N(c2ccccc2)c2ccc(N(c3ccccc3)c3ccccc3)c3sc(-n4c5ccccc5c5ccccc54)nc23)cc1] |

TABLE 4-continued
| No. | Compound |
|---|---|
| 10 | 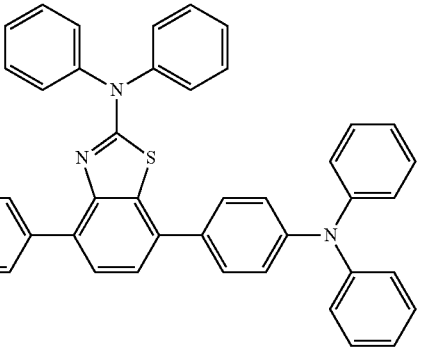 |
| 11 | 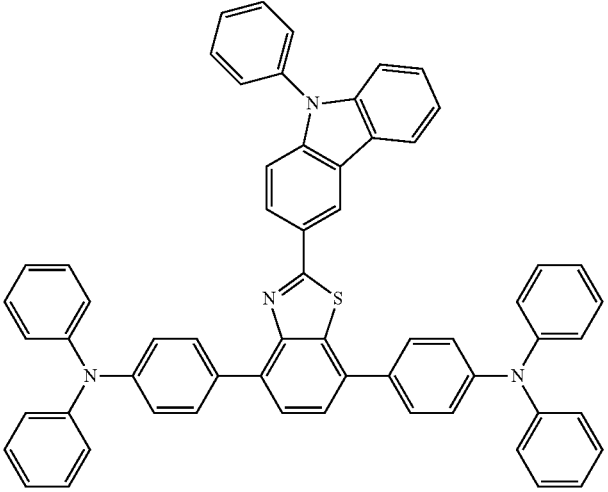 [SMILES: c1ccc(N(c2ccccc2)c2ccc(-c3ccc(-c4ccc(N(c5ccccc5)c5ccccc5)cc4)c4sc(-c5ccc6c(c5)c5ccccc5n6-c5ccccc5)nc34)cc2)cc1] |
| 12 | 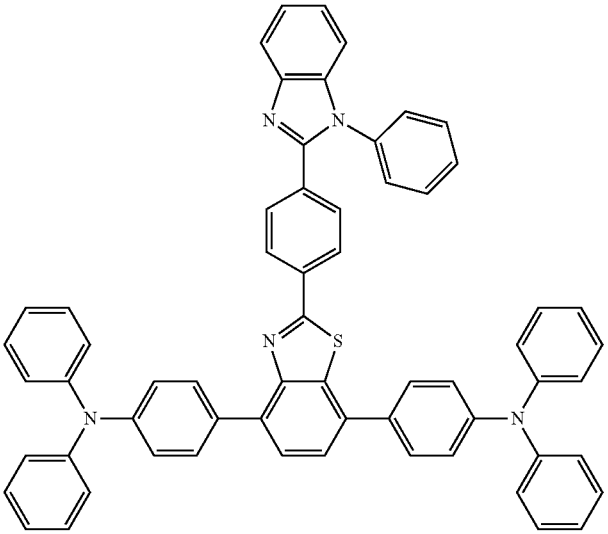 [SMILES: c1ccc(N(c2ccccc2)c2ccc(-c3ccc(-c4ccc(N(c5ccccc5)c5ccccc5)cc4)c4sc(-c5ccc(-c6nc7ccccc7n6-c6ccccc6)cc5)nc34)cc2)cc1] |

TABLE 4-continued

| No. | Compound |
| --- | --- |
| 13 | |
| 14 | |
| 15 | |

TABLE 4-continued
| No. | Compound |
|---|---|
| 16 | 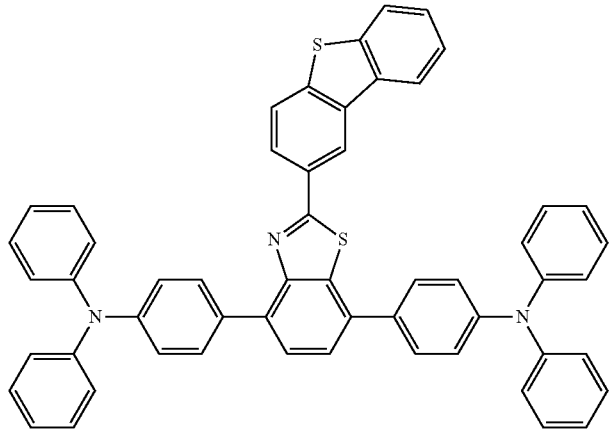 [SMILES: c1ccc(N(c2ccccc2)c2ccc(-c3ccc(-c4ccc(N(c5ccccc5)c5ccccc5)cc4)c4sc(-c5ccc6oc7ccccc7c6c5)nc34)cc2)cc1] |
| 17 | 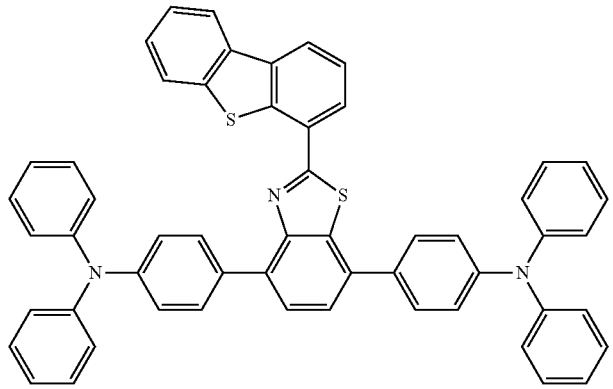 [SMILES: c1ccc(N(c2ccccc2)c2ccc(-c3ccc(-c4ccc(N(c5ccccc5)c5ccccc5)cc4)c4sc(-c5cccc6c5oc5ccccc56)nc34)cc2)cc1] |
| 18 | 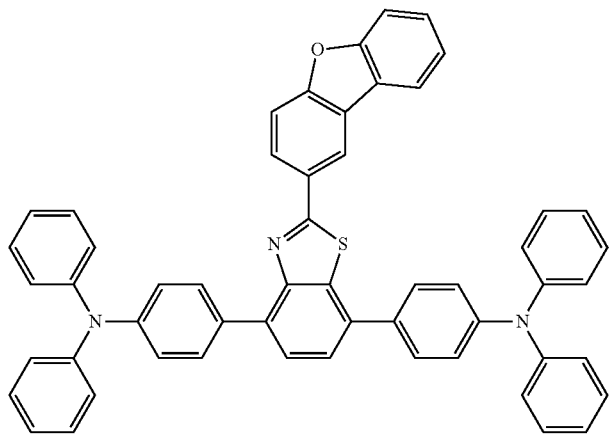 |

TABLE 4-continued
| No. | Compound |
|---|---|
| 19 | 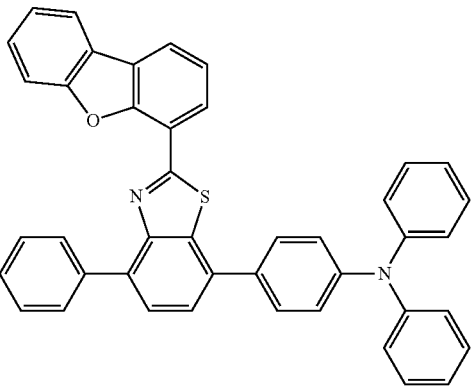 |
| 20 | 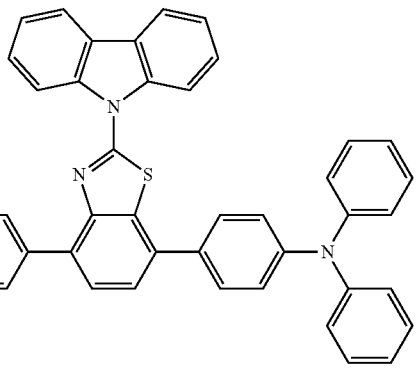 |
| 21 | 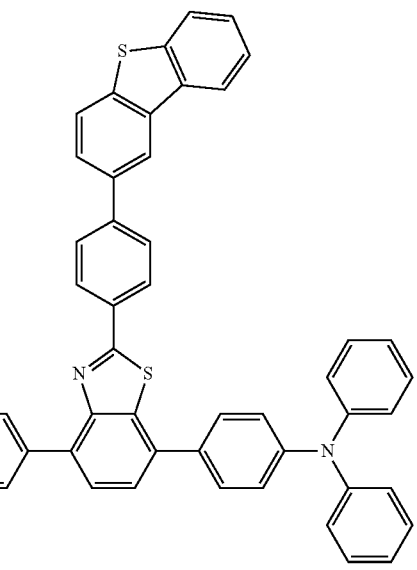 |

TABLE 4-continued
| No. | Compound |
|---|---|
| 22 | 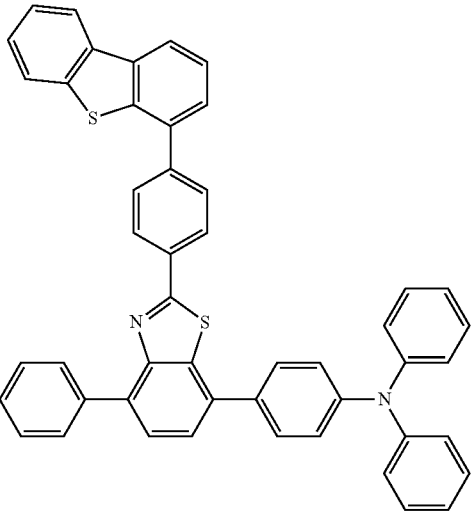 |
| 23 | 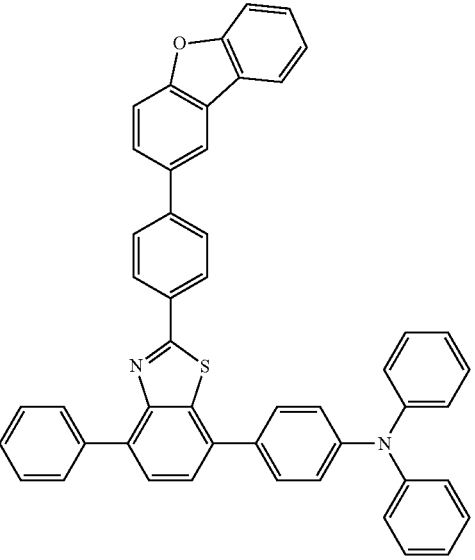 |
| 24 | 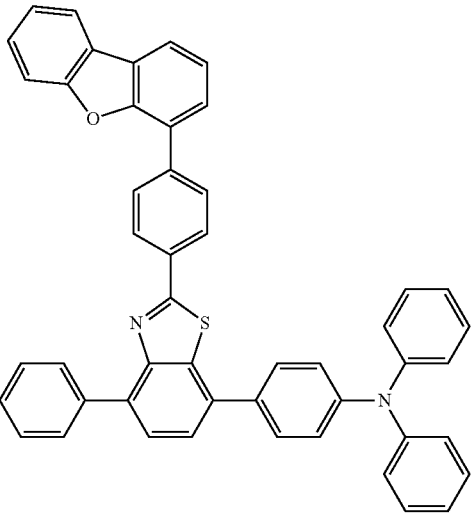 |

TABLE 4-continued
| No. | Compound |
|---|---|
| 25 | 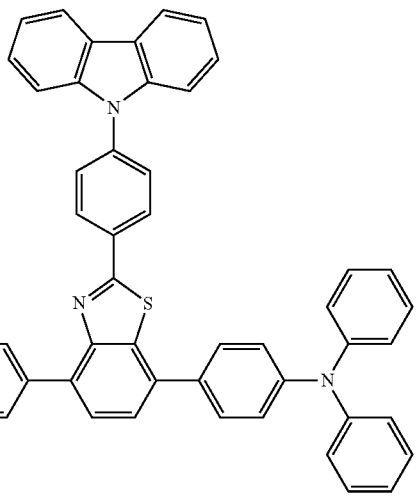 |
In one exemplary embodiment, the novel compound according to the present invention may include a compound in which $Z_1$ and $Z_2$ in Formula 1 are each independently represented by Formula 3.
For example, $Z_3$ in Formula 1 may be selected from the structures of the following Table 5.
TABLE 5
| No. | Substituent structure |
|---|---|
| 1 | 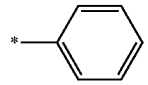 |
| 2 | 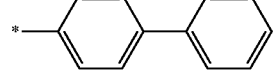 |
| 3 | 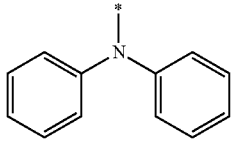 [SMILES: *N(c1ccccc1)c1ccccc1] |
| 4 | 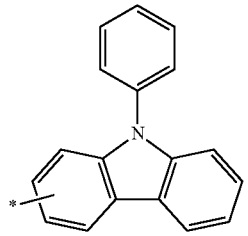 |
| 5 | 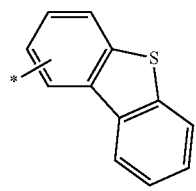 |
| 6 | 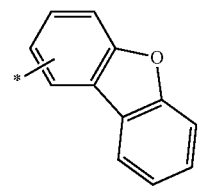 |
| 7 | 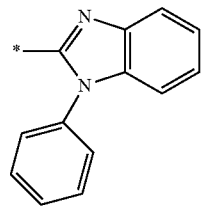 [SMILES: *c1nc2ccccc2n1-c1ccccc1] |
| 8 | 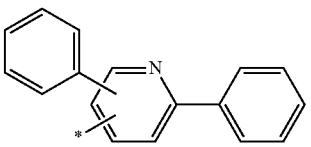 |
| 9 | 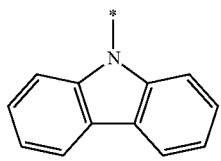 |

In this case, $Z_1$ and $Z_2$ in Formula 1 may be each independently selected from the structures of the following Table 6.

TABLE 6

| No. | Substituent structure |
|---|---|
| 1 | (N-phenylcarbazole, attached via *) |
| 2 | (dibenzothiophene, attached via *) |

TABLE 6-continued

| No. | Substituent structure |
|---|---|
| 3 | (dibenzofuran, attached via *) |

Furthermore, $L_a$, $L_b$, and $L_c$ in Formula 1 may be each independently selected from a single bond or the structures of the following Table 7.

TABLE 7

| No. | Substituent structure |
|---|---|
| 1 | (1,4-phenylene) |
| 2 | (4,4'-biphenylene) |

More specifically, the compound represented by Formula 1 may be selected from the structures of the following Table 8.

TABLE 8

| No. | Compound |
|---|---|
| 1 | (benzothiazole core with 2-phenyl substituent and two 9-phenylcarbazol-3-yl groups at 4,7-positions) |
| 2 | (benzothiazole core with 2-diphenylamino substituent and two 9-phenylcarbazol-3-yl groups at 4,7-positions) |

TABLE 8-continued

| No. | Compound |
|---|---|
| 3 | |
| 4 | |
| 5 | |

TABLE 8-continued
| No. | Compound |
|---|---|
| 6 | 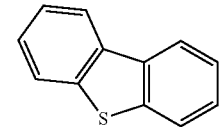 |
| 7 | 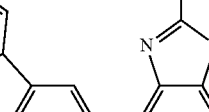 |
| 8 | 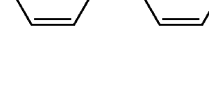 |
| 9 | 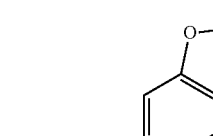 |

TABLE 8-continued

| No. | Compound |
|-----|----------|
| 10  |          |
| 11  |          |
| 12  |          |
| 13  |          |

TABLE 8-continued
| No. | Compound |
|---|---|
| 14 | 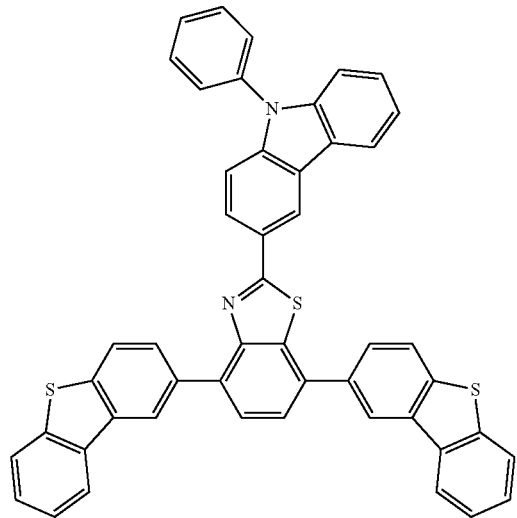 [SMILES: c1ccc(-n2c3ccccc3c3cc(-c4nc5c(-c6ccc7sc8ccccc8c7c6)ccc(-c6ccc7sc8ccccc8c7c6)c5s4)ccc32)cc1] |
| 15 | 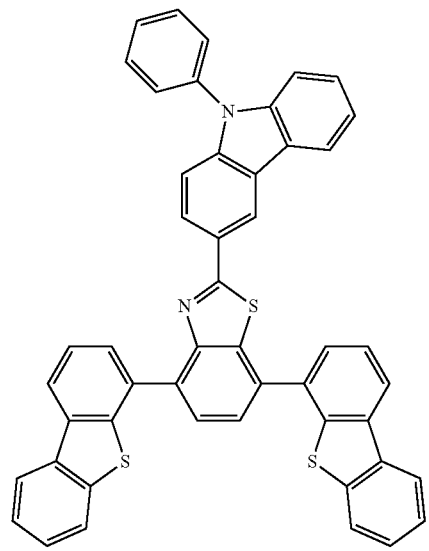 [SMILES: c1ccc(-n2c3ccccc3c3cc(-c4nc5c(-c6cccc7c6sc6ccccc67)ccc(-c6cccc7c6sc6ccccc67)c5s4)ccc32)cc1] |

US 9,966,538 B2
37 38
TABLE 8-continued
| No. | Compound |
|---|---|
| 16 | 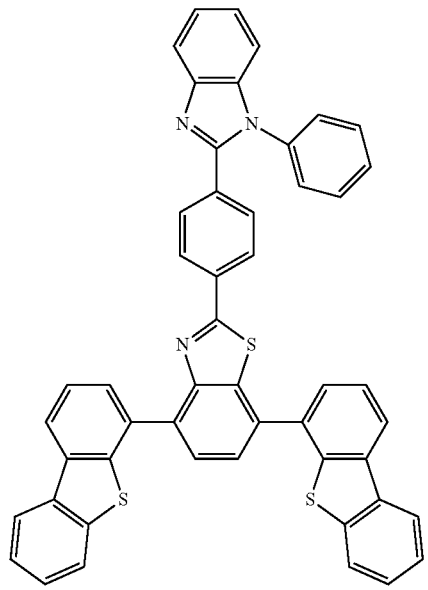 [SMILES: c1ccc(-n2c(-c3ccc(-c4nc5c(-c6cccc7c6sc6ccccc67)ccc(-c6cccc7c6sc6ccccc67)c5s4)cc3)nc3ccccc32)cc1] |
| 17 | 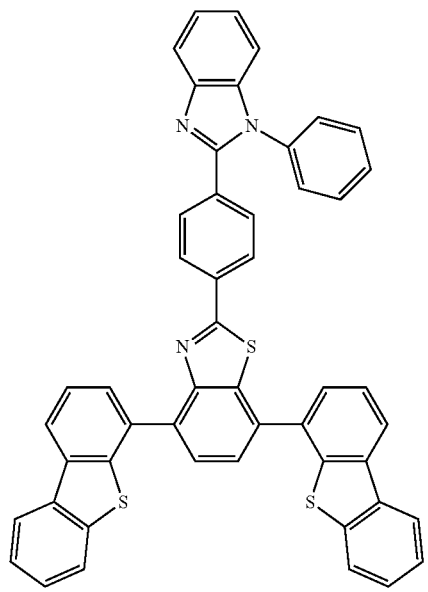 |
| 18 | 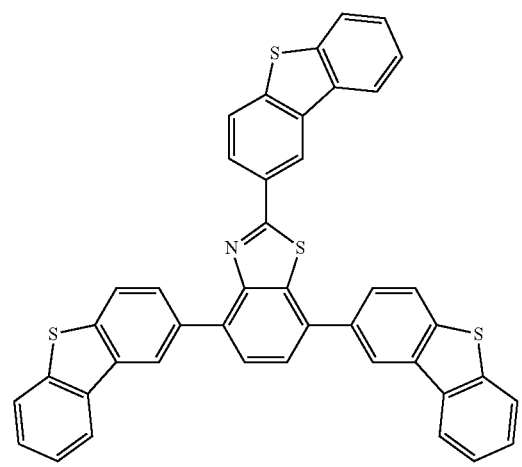 |

TABLE 8-continued
| No. | Compound |
|---|---|
| 19 | 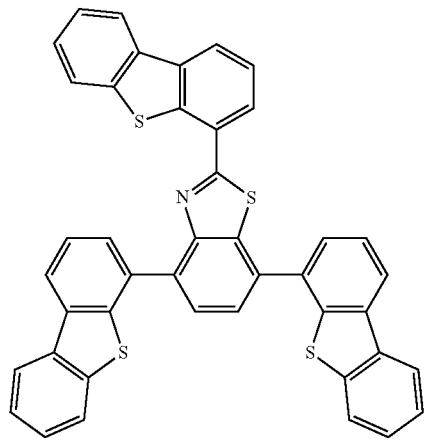 |
| 20 | 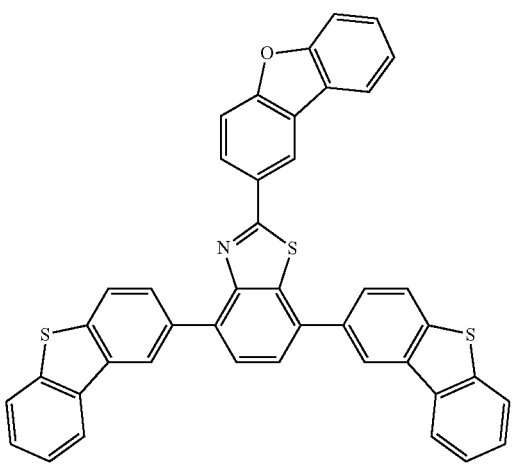 [SMILES: c1ccc2c(c1)oc1ccc(-c3nc4c(-c5ccc6sc7ccccc7c6c5)ccc(-c5ccc6sc7ccccc7c6c5)c4s3)cc12] |
| 21 | 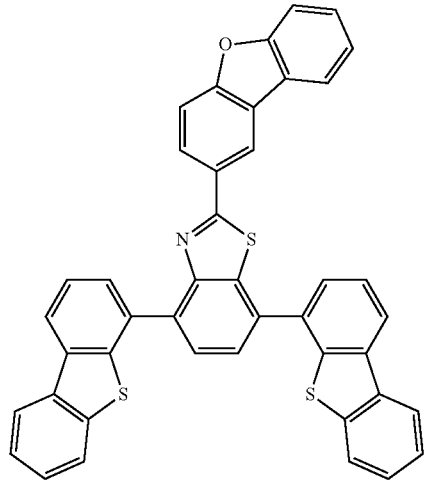 |

TABLE 8-continued

| No. | Compound |
|---|---|
| 22 | |
| 23 | |
| 24 | |

TABLE 8-continued

| No. | Compound |
|---|---|
| 25 | |
| 26 | |
| 27 | |
| 28 | |

TABLE 8-continued
| No. | Compound |
|---|---|
| 29 | 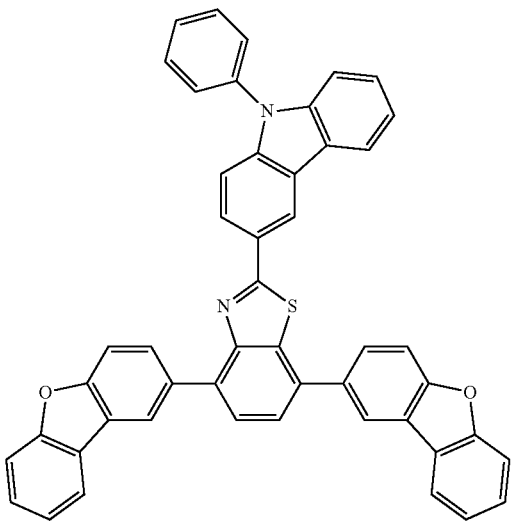 [SMILES: c1ccc(-n2c3ccccc3c3cc(-c4nc5c(-c6ccc7oc8ccccc8c7c6)ccc(-c6ccc7oc8ccccc8c7c6)c5s4)ccc32)cc1] |
| 30 | 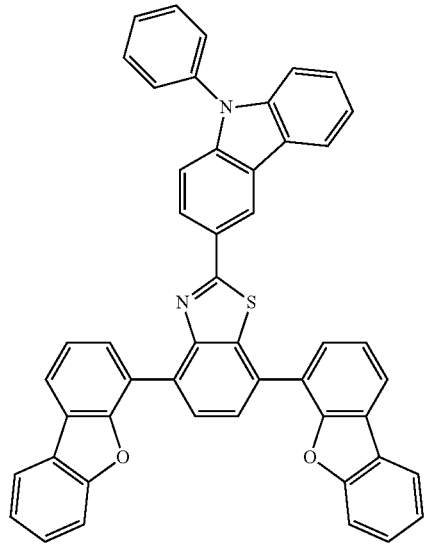 [SMILES: c1ccc(-n2c3ccccc3c3cc(-c4nc5c(-c6cccc7c6oc6ccccc67)ccc(-c6cccc7c6oc6ccccc67)c5s4)ccc32)cc1] |
| 31 | 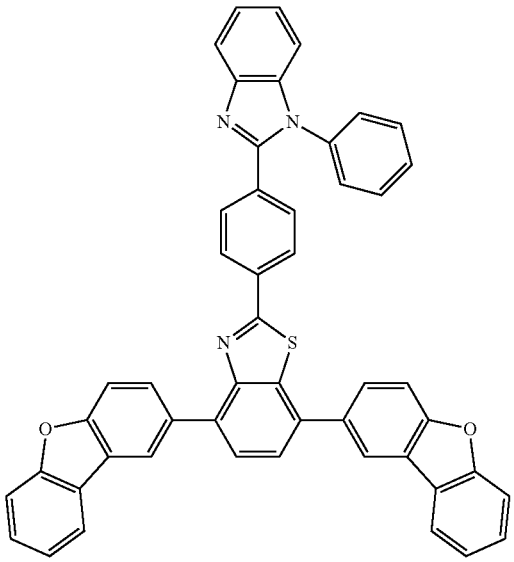 [SMILES: c1ccc(-n2c(-c3ccc(-c4nc5c(-c6ccc7oc8ccccc8c7c6)ccc(-c6ccc7oc8ccccc8c7c6)c5s4)cc3)nc3ccccc32)cc1] |

TABLE 8-continued

| No. | Compound |
|-----|----------|
| 32  |          |
| 33  |          |
| 34  |          |

TABLE 8-continued
| No. | Compound |
|---|---|
| 35 | 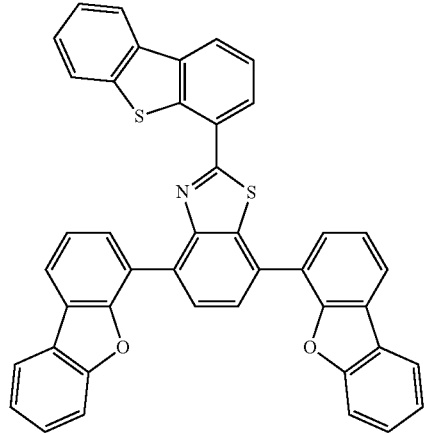 |
| 36 | 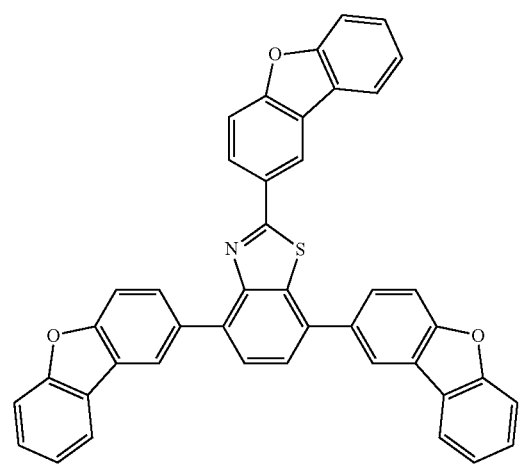 [SMILES: c1ccc2c(c1)oc1ccc(-c3ccc(-c4ccc5oc6ccccc6c5c4)c4sc(-c5ccc6sc7ccccc7c6c5)nc34)cc12] |
| 37 | 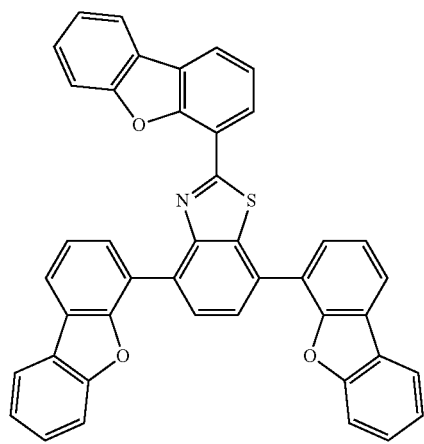 [SMILES: c1ccc2c(c1)oc1c(-c3ccc(-c4cccc5c4oc4ccccc45)c4sc(-c5cccc6c5sc5ccccc56)nc34)cccc12] |

TABLE 8-continued
| No. | Compound |
|---|---|
| 38 | 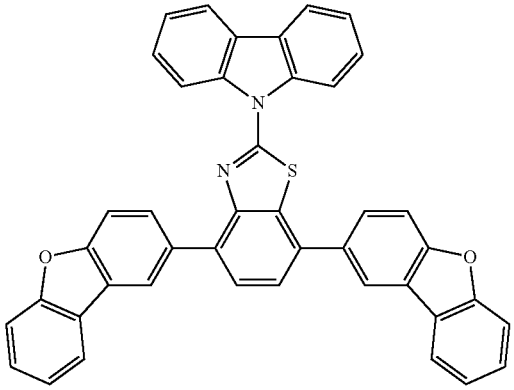 [SMILES: c1ccc2c(c1)oc1ccc(-c3ccc(-c4ccc5oc6ccccc6c5c4)c4sc(-n5c6ccccc6c6ccccc65)nc34)cc12] |
| 39 | 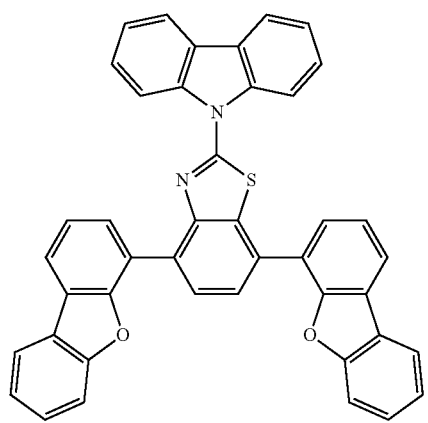 [SMILES: c1ccc2c(c1)oc1c(-c3ccc(-c4cccc5c4oc4ccccc45)c4sc(-n5c6ccccc6c6ccccc65)nc34)cccc12] |
| 40 | 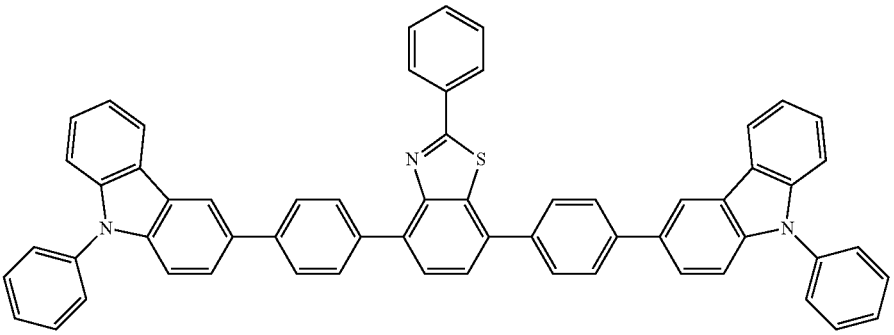 [SMILES: c1ccc(-c2nc3c(-c4ccc(-c5ccc6c(c5)c5ccccc5n6-c5ccccc5)cc4)ccc(-c4ccc(-c5ccc6c(c5)c5ccccc5n6-c5ccccc5)cc4)c3s2)cc1] |
| 41 | 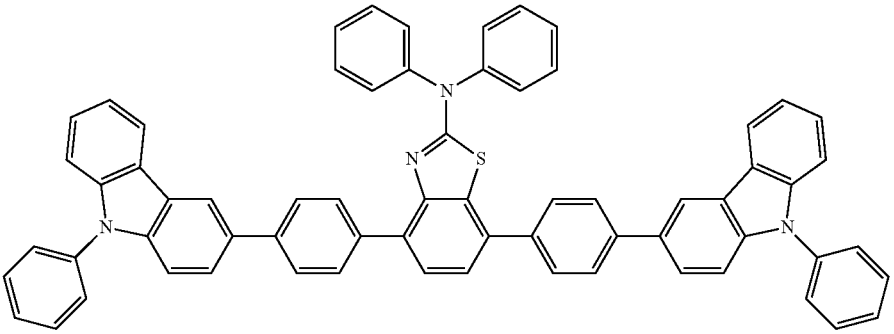 [SMILES: c1ccc(N(c2ccccc2)c2nc3c(-c4ccc(-c5ccc6c(c5)c5ccccc5n6-c5ccccc5)cc4)ccc(-c4ccc(-c5ccc6c(c5)c5ccccc5n6-c5ccccc5)cc4)c3s2)cc1] |

TABLE 8-continued

| No. | Compound |
|---|---|
| 42 | |
| 43 | |
| 44 | |

TABLE 8-continued
| No. | Compound |
|---|---|
| 45 | 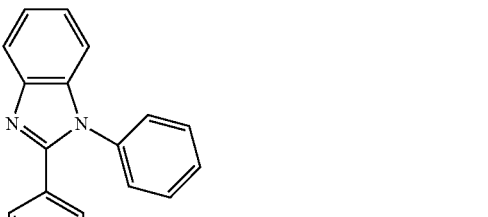 |
| 46 | 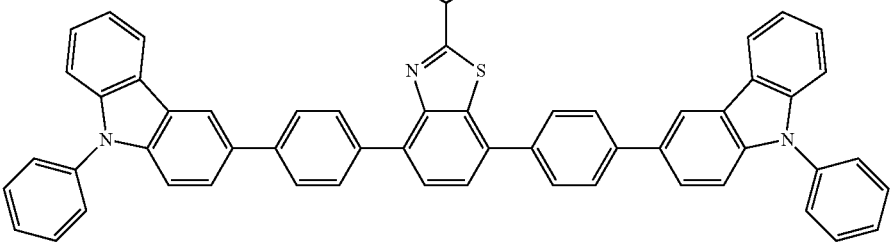 |
| 47 | 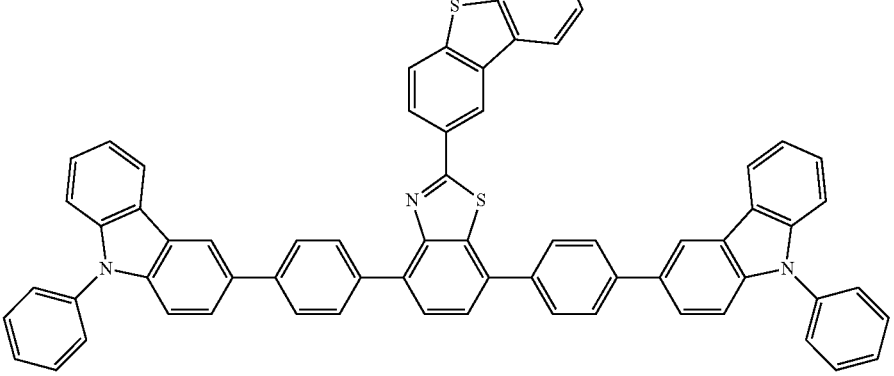 |

TABLE 8-continued

| No. | Compound |
|---|---|
| 48 | |
| 49 | |
| 50 | |

TABLE 8-continued
| No. | Compound |
| --- | --- |
| 51 | 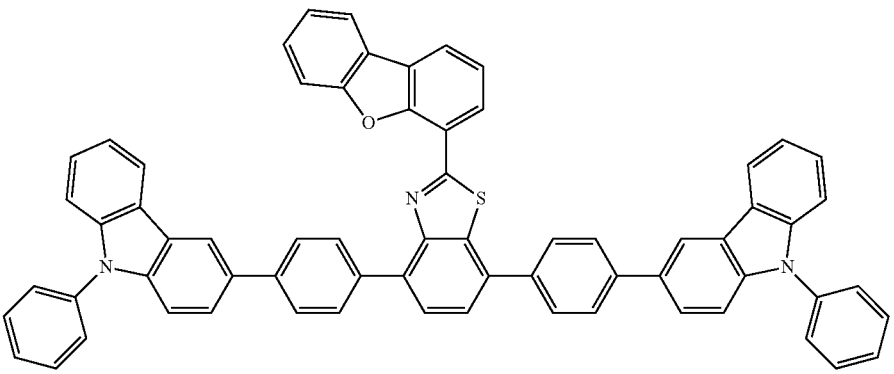 [SMILES: c1ccc(-n2c3ccccc3c3cc(-c4ccc(-c5ccc(-c6ccc(-c7ccc8c(c7)c7ccccc7n8-c7ccccc7)cc6)c6sc(-c7cccc8c7sc7ccccc78)nc56)cc4)ccc32)cc1] |
| 52 | 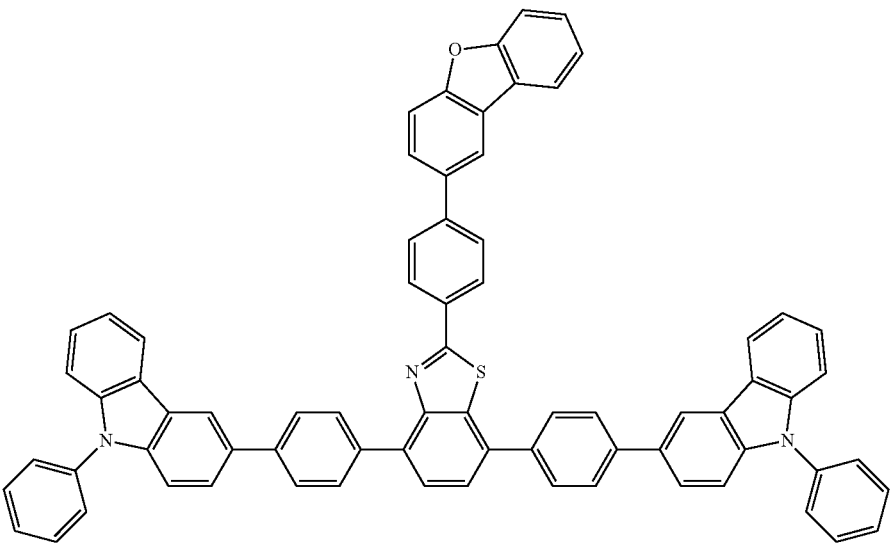 |
| 53 | 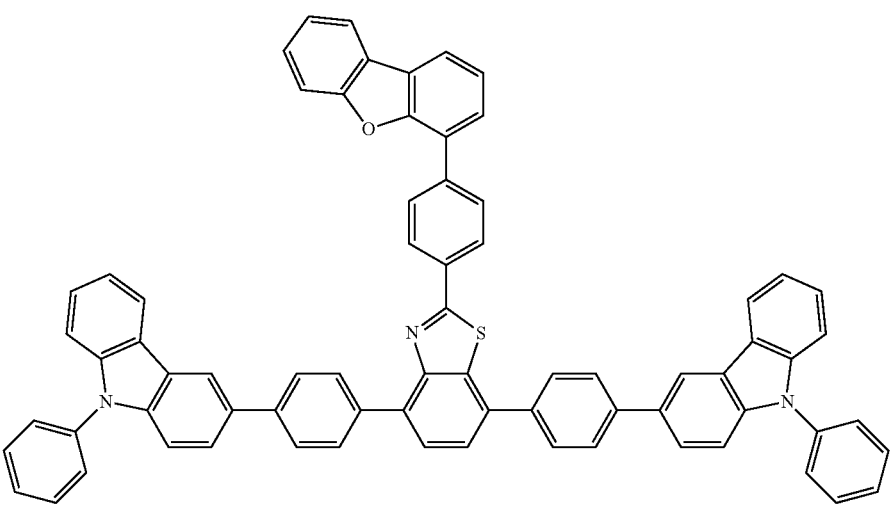 [SMILES: c1ccc(-n2c3ccccc3c3cc(-c4ccc(-c5ccc(-c6ccc(-c7ccc8c(c7)c7ccccc7n8-c7ccccc7)cc6)c6sc(-c7ccc(-c8cccc9c8sc8ccccc89)cc7)nc56)cc4)ccc32)cc1] |

TABLE 8-continued

| No. | Compound |
|---|---|
| 54 | |
| 55 | |
| 56 | |
| 57 | |

TABLE 8-continued
| No. | Compound |
|---|---|
| 58 | 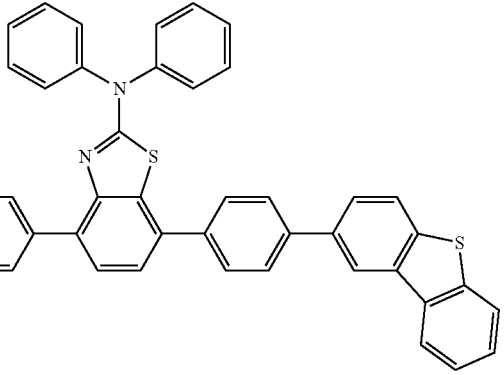 |
| 59 | 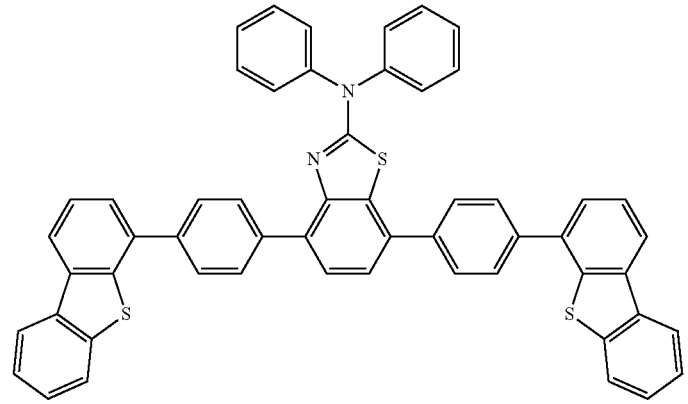 [SMILES: c1ccc(N(c2ccccc2)c2nc3c(-c4ccc(-c5cccc6c5sc5ccccc56)cc4)ccc(-c4ccc(-c5cccc6c5sc5ccccc56)cc4)c3s2)cc1] |
| 60 | 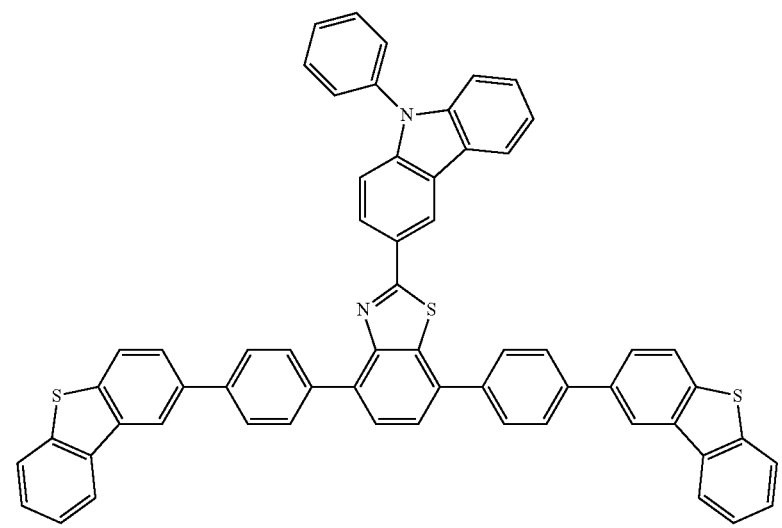 [SMILES: c1ccc(-n2c3ccccc3c3cc(-c4nc5c(-c6ccc(-c7ccc8sc9ccccc9c8c7)cc6)ccc(-c6ccc(-c7ccc8sc9ccccc9c8c7)cc6)c5s4)ccc32)cc1] |

TABLE 8-continued
| No. | Compound |
|---|---|
| 61 | 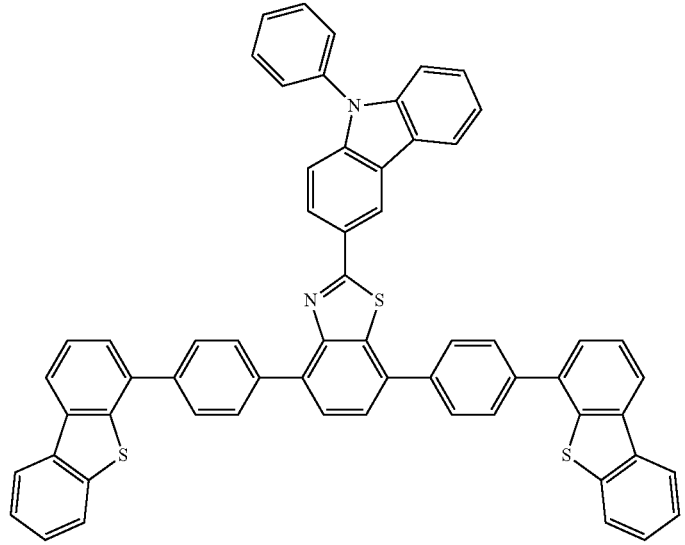 [SMILES: c1ccc(-n2c3ccccc3c3cc(-c4nc5c(-c6ccc(-c7cccc8c7sc7ccccc78)cc6)ccc(-c6ccc(-c7cccc8c7sc7ccccc78)cc6)c5s4)ccc32)cc1] |
| 62 | 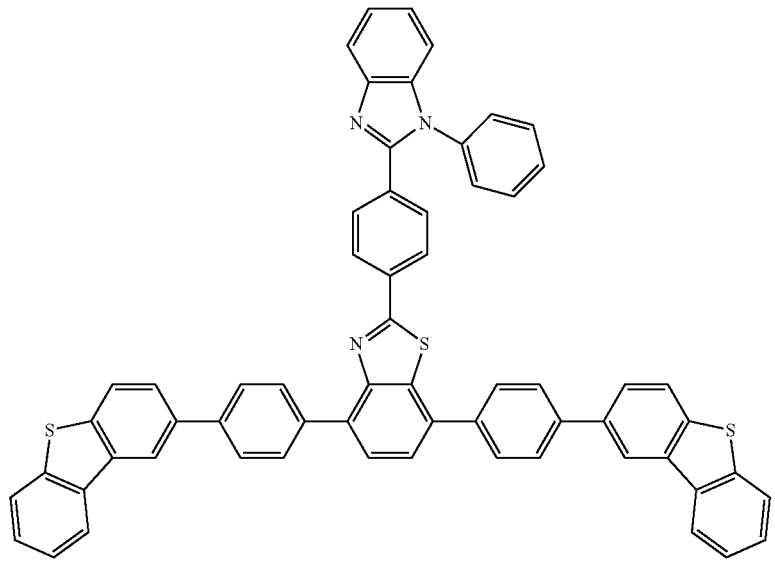 [SMILES: c1ccc(-n2c(-c3ccc(-c4nc5c(-c6ccc(-c7ccc8sc9ccccc9c8c7)cc6)ccc(-c6ccc(-c7ccc8sc9ccccc9c8c7)cc6)c5s4)cc3)nc3ccccc32)cc1] |

TABLE 8-continued
| No. | Compound |
|---|---|
| 63 | 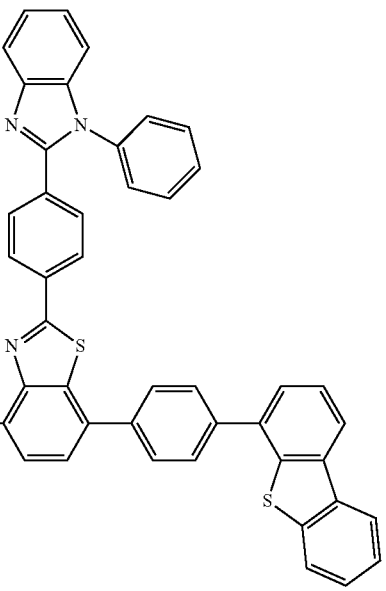 |
| 64 | 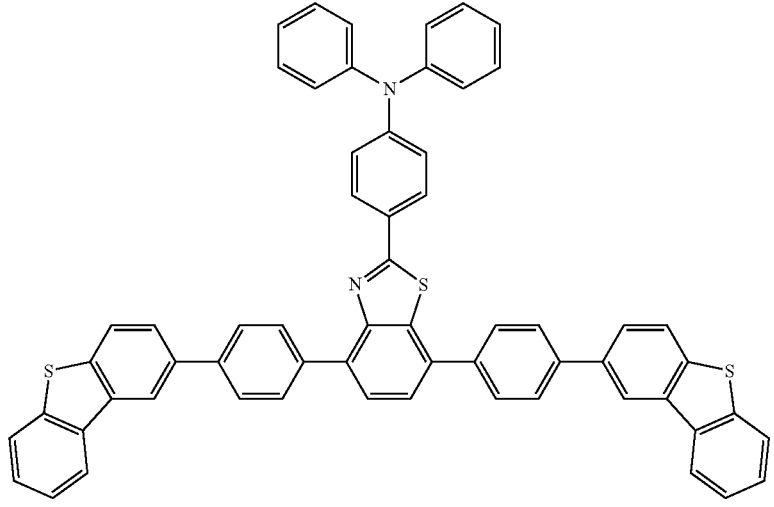 |
| 65 | 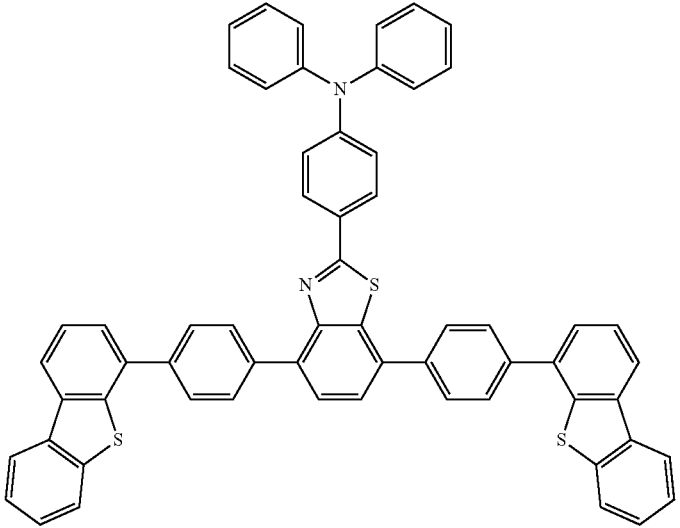 |

TABLE 8-continued
| No. | Compound |
|---|---|
| 66 | 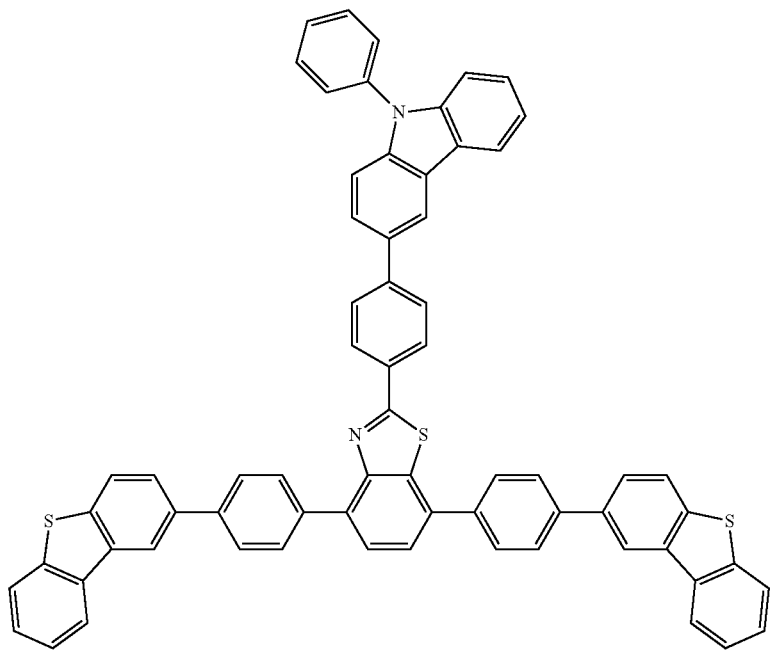 [SMILES: c1ccc(-n2c3ccccc3c3cc(-c4ccc(-c5nc6c(-c7ccc(-c8ccc9sc%10ccccc%10c9c8)cc7)ccc(-c7ccc(-c8ccc9sc%10ccccc%10c9c8)cc7)c6s5)cc4)ccc32)cc1] |
| 67 | 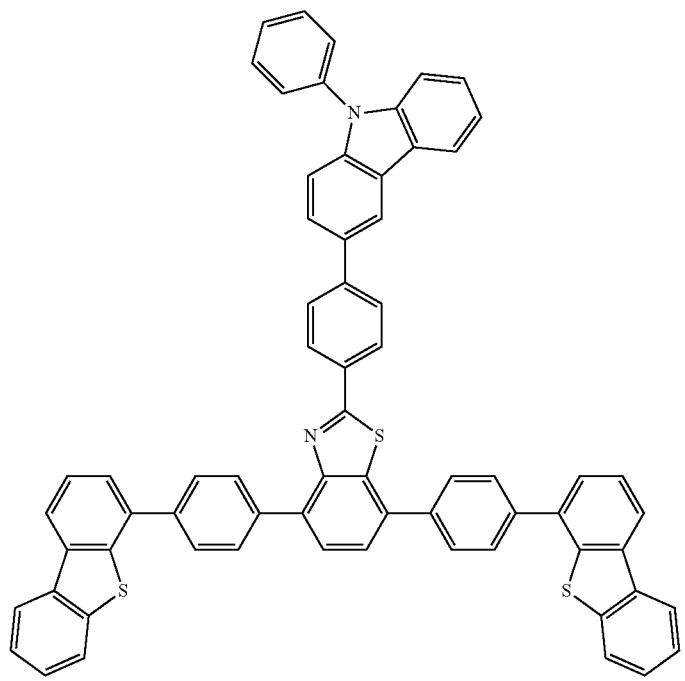 [SMILES: c1ccc(-n2c3ccccc3c3cc(-c4ccc(-c5nc6c(-c7ccc(-c8cccc9c8sc8ccccc89)cc7)ccc(-c7ccc(-c8cccc9c8sc8ccccc89)cc7)c6s5)cc4)ccc32)cc1] |

TABLE 8-continued

| No. | Compound |
|---|---|
| 68 | |
| 69 | |
| 70 | |

TABLE 8-continued
| No. | Compound |
|---|---|
| 71 | 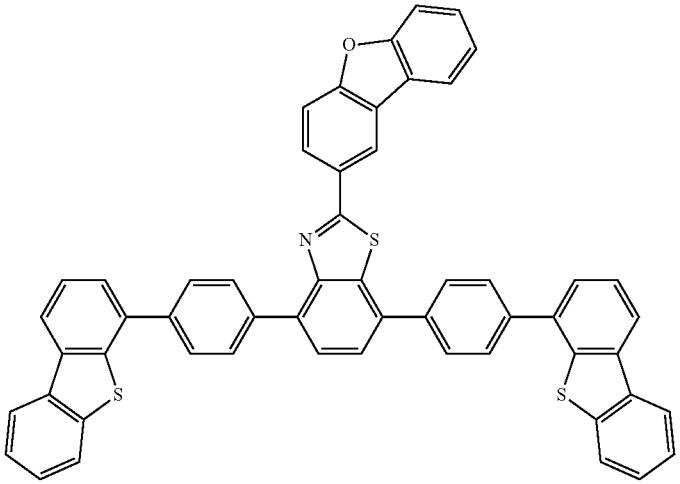 |
| 72 | 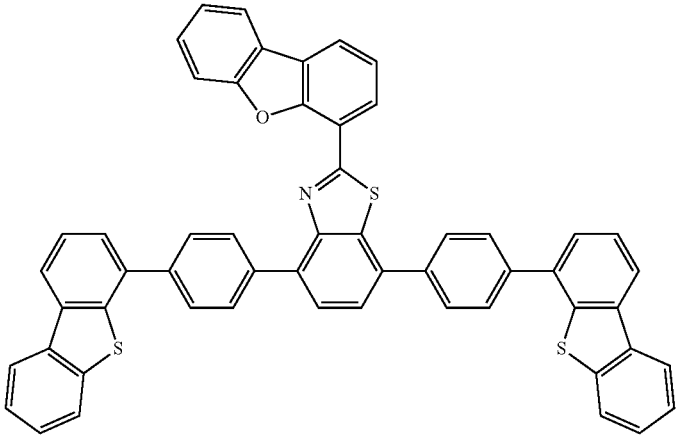 [SMILES: c1ccc2c(c1)sc1c(-c3ccc(-c4ccc(-c5ccc(-c6cccc7c6sc6ccccc67)cc5)c5sc(-c6cccc7c6sc6ccccc67)nc45)cc3)cccc12] |
| 73 | 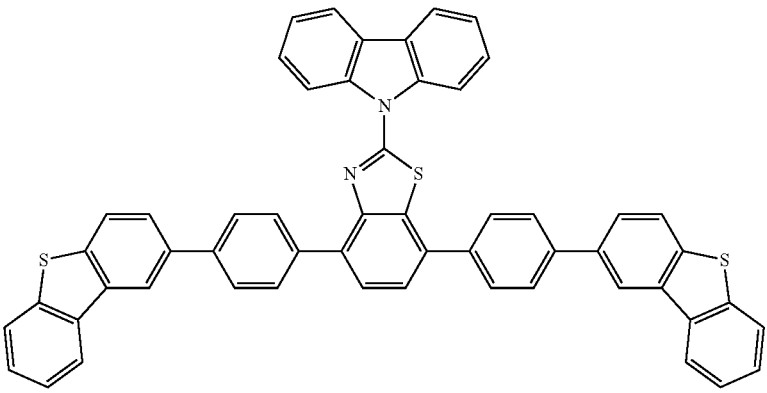 [SMILES: c1ccc2c(c1)sc1ccc(-c3ccc(-c4ccc(-c5ccc(-c6ccc7sc8ccccc8c7c6)cc5)c5sc(-n6c7ccccc7c7ccccc76)nc45)cc3)cc12] |

TABLE 8-continued
| No. | Compound |
|---|---|
| 74 | 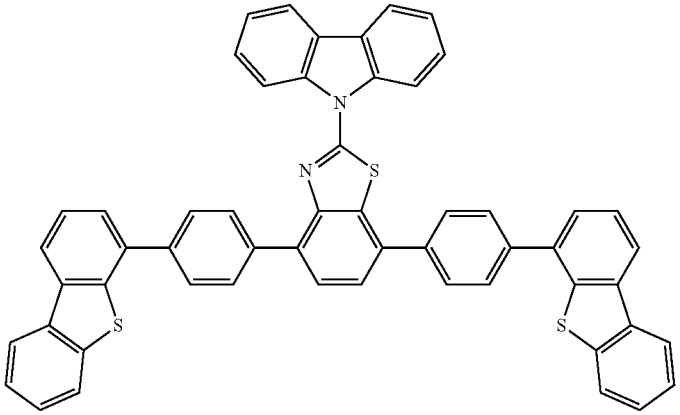 [SMILES: c1ccc2c(c1)sc1c(-c3ccc(-c4ccc(-c5ccc(-c6cccc7c6sc6ccccc67)cc5)c5sc(-n6c7ccccc7c7ccccc76)nc45)cc3)cccc12] |
| 75 | 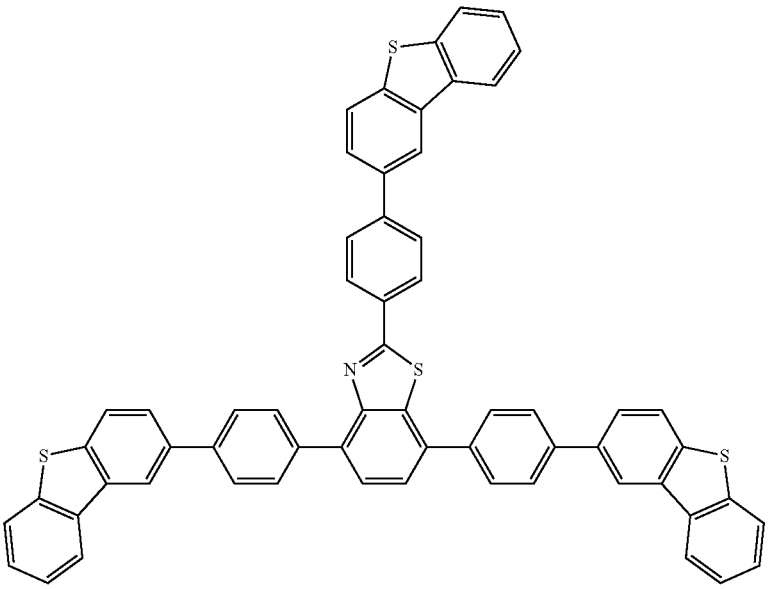 [SMILES: c1ccc2c(c1)sc1ccc(-c3ccc(-c4nc5c(-c6ccc(-c7ccc8sc9ccccc9c8c7)cc6)ccc(-c6ccc(-c7ccc8sc9ccccc9c8c7)cc6)c5s4)cc3)cc12] |
| 76 | 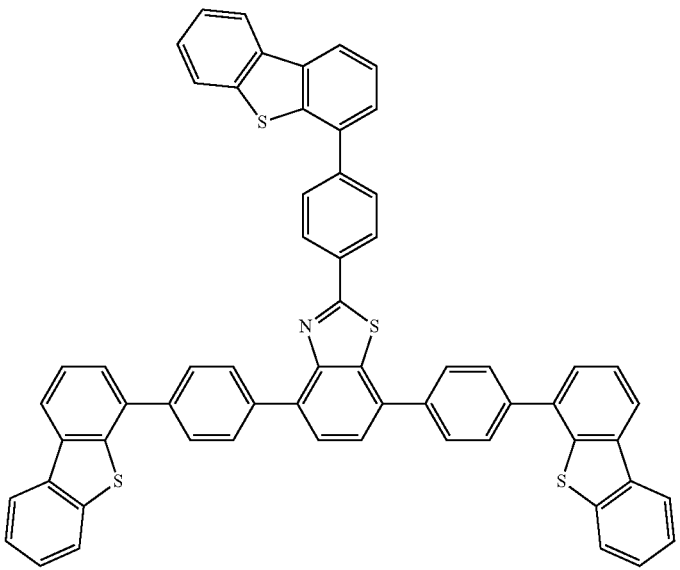 [SMILES: c1ccc2c(c1)sc1c(-c3ccc(-c4nc5c(-c6ccc(-c7cccc8c7sc7ccccc78)cc6)ccc(-c6ccc(-c7cccc8c7sc7ccccc78)cc6)c5s4)cc3)cccc12] |

TABLE 8-continued
| No. | Compound |
|---|---|
| 77 | 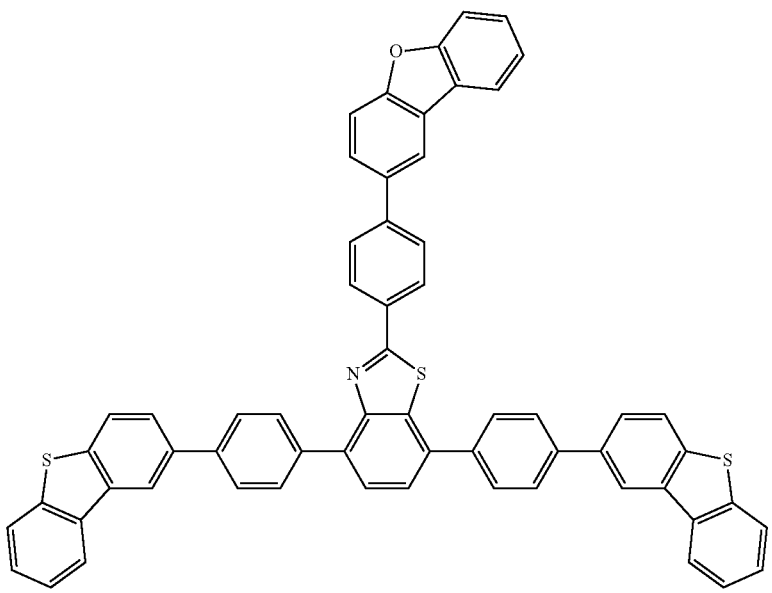 [SMILES: c1ccc2c(c1)oc1ccc(-c3ccc(-c4nc5c(-c6ccc(-c7ccc8sc9ccccc9c8c7)cc6)ccc(-c6ccc(-c7ccc8sc9ccccc9c8c7)cc6)c5s4)cc3)cc12] |
| 78 | 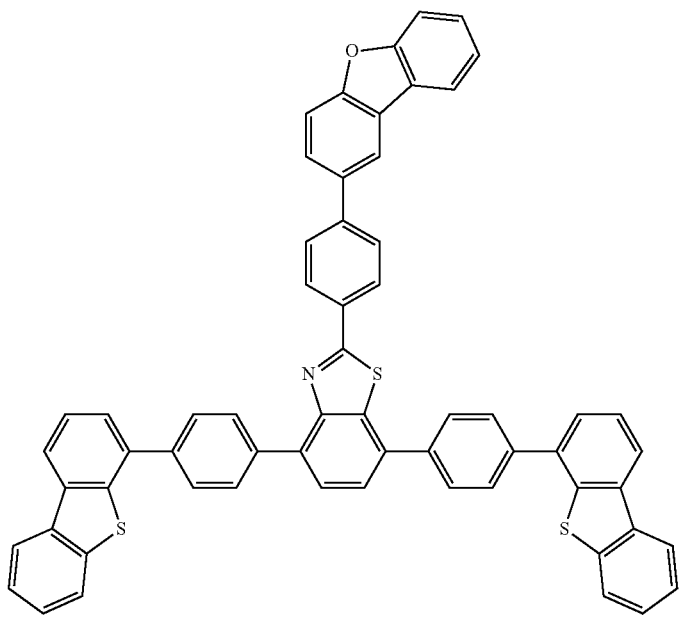 [SMILES: c1ccc2c(c1)oc1ccc(-c3ccc(-c4nc5c(-c6ccc(-c7cccc8c7sc7ccccc78)cc6)ccc(-c6ccc(-c7cccc8c7sc7ccccc78)cc6)c5s4)cc3)cc12] |

TABLE 8-continued
| No. | Compound |
|---|---|
| 79 | 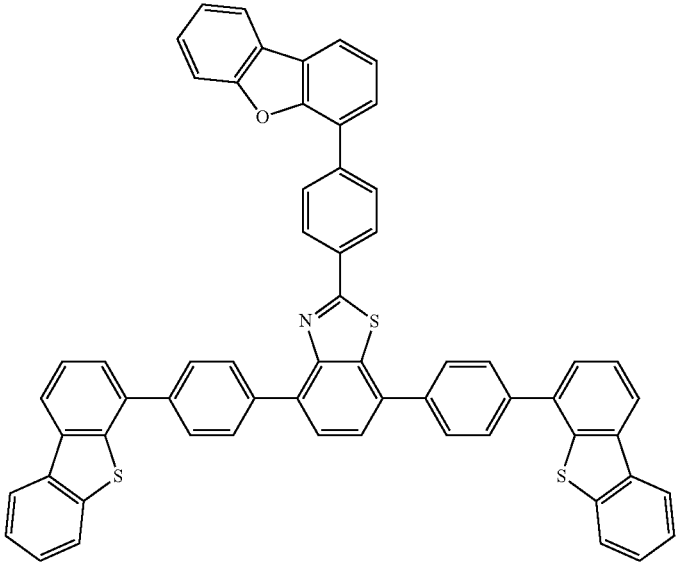 |
| 80 | 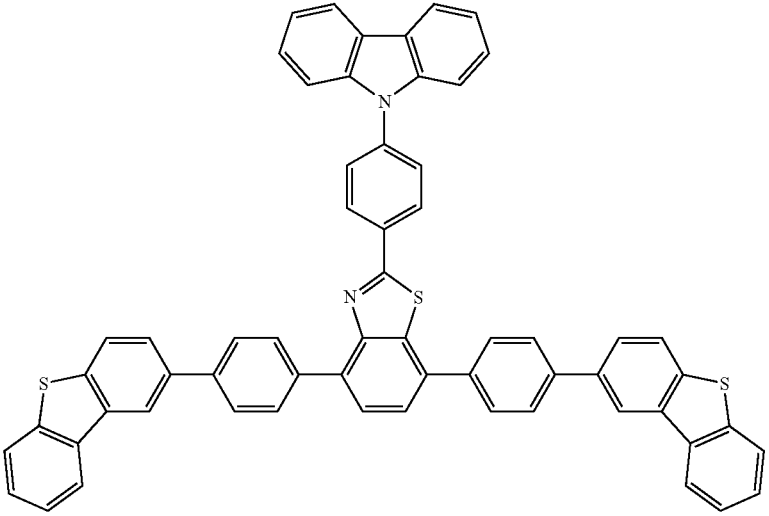 [SMILES: c1ccc2c(c1)sc1ccc(-c3ccc(-c4ccc(-c5ccc(-c6ccc7sc8ccccc8c7c6)cc5)c5sc(-c6ccc(-n7c8ccccc8c8ccccc87)cc6)nc45)cc3)cc12] |
| 81 | 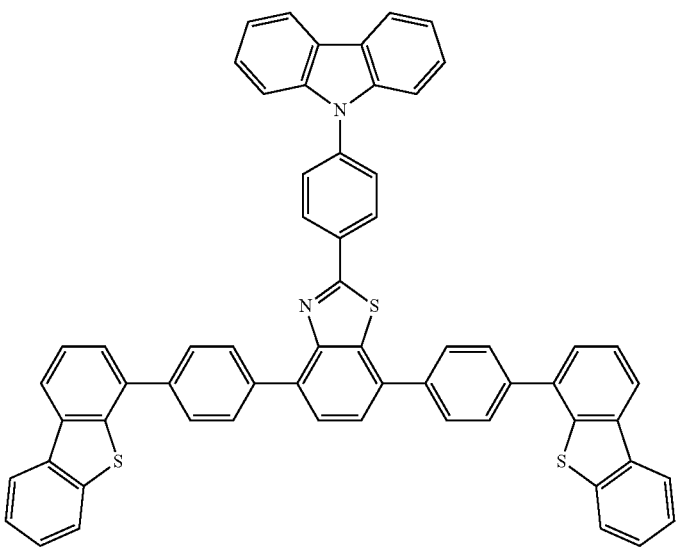 [SMILES: c1ccc2c(c1)sc1c(-c3ccc(-c4ccc(-c5ccc(-c6cccc7c6sc6ccccc67)cc5)c5sc(-c6ccc(-n7c8ccccc8c8ccccc87)cc6)nc45)cc3)cccc12] |

TABLE 8-continued

| No. | Compound |
|---|---|
| 82 | |
| 83 | |
| 84 | |
| 85 | |

TABLE 8-continued
| No. | Compound |
|---|---|
| 86 | 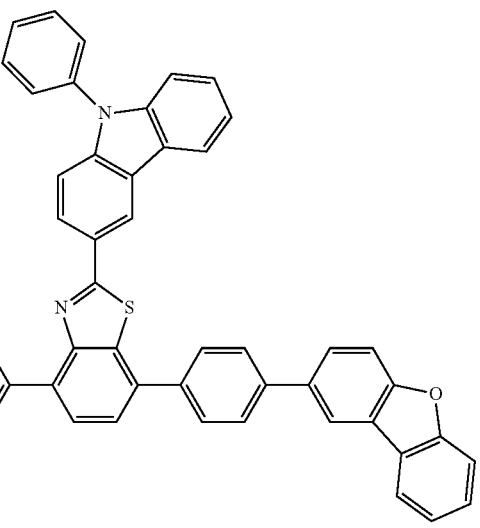 |
| 87 | 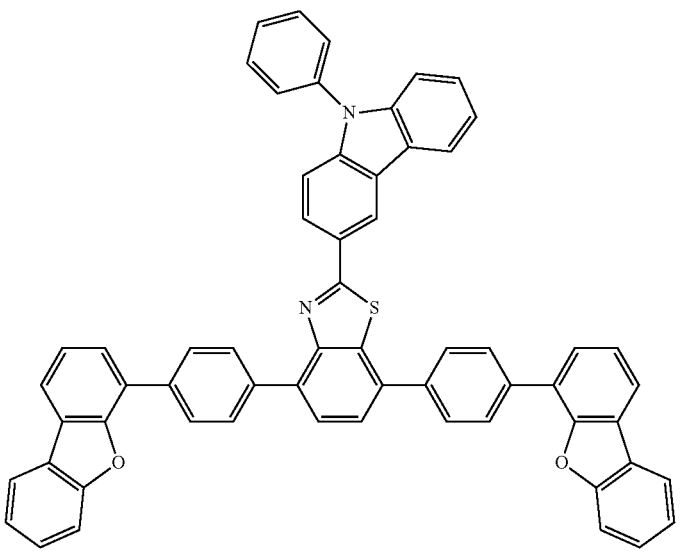 [SMILES: c1ccc(-n2c3ccccc3c3cc(-c4nc5c(-c6ccc(-c7cccc8c7oc7ccccc78)cc6)ccc(-c6ccc(-c7cccc8c7oc7ccccc78)cc6)c5s4)ccc32)cc1] |
| 88 | 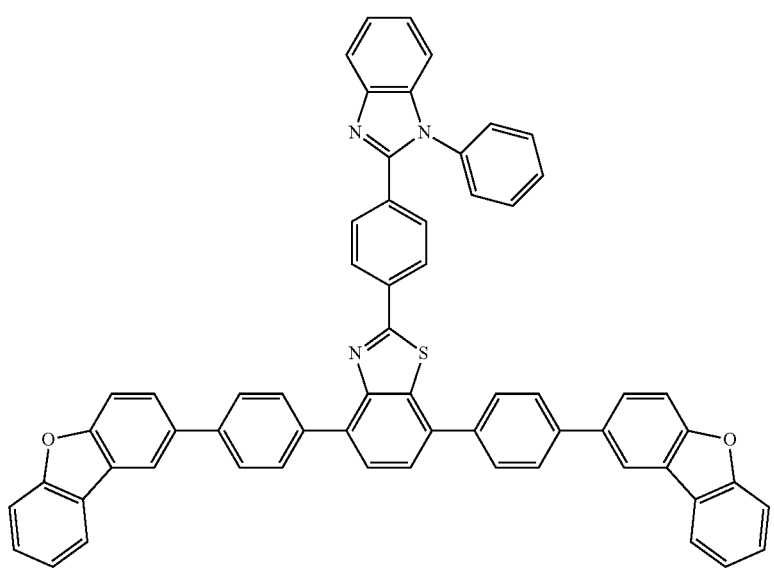 [SMILES: c1ccc(-n2c(-c3ccc(-c4nc5c(-c6ccc(-c7ccc8oc9ccccc9c8c7)cc6)ccc(-c6ccc(-c7ccc8oc9ccccc9c8c7)cc6)c5s4)cc3)nc3ccccc32)cc1] |

TABLE 8-continued
| No. | Compound |
|---|---|
| 89 | 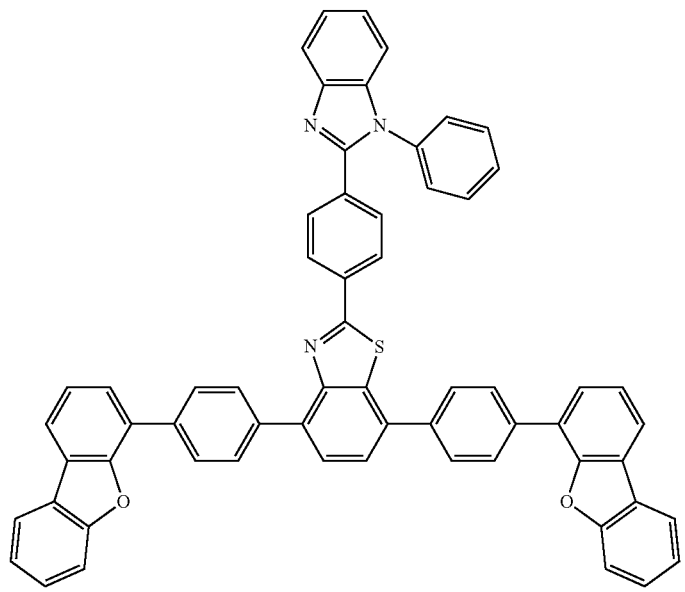 [SMILES: c1ccc(-n2c(-c3ccc(-c4nc5c(-c6ccc(-c7cccc8c7oc7ccccc78)cc6)ccc(-c6ccc(-c7cccc8c7oc7ccccc78)cc6)c5s4)cc3)nc3ccccc32)cc1] |
| 90 | 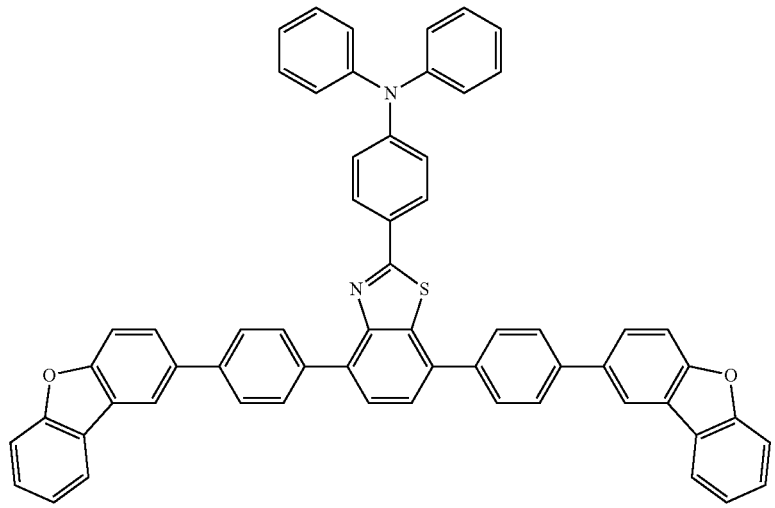 |

TABLE 8-continued
| No. | Compound |
|---|---|
| 91 | 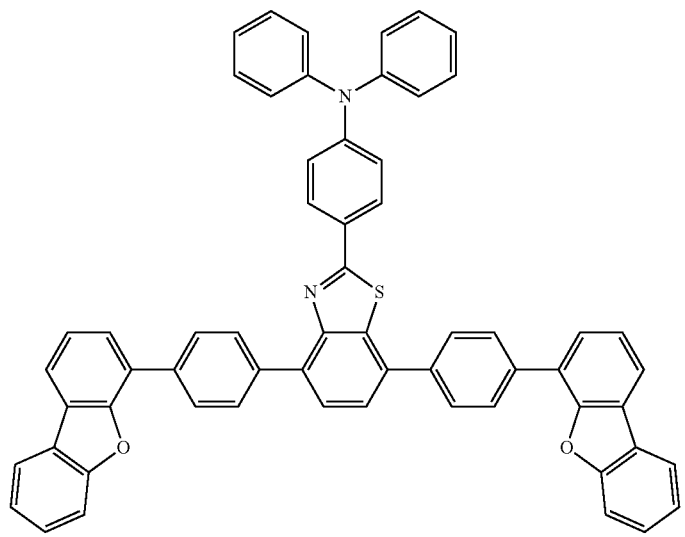 [SMILES: c1ccc(N(c2ccccc2)c2ccc(-c3nc4c(-c5ccc(-c6cccc7c6oc6ccccc67)cc5)ccc(-c5ccc(-c6cccc7c6oc6ccccc67)cc5)c4s3)cc2)cc1] |
| 92 | 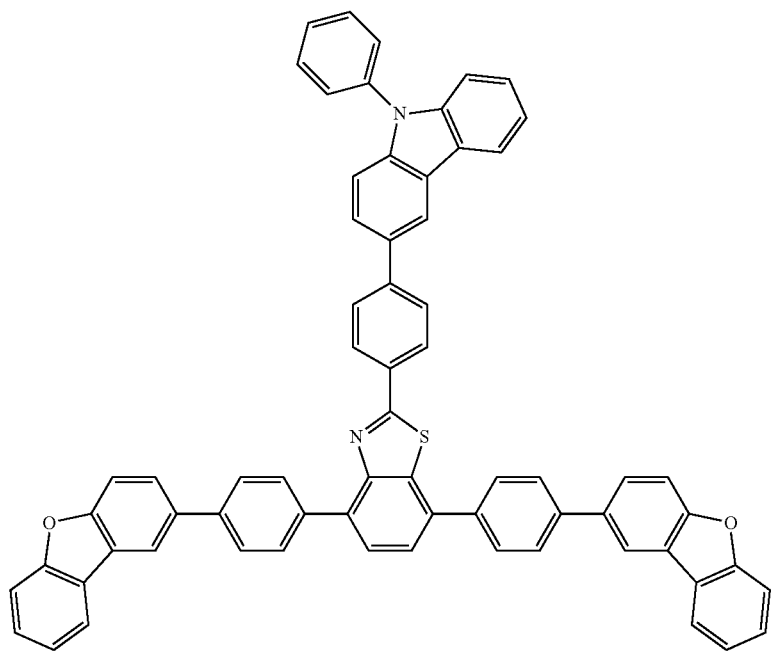 [SMILES: c1ccc(-n2c3ccccc3c3cc(-c4ccc(-c5nc6c(-c7ccc(-c8ccc9oc%10ccccc%10c9c8)cc7)ccc(-c7ccc(-c8ccc9oc%10ccccc%10c9c8)cc7)c6s5)cc4)ccc32)cc1] |

TABLE 8-continued

| No. | Compound |
|---|---|
| 93 | |
| 94 | |
| 95 | |

TABLE 8-continued
| No. | Compound |
|---|---|
| 96 | 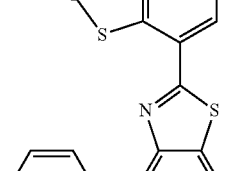 |
| 97 | 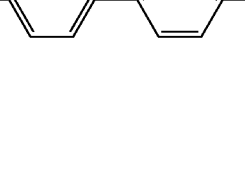 |
| 98 | 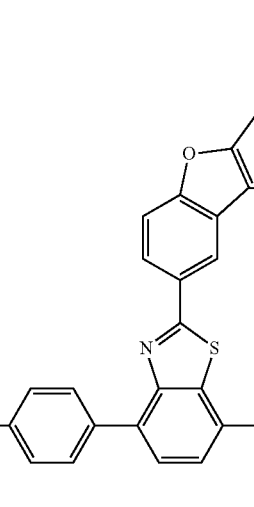 |

93
TABLE 8-continued
| No. | Compound |
|---|---|
| 99 | 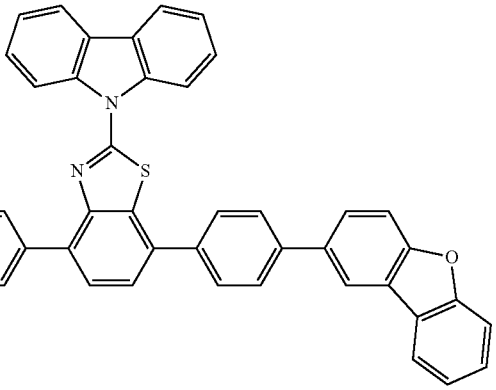 |
| 100 | 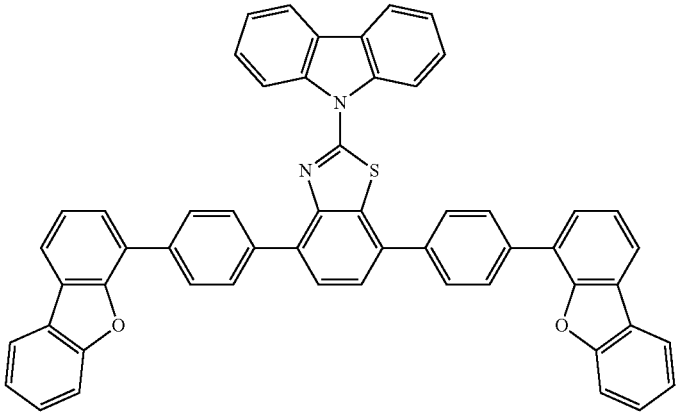 [SMILES: c1ccc2c(c1)oc1c(-c3ccc(-c4ccc(-c5ccc(-c6cccc7c6oc6ccccc67)cc5)c5sc(-n6c7ccccc7c7ccccc76)nc45)cc3)cccc12] |
| 101 | 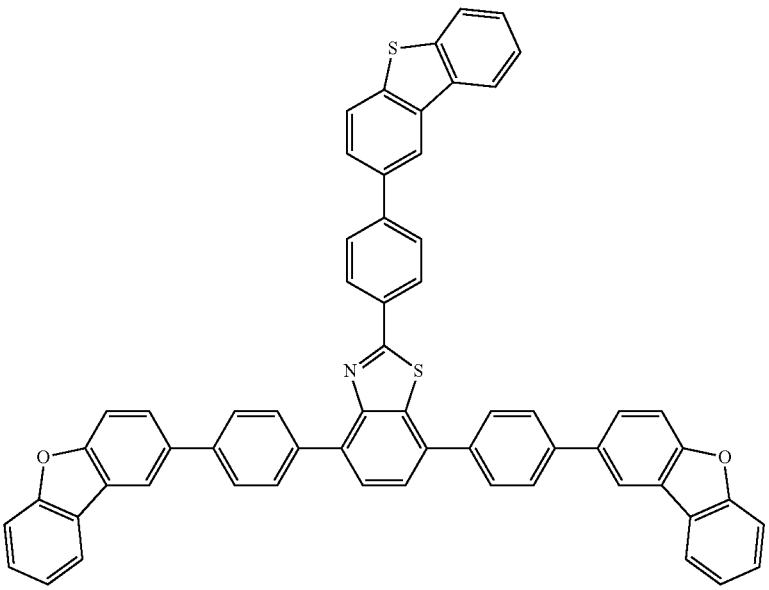 [SMILES: c1ccc2c(c1)oc1ccc(-c3ccc(-c4ccc(-c5ccc(-c6ccc7oc8ccccc8c7c6)cc5)c5sc(-c6ccc(-c7ccc8sc9ccccc9c8c7)cc6)nc45)cc3)cc12] |

TABLE 8-continued
| No. | Compound |
|---|---|
| 102 | 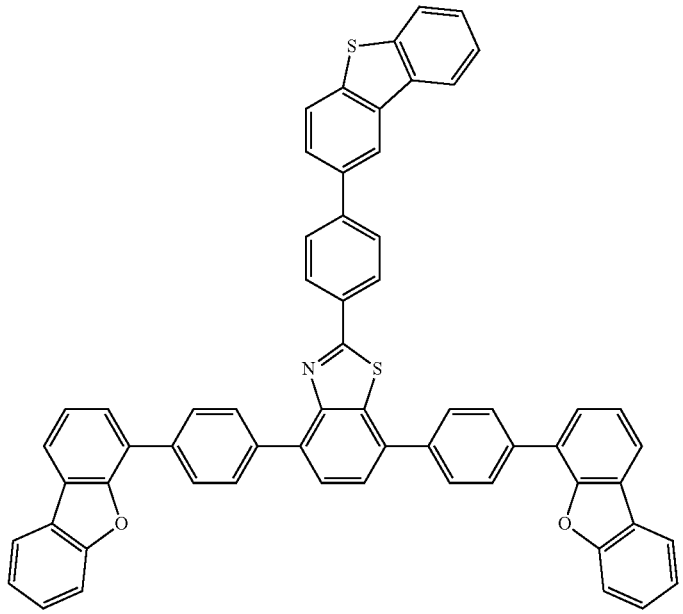 [SMILES: c1ccc2c(c1)oc1c(-c3ccc(-c4ccc(-c5ccc(-c6cccc7c6oc6ccccc67)cc5)c5sc(-c6ccc(-c7ccc8sc9ccccc9c8c7)cc6)nc45)cc3)cccc12] |
| 103 | 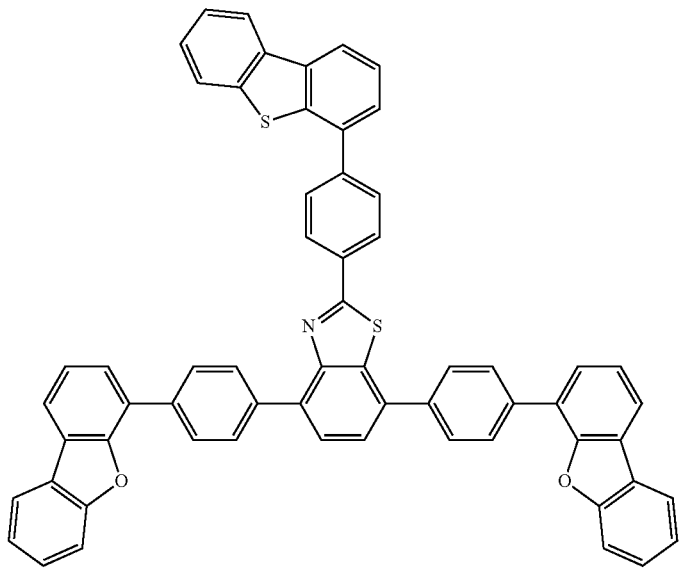 |

TABLE 8-continued
| No. | Compound |
|---|---|
| 104 | 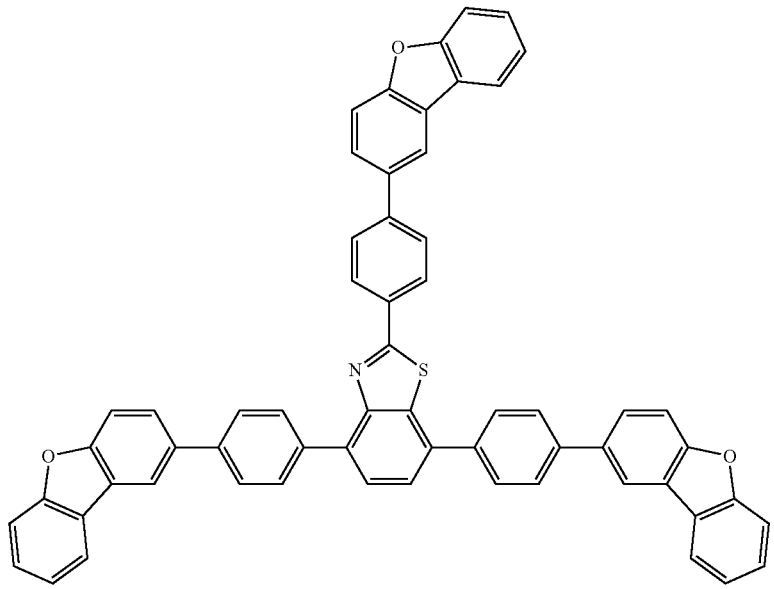 |
| 105 | 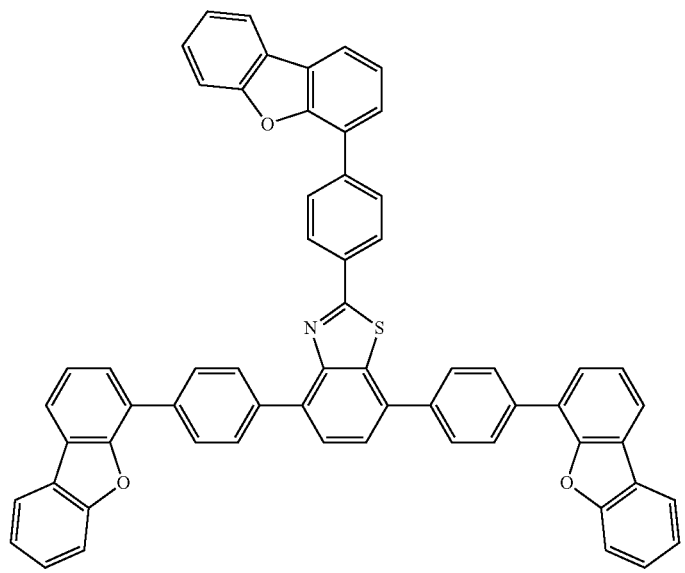 [SMILES: c1ccc2c(c1)oc1c(-c3ccc(-c4ccc(-c5ccc(-c6cccc7c6oc6ccccc67)cc5)c5sc(-c6ccc(-c7cccc8c7sc7ccccc78)cc6)nc45)cc3)cccc12] |

TABLE 8-continued
| No. | Compound |
|---|---|
| 106 | 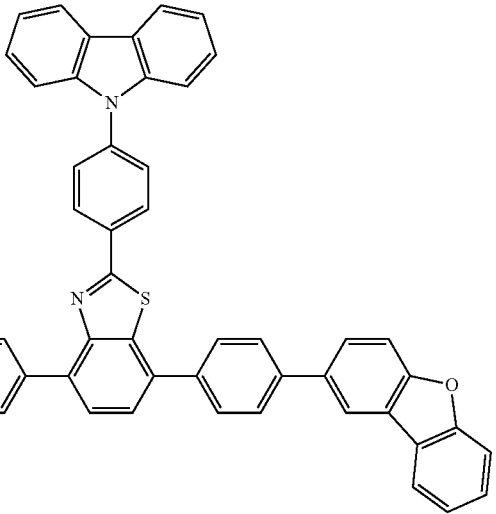 |
| 107 | 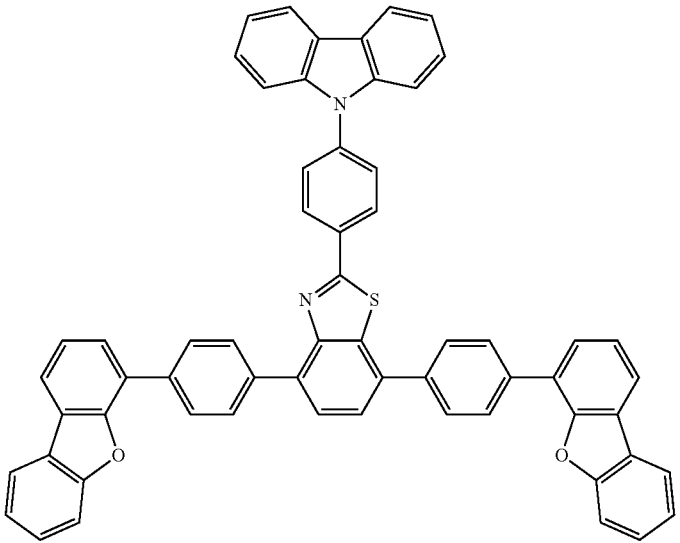 [SMILES: c1ccc2c(c1)oc1c(-c3ccc(-c4ccc(-c5ccc(-c6cccc7c6oc6ccccc67)cc5)c5sc(-c6ccc(-n7c8ccccc8c8ccccc87)cc6)nc45)cc3)cccc12] |
In one exemplary embodiment, the compound of the present invention may include a compound in which $Z_1$ and $Z_2$ in Formula 1 are each independently represented by Formula 4.
For example, $Z_3$ in Formula 1 may be selected from the structures of the following Table 9.
TABLE 9
| No. | Substituent structure |
|---|---|
| 1 | 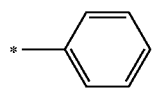 |
| 2 | 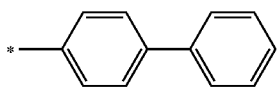 |
TABLE 9-continued
| No. | Substituent structure |
|---|---|
| 3 | 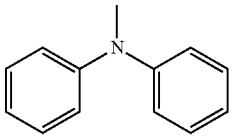 |
| 4 | 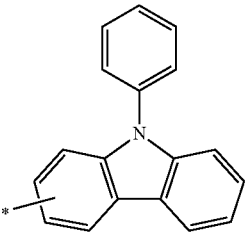 |

TABLE 9-continued

| No. | Substituent structure |
|---|---|
| 5 | 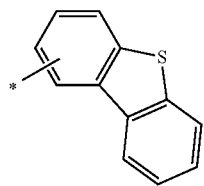 |
| 6 | 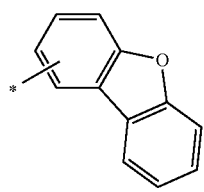 |
| 7 | 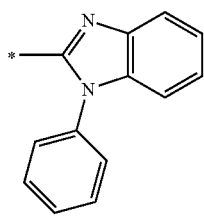 [SMILES: Cc1nc2ccccc2n1-c1ccccc1] |
| 8 | 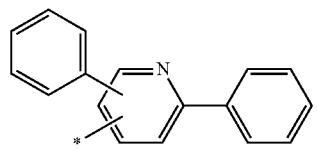 |

TABLE 9-continued

| No. | Substituent structure |
|---|---|
| 9 | 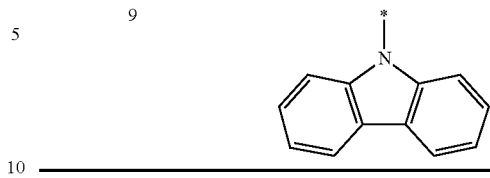 |

In this case, $Z_1$ and $Z_2$ in Formula 1 may be each independently selected from the structure of the following Table 10.

TABLE 10

| No. | Substituent structure |
|---|---|
| 1 | 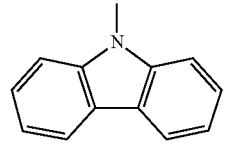 |

Further, $L_a$, $L_b$, and $L_c$ in Formula 1 may be each independently selected from a single bond or the structures of the following Table 11.

TABLE 11

| No. | Substituent structure |
|---|---|
| 1 | 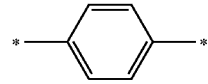 |
| 2 | 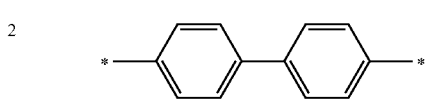 |

More specifically, the compound represented by Formula 1 may be selected from the structures of the following Table 12.

TABLE 12

| No. | Compound |
|---|---|
| 1 | 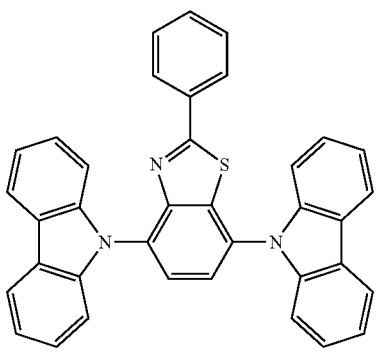 [SMILES: c1ccc(-c2nc3c(-n4c5ccccc5c5ccccc54)ccc(-n4c5ccccc5c5ccccc54)c3s2)cc1] |

TABLE 12-continued
| No. | Compound |
|---|---|
| 2 | 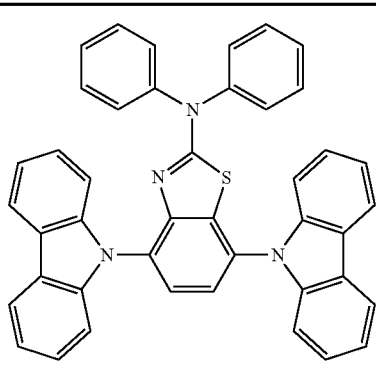 |
| 3 | 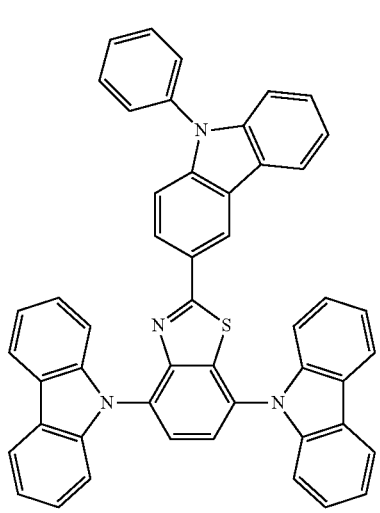 [SMILES: c1ccc(-n2c3ccccc3c3cc(-c4nc5c(-n6c7ccccc7c7ccccc76)ccc(-n6c7ccccc7c7ccccc76)c5s4)ccc32)cc1] |
| 4 | 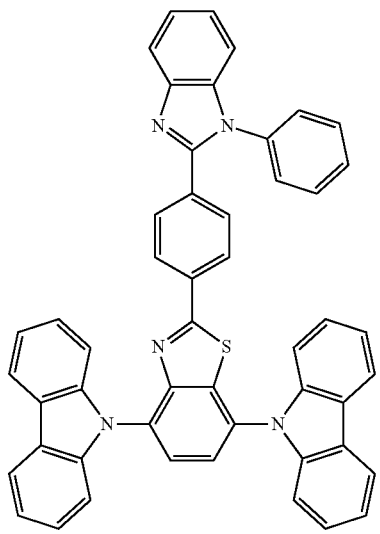 [SMILES: c1ccc(-n2c(-c3ccc(-c4nc5c(-n6c7ccccc7c7ccccc76)ccc(-n6c7ccccc7c7ccccc76)c5s4)cc3)nc3ccccc32)cc1] |

TABLE 12-continued

| No. | Compound |
|---|---|
| 5 | |
| 6 | |
| 7 | |

TABLE 12-continued
| No. | Compound |
|---|---|
| 8 | 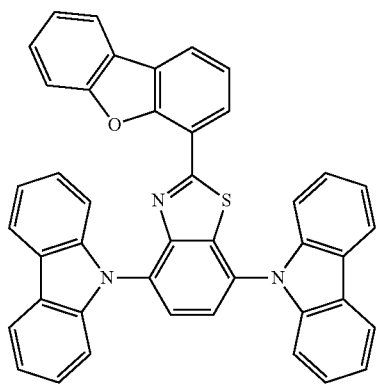 [SMILES: c1ccc2c(c1)oc1c(-c3nc4c(-n5c6ccccc6c6ccccc65)ccc(-n5c6ccccc6c6ccccc65)c4s3)cccc12] |
| 9 | 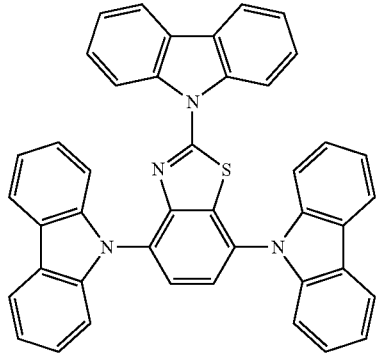 [SMILES: c1ccc2c(c1)c1ccccc1n2-c1nc2c(-n3c4ccccc4c4ccccc43)ccc(-n3c4ccccc4c4ccccc43)c2s1] |
| 10 | 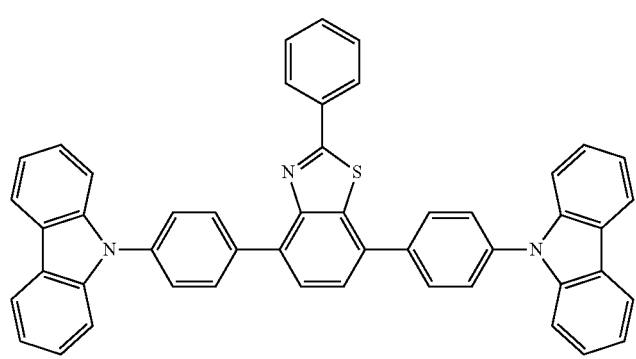 [SMILES: c1ccc(-c2nc3c(-c4ccc(-n5c6ccccc6c6ccccc65)cc4)ccc(-c4ccc(-n5c6ccccc6c6ccccc65)cc4)c3s2)cc1] |
| 11 | 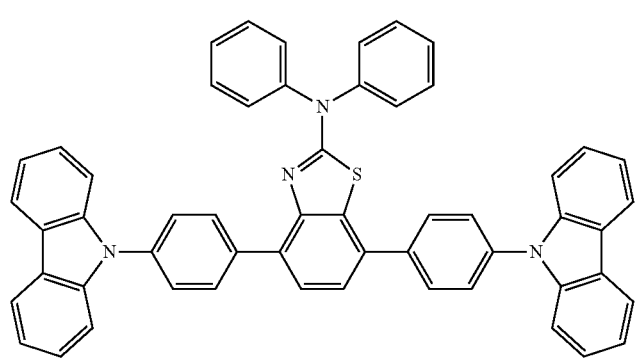 [SMILES: c1ccc(N(c2ccccc2)c2nc3c(-c4ccc(-n5c6ccccc6c6ccccc65)cc4)ccc(-c4ccc(-n5c6ccccc6c6ccccc65)cc4)c3s2)cc1] |

TABLE 12-continued
| No. | Compound |
|---|---|
| 12 | 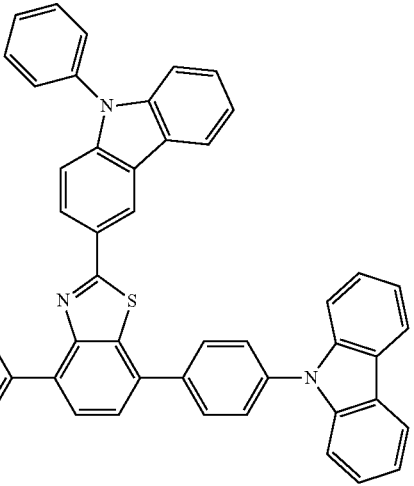 |
| 13 | 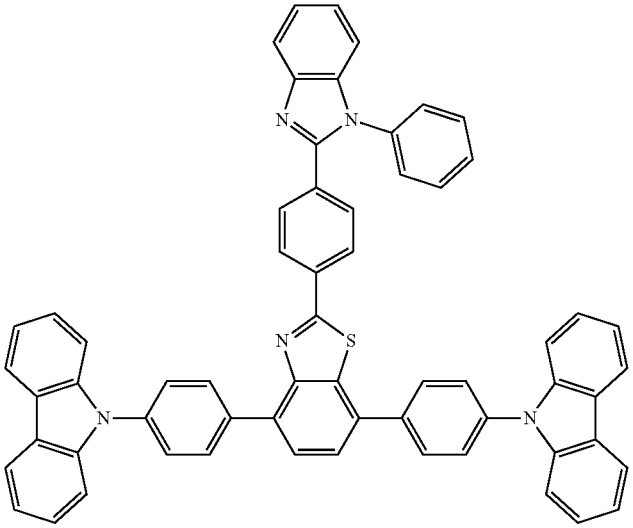 [SMILES: c1ccc(-n2c(-c3ccc(-c4nc5c(-c6ccc(-n7c8ccccc8c8ccccc87)cc6)ccc(-c6ccc(-n7c8ccccc8c8ccccc87)cc6)c5s4)cc3)nc3ccccc32)cc1] |
| 14 | 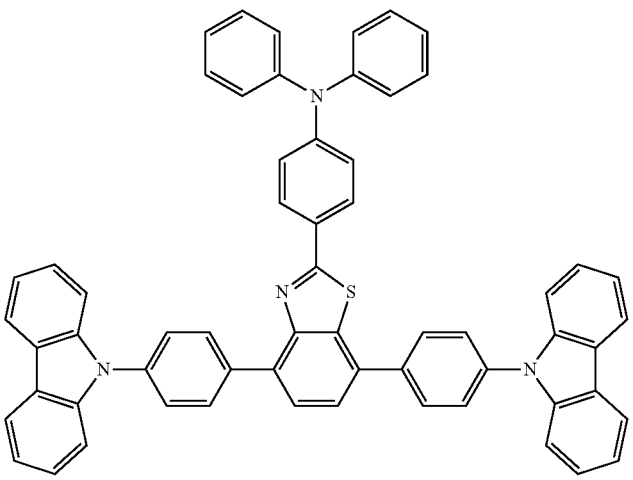 [SMILES: c1ccc(N(c2ccccc2)c2ccc(-c3nc4c(-c5ccc(-n6c7ccccc7c7ccccc76)cc5)ccc(-c5ccc(-n6c7ccccc7c7ccccc76)cc5)c4s3)cc2)cc1] |

TABLE 12-continued
| No. | Compound |
| --- | --- |
| 15 | 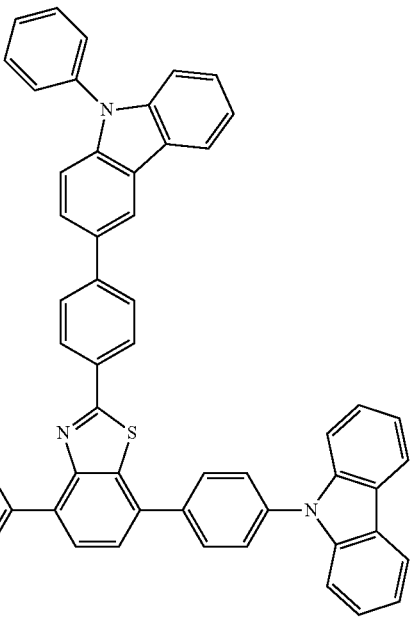 |
| 16 | 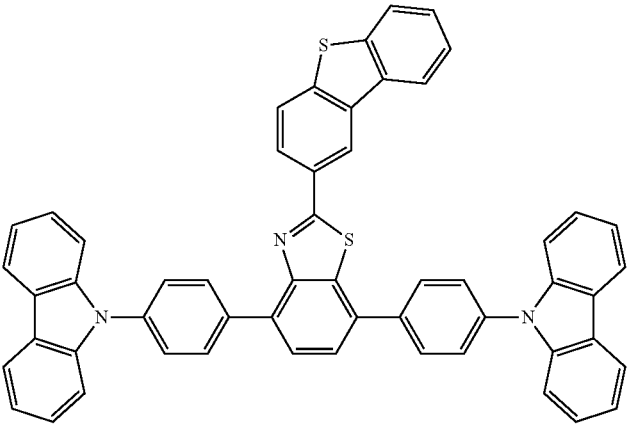 |
| 17 | 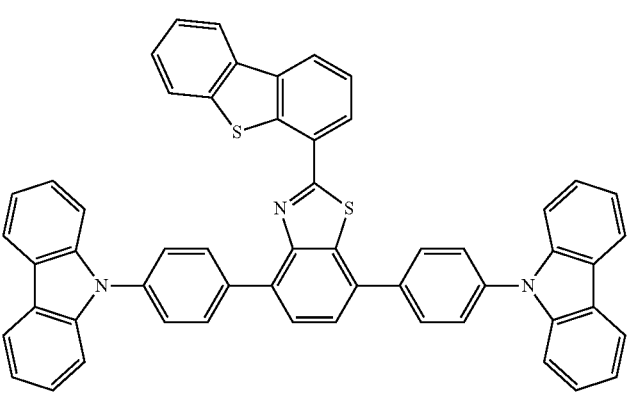 [SMILES: c1ccc2c(c1)sc1c(-c3nc4c(-c5ccc(-n6c7ccccc7c7ccccc76)cc5)ccc(-c5ccc(-n6c7ccccc7c7ccccc76)cc5)c4s3)cccc12] |

TABLE 12-continued
| No. | Compound |
|---|---|
| 18 | 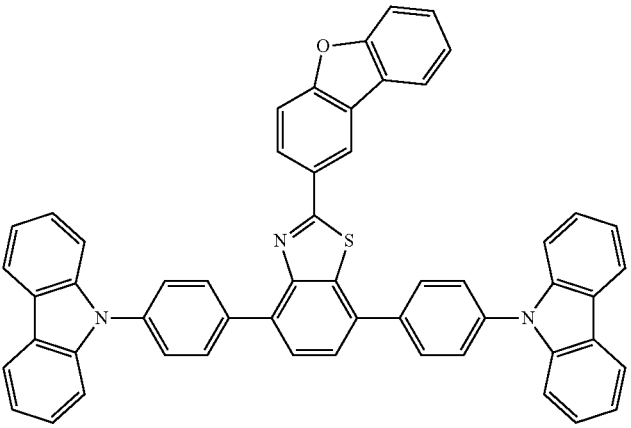 [SMILES: c1ccc2c(c1)oc1ccc(-c3nc4c(-c5ccc(-n6c7ccccc7c7ccccc76)cc5)ccc(-c5ccc(-n6c7ccccc7c7ccccc76)cc5)c4s3)cc12] |
| 19 | 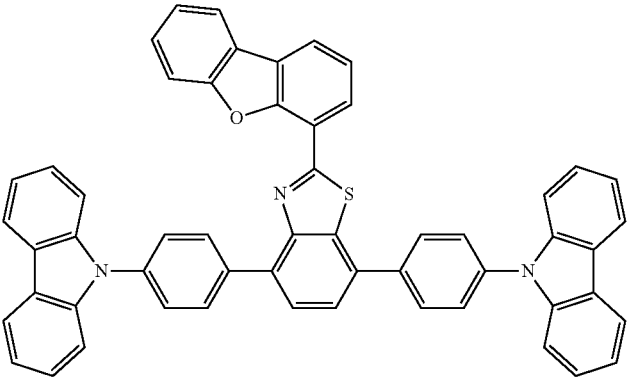 [SMILES: c1ccc2c(c1)oc1c(-c3nc4c(-c5ccc(-n6c7ccccc7c7ccccc76)cc5)ccc(-c5ccc(-n6c7ccccc7c7ccccc76)cc5)c4s3)cccc12] |
| 20 | 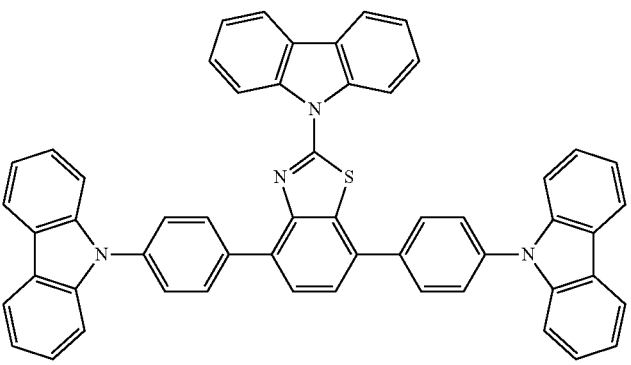 [SMILES: c1ccc2c(c1)c1ccccc1n2-c1ccc(-c2ccc(-c3ccc(-n4c5ccccc5c5ccccc54)cc3)c3sc(-n4c5ccccc5c5ccccc54)nc23)cc1] |

TABLE 12-continued
| No. | Compound |
|---|---|
| 21 | 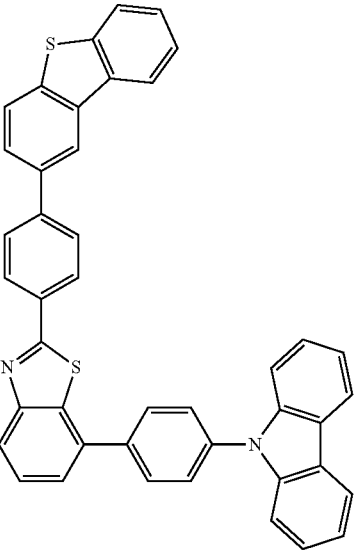 |
| 22 | 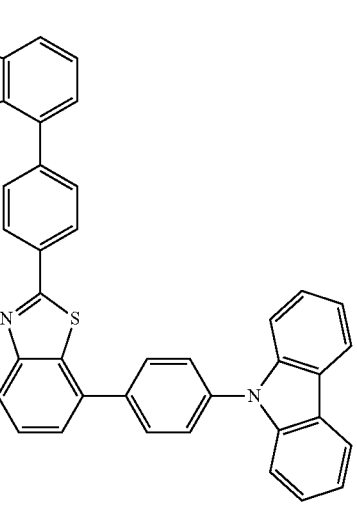 |
| 23 | 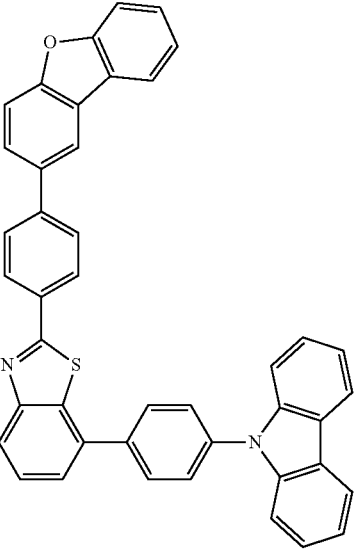 |

TABLE 12-continued
| No. | Compound |
|---|---|
| 24 | 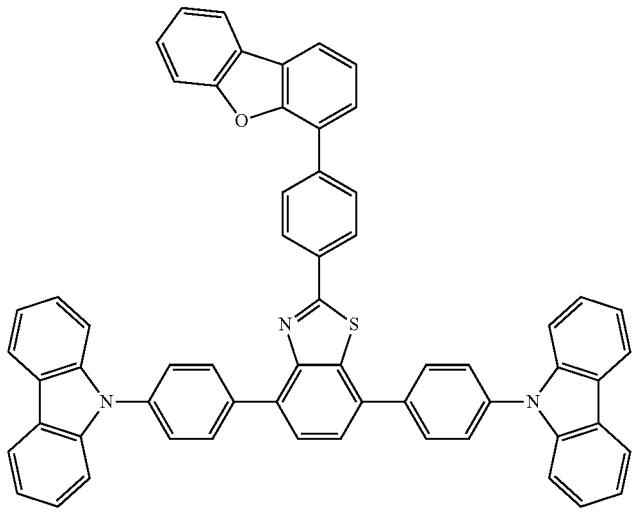 [SMILES: c1ccc2c(c1)oc1c(-c3ccc(-c4nc5c(-c6ccc(-n7c8ccccc8c8ccccc87)cc6)ccc(-c6ccc(-n7c8ccccc8c8ccccc87)cc6)c5s4)cc3)cccc12] |
| 25 | 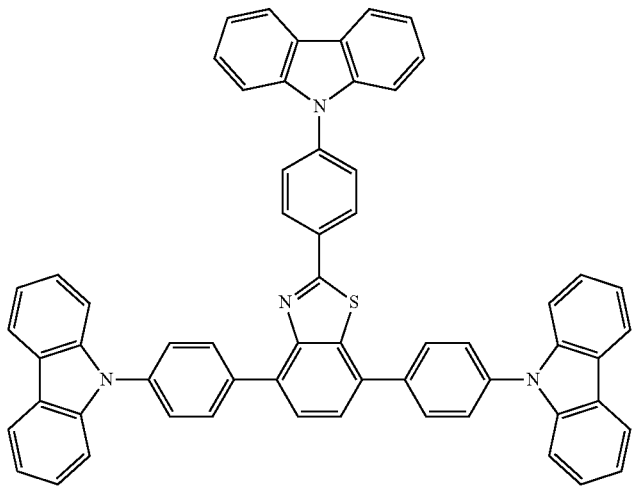 [SMILES: c1ccc2c(c1)c1ccccc1n2-c1ccc(-c2nc3c(-c4ccc(-n5c6ccccc6c6ccccc65)cc4)ccc(-c4ccc(-n5c6ccccc6c6ccccc65)cc4)c3s2)cc1] |

TABLE 12-continued

| No. | Compound |
|---|---|
| 26 | 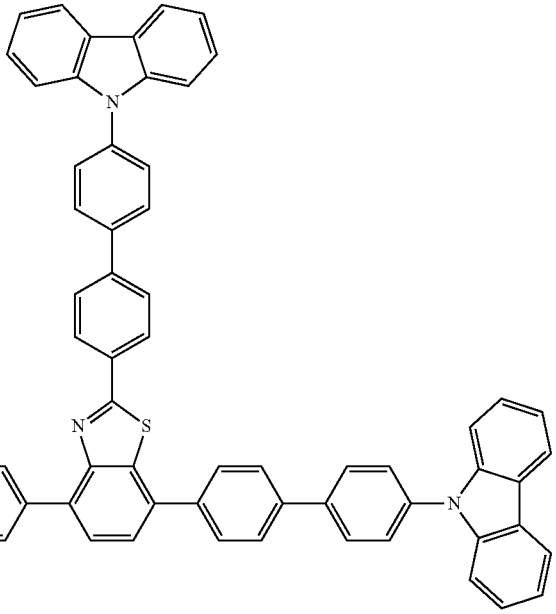 |

In one exemplary embodiment, the compound according to the present invention may include a compound in which $Z_1$ and $Z_2$ in Formula 1 each independently have the structure of Formula 5.

For example, $Z_3$ in Formula 1 may be selected from the structures of the following Table 13.

TABLE 13

| No. | Substituent structure |
|---|---|
| 1 | 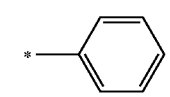 |
| 2 | 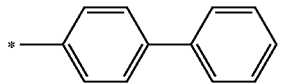 |
| 3 | 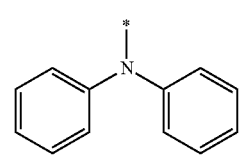 [SMILES: *N(c1ccccc1)c1ccccc1] |
| 4 | 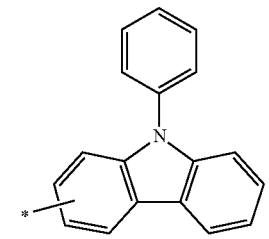 |

TABLE 13-continued

| No. | Substituent structure |
|---|---|
| 5 | 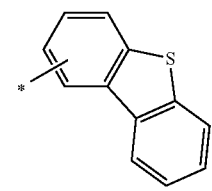 |
| 6 | 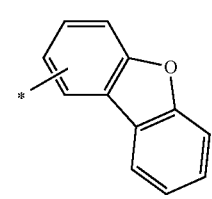 |
| 7 | 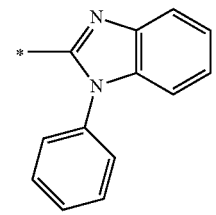 [SMILES: Cc1nc2ccccc2n1-c1ccccc1] |
| 8 | 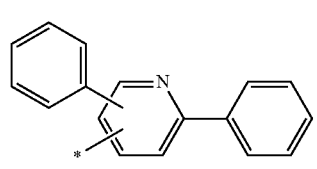 |

TABLE 13-continued

| No. | Substituent structure |
|---|---|
| 9 |  |

In this case, $Z_1$ and $Z_2$ in Formula 1 may be each independently selected from the structure of the following Table 14.

TABLE 14

| No. | Substituent structure |
|---|---|
| 1 | 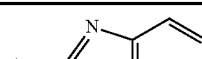 |

In addition, $L_a$, $L_b$, and $L_c$ in Formula 1 may be each independently selected from a single bond or the structures of the following Table 15.

TABLE 15

| No. | Substituent structure |
|---|---|
| 1 | 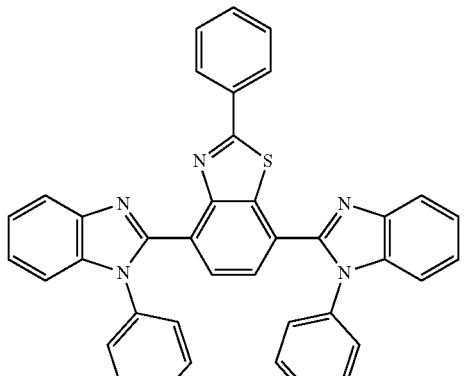 |
| 2 | 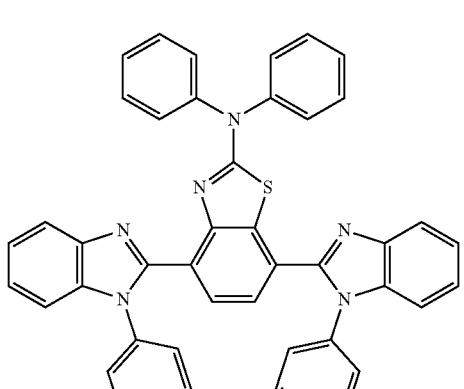 |

More specifically, the compound represented by Formula 1 may be selected from the structures of the following Table 16.

TABLE 16

| No. | Compound |
|---|---|
| 1 |  |
| 2 |  |

TABLE 16-continued
| No. | Compound |
|---|---|
| 3 | 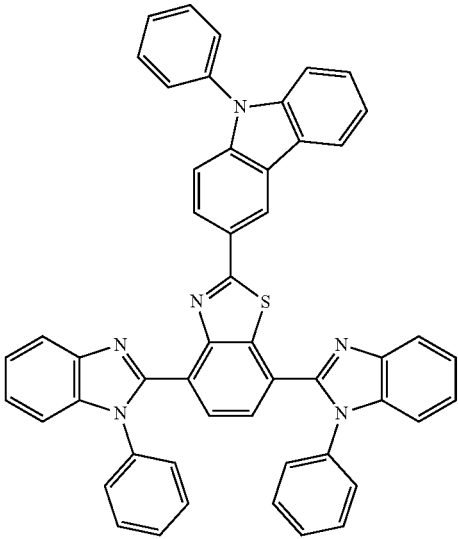 [SMILES: c1ccc(-n2c(-c3ccc(-c4nc5ccccc5n4-c4ccccc4)c4sc(-c5ccc6c(c5)c5ccccc5n6-c5ccccc5)nc34)nc3ccccc32)cc1] |
| 4 | 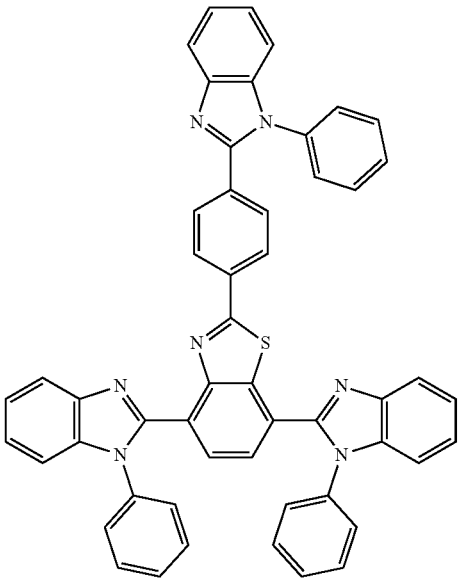 [SMILES: c1ccc(-n2c(-c3ccc(-c4nc5c(-c6nc7ccccc7n6-c6ccccc6)ccc(-c6nc7ccccc7n6-c6ccccc6)c5s4)cc3)nc3ccccc32)cc1] |
| 5 | 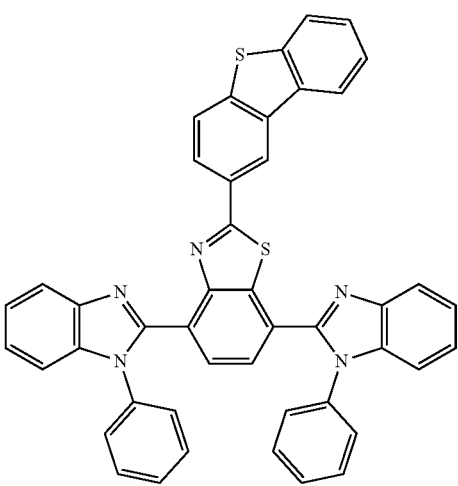 [SMILES: c1ccc(-n2c(-c3ccc(-c4nc5ccccc5n4-c4ccccc4)c4sc(-c5ccc6sc7ccccc7c6c5)nc34)nc3ccccc32)cc1] |

TABLE 16-continued
| No. | Compound |
|---|---|
| 6 | 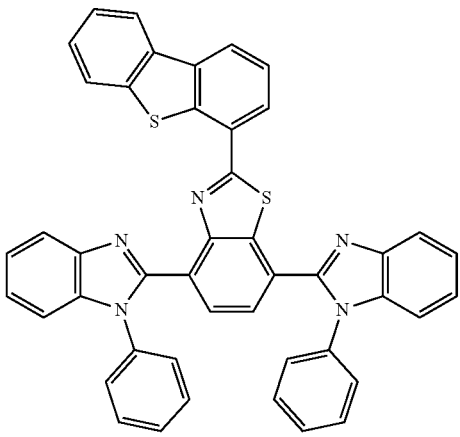 [SMILES: c1ccc(-n2c(-c3ccc(-c4nc5ccccc5n4-c4ccccc4)c4sc(-c5cccc6c5sc5ccccc56)nc34)nc3ccccc32)cc1] |
| 7 | 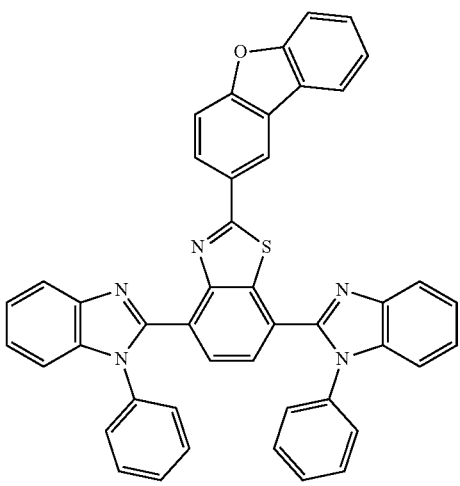 [SMILES: c1ccc(-n2c(-c3ccc(-c4nc5ccccc5n4-c4ccccc4)c4sc(-c5ccc6oc7ccccc7c6c5)nc34)nc3ccccc32)cc1] |
| 8 | 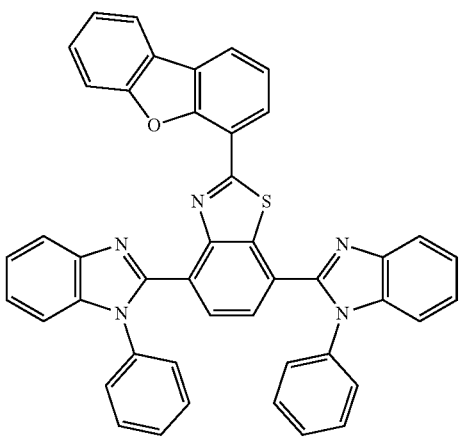 [SMILES: c1ccc(-n2c(-c3ccc(-c4nc5ccccc5n4-c4ccccc4)c4sc(-c5cccc6c5oc5ccccc56)nc34)nc3ccccc32)cc1] |

TABLE 16-continued
| No. | Compound |
| --- | --- |
| 9 | 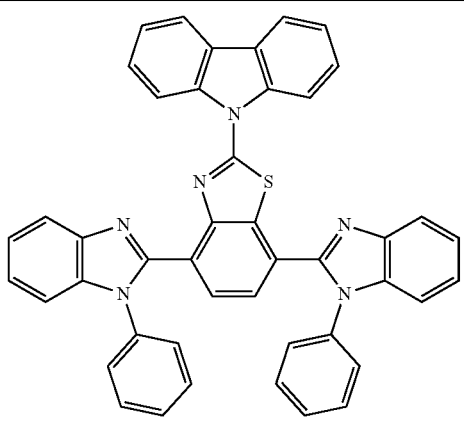 |
| 10 | 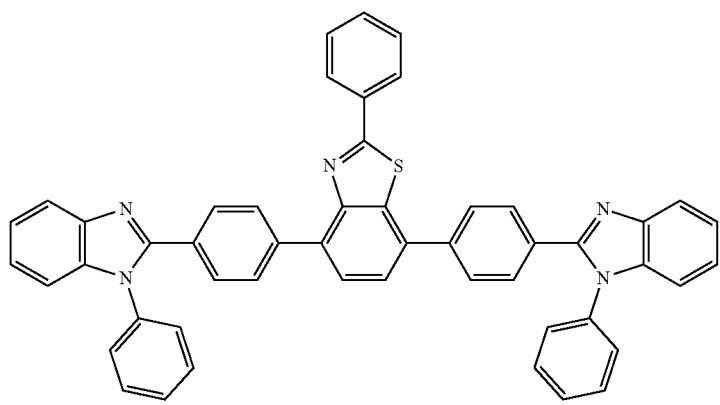 [SMILES: c1ccc(-c2nc3c(-c4ccc(-c5nc6ccccc6n5-c5ccccc5)cc4)ccc(-c4ccc(-c5nc6ccccc6n5-c5ccccc5)cc4)c3s2)cc1] |
| 11 | 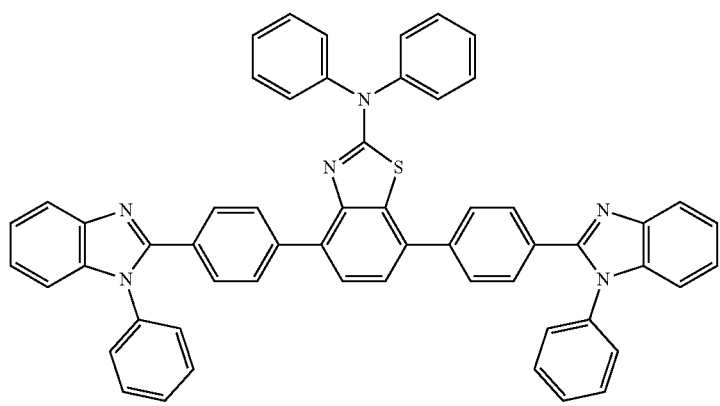 [SMILES: c1ccc(N(c2ccccc2)c2nc3c(-c4ccc(-c5nc6ccccc6n5-c5ccccc5)cc4)ccc(-c4ccc(-c5nc6ccccc6n5-c5ccccc5)cc4)c3s2)cc1] |

TABLE 16-continued
| No. | Compound |
|---|---|
| 12 | 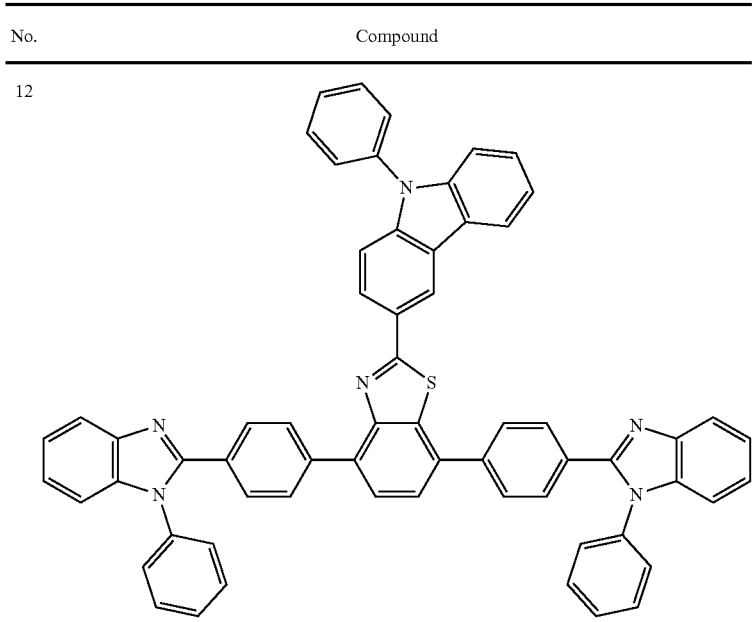 |
| 13 | |

TABLE 16-continued
| No. | Compound |
|---|---|
| 14 | 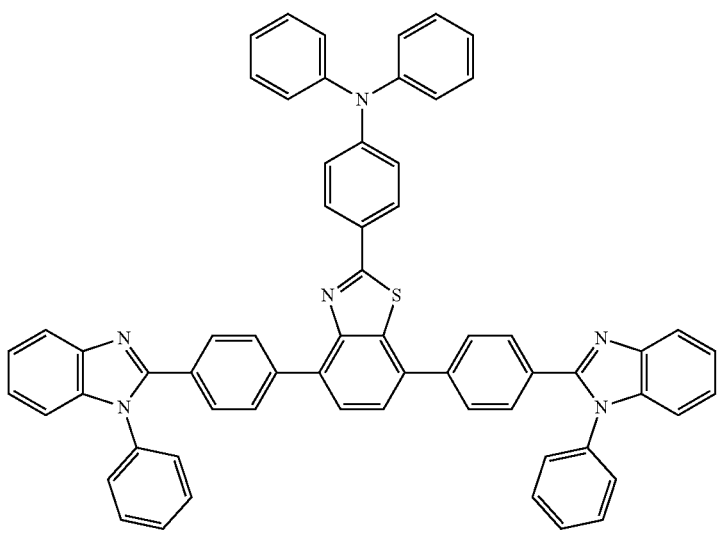 [SMILES: c1ccc(N(c2ccccc2)c2ccc(-c3nc4c(-c5ccc(-c6nc7ccccc7n6-c6ccccc6)cc5)ccc(-c5ccc(-c6nc7ccccc7n6-c6ccccc6)cc5)c4s3)cc2)cc1] |
| 15 | 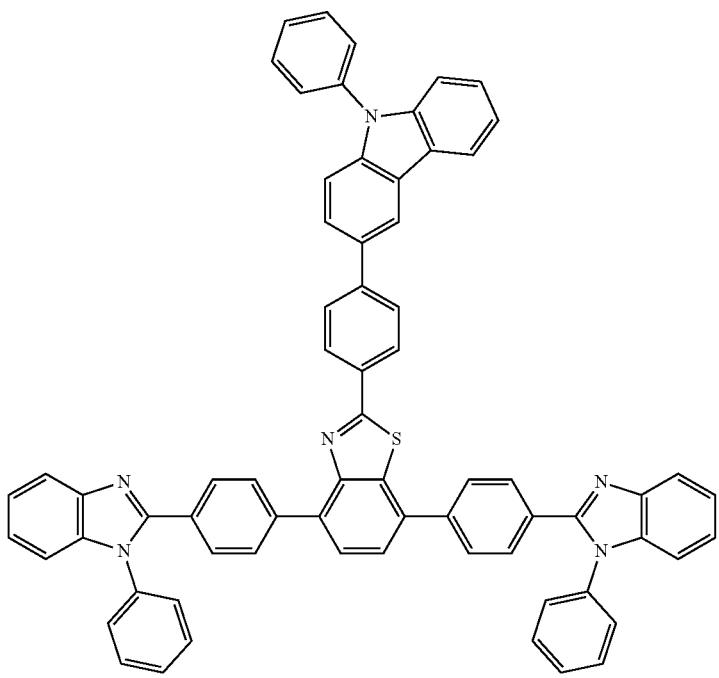 [SMILES: c1ccc(-n2c(-c3ccc(-c4ccc(-c5ccc(-c6nc7ccccc7n6-c6ccccc6)cc5)c5sc(-c6ccc(-c7ccc8c(c7)c7ccccc7n8-c7ccccc7)cc6)nc45)cc3)nc3ccccc32)cc1] |

TABLE 16-continued

| No. | Compound |
|-----|----------|
| 16  |          |
| 17  |          |
| 18  |          |

TABLE 16-continued
| No. | Compound |
|---|---|
| 19 | 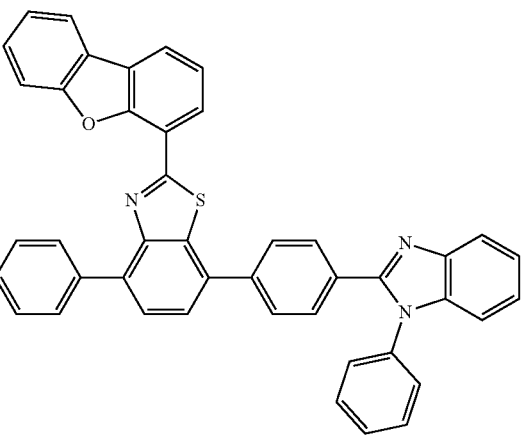 |
| 20 | 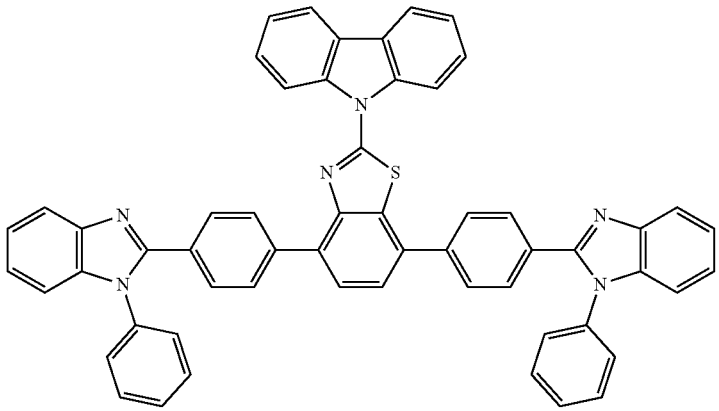 [SMILES: c1ccc(-n2c(-c3ccc(-c4ccc(-c5ccc(-c6nc7ccccc7n6-c6ccccc6)cc5)c5sc(-n6c7ccccc7c7ccccc76)nc45)cc3)nc3ccccc32)cc1] |
| 21 | 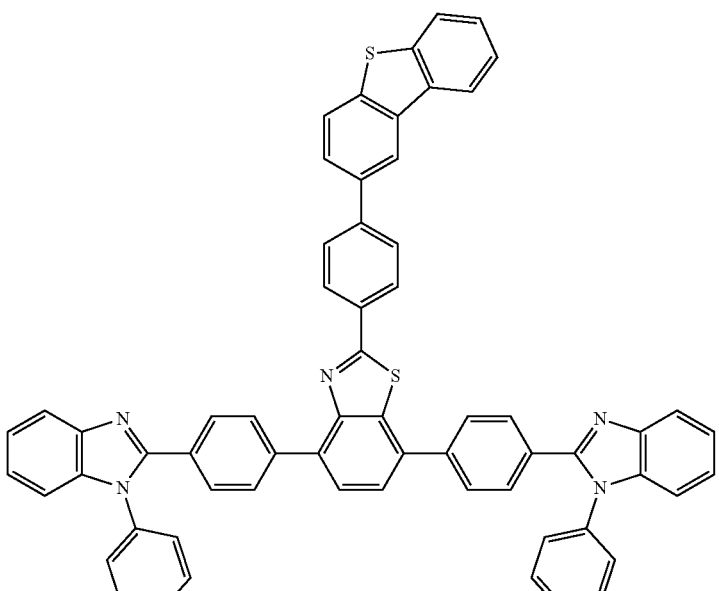 |

TABLE 16-continued
| No. | Compound |
|---|---|
| 22 | 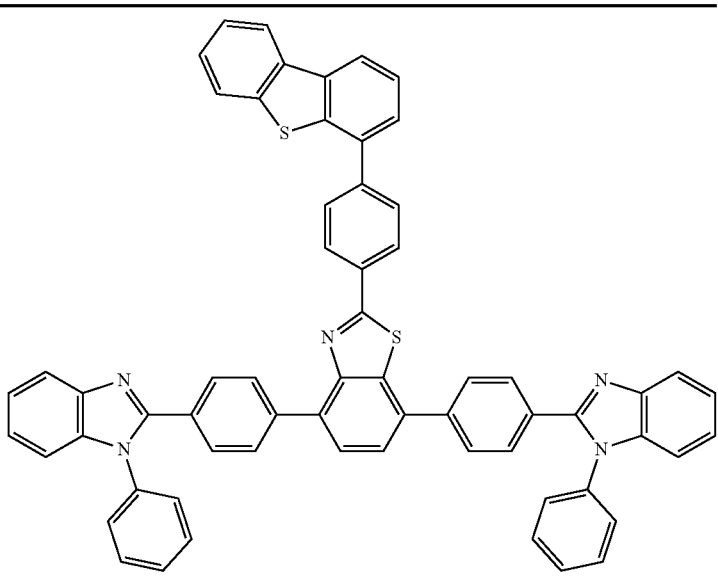 |
| 23 | 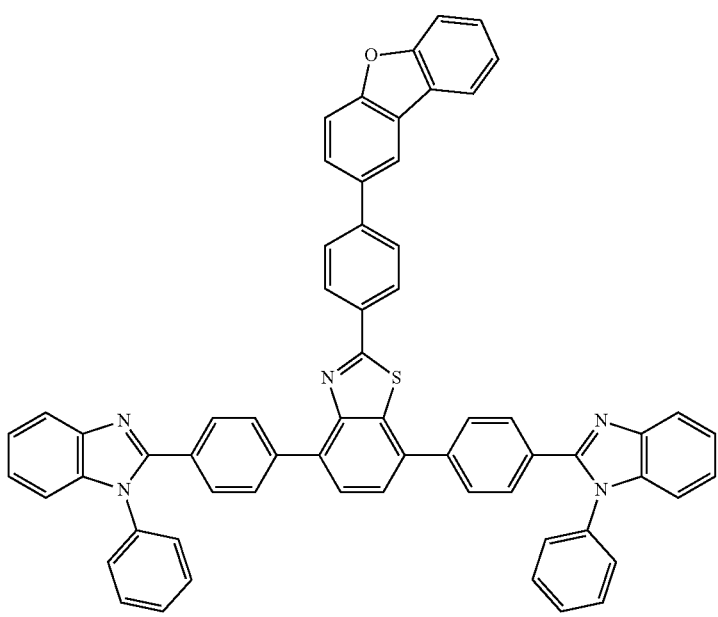 [SMILES: c1ccc(-n2c(-c3ccc(-c4ccc(-c5ccc(-c6nc7ccccc7n6-c6ccccc6)cc5)c5sc(-c6ccc(-c7ccc8oc9ccccc9c8c7)cc6)nc45)cc3)nc3ccccc32)cc1] |

TABLE 16-continued

| No. | Compound |
|---|---|
| 24 |  |
| 25 |  |

In one exemplary embodiment, the compound according to the present invention may include a compound in which $Z_1$ and $Z_2$ in Formula 1 each independently have the structure of Formula 6.

For example, $Z_3$ in Formula 1 may be selected from the structures of the following Table 17.

TABLE 17

| No. | Substituent structure |
|---|---|
| 1 |  |

TABLE 17-continued

| No. | Substituent structure |
|---|---|
| 2 |  |
| 3 |  |

TABLE 17-continued

| No. | Substituent structure |
|---|---|
| 4 | 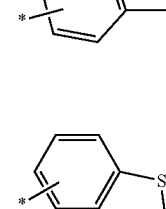 |
| 5 | 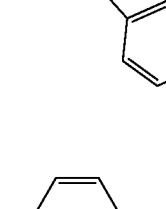 |
| 6 | 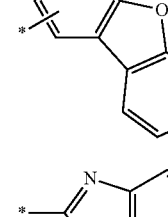 |
| 7 | 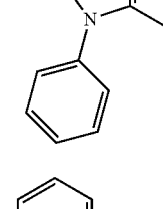 |
| 8 | 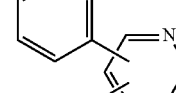 |
| 9 |  |

In this case, $Z_1$ and $Z_2$ in Formula 1 may be each independently selected from the structure of the following Table 18.

TABLE 18

| No. | Substituent structure |
|---|---|
| 1 |  |

Furthermore, $L_a$, $L_b$, and $L_c$ in Formula 1 may be each independently selected from a single bond or the structures of the following Table 19.

TABLE 19

| No. | Substituent structure |
|---|---|
| 1 | *—⌬—* |
| 2 | *—⌬—⌬—* |

More specifically, the compound represented by Formula 1 may be selected from the structures of the following Table 20.

TABLE 20

| No. | Compound |
|---|---|
| 1 | |

TABLE 20-continued
| No. | Compound |
|---|---|
| 2 | 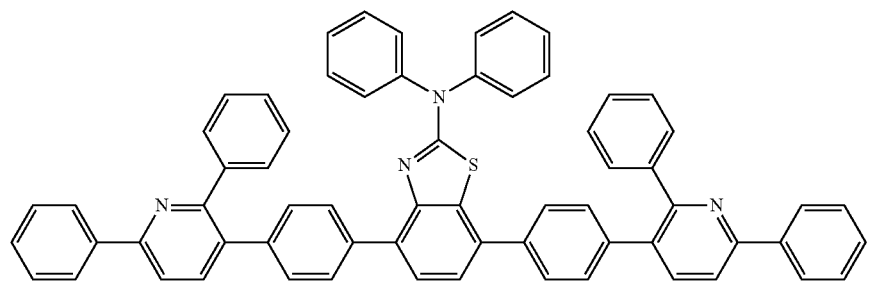 [SMILES: c1ccc(-c2ccc(-c3ccc(-c4ccc(-c5ccc(-c6ccc(-c7ccccc7)nc6-c6ccccc6)cc5)c5sc(N(c6ccccc6)c6ccccc6)nc45)cc3)c(-c3ccccc3)n2)cc1] |
| 3 | 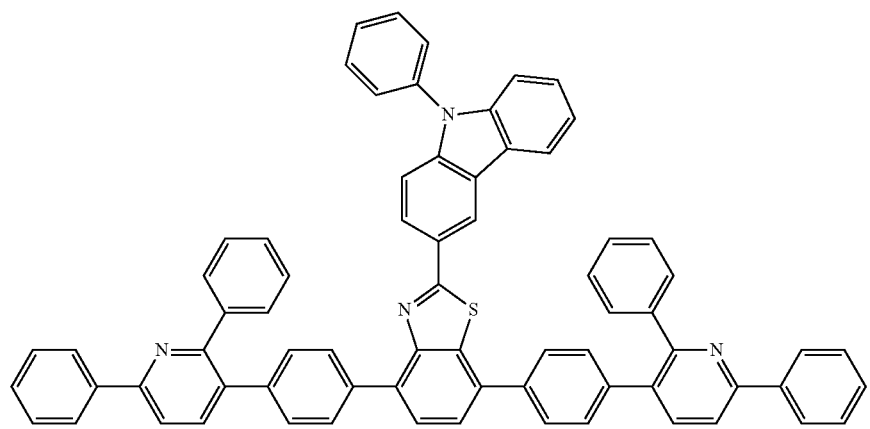 [SMILES: c1ccc(-c2ccc(-c3ccc(-c4ccc(-c5ccc(-c6ccc(-c7ccccc7)nc6-c6ccccc6)cc5)c5sc(-c6ccc7c(c6)c6ccccc6n7-c6ccccc6)nc45)cc3)c(-c3ccccc3)n2)cc1] |
| 4 | 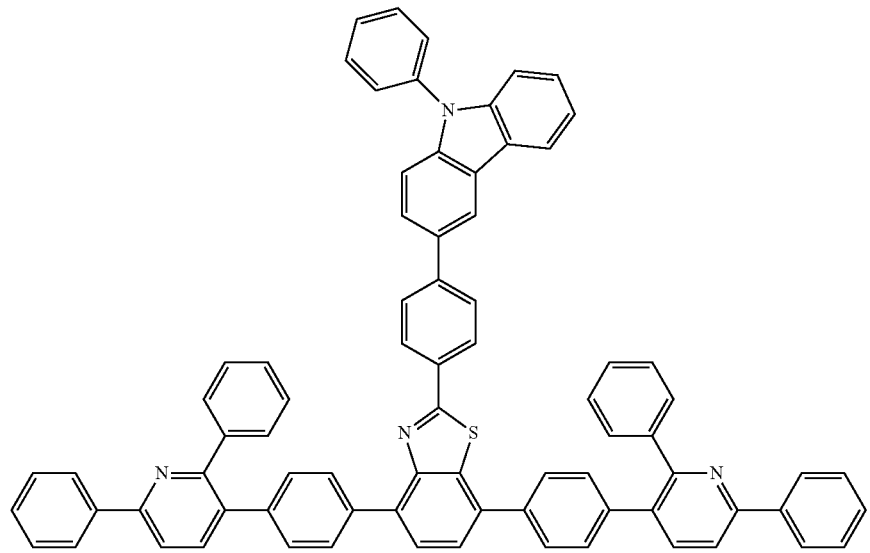 [SMILES: c1ccc(-c2ccc(-c3ccc(-c4ccc(-c5ccc(-c6ccc(-c7ccccc7)nc6-c6ccccc6)cc5)c5sc(-c6ccc(-c7ccc8c(c7)c7ccccc7n8-c7ccccc7)cc6)nc45)cc3)c(-c3ccccc3)n2)cc1] |

TABLE 20-continued
| No. | Compound |
| --- | --- |
| 5 | 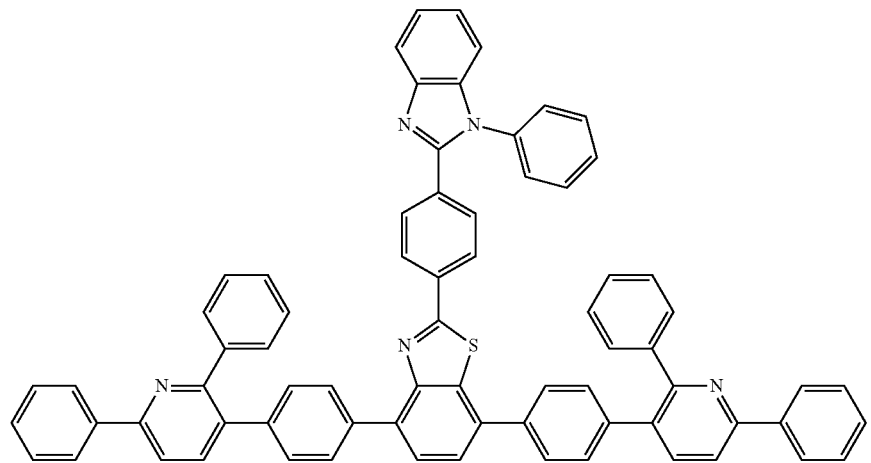 [SMILES: c1ccc(-c2ccc(-c3ccc(-c4ccc(-c5ccc(-c6ccc(-c7ccccc7)nc6-c6ccccc6)cc5)c5sc(-c6ccc(-c7nc8ccccc8n7-c7ccccc7)cc6)nc45)cc3)c(-c3ccccc3)n2)cc1] |
| 6 | 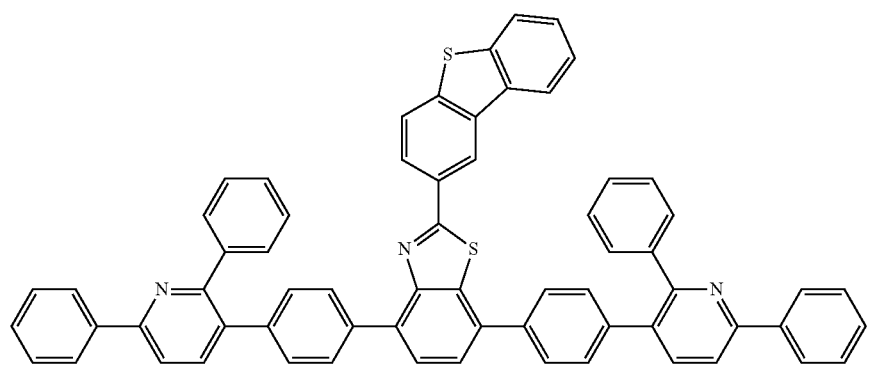 [SMILES: c1ccc(-c2ccc(-c3ccc(-c4ccc(-c5ccc(-c6ccc(-c7ccccc7)nc6-c6ccccc6)cc5)c5sc(-c6ccc7sc8ccccc8c7c6)nc45)cc3)c(-c3ccccc3)n2)cc1] |
| 7 | 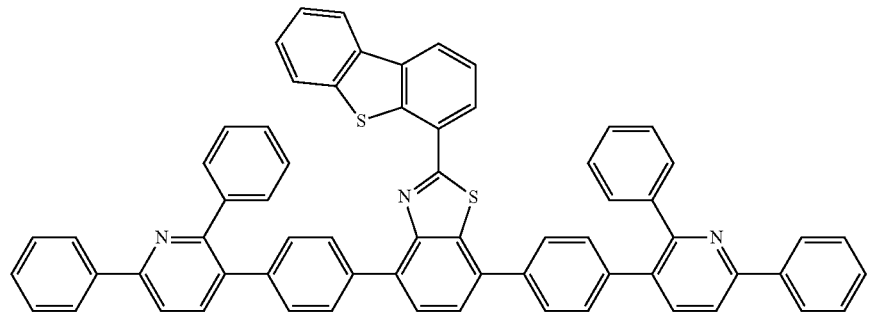 |

TABLE 20-continued
| No. | Compound |
|---|---|
| 8 | 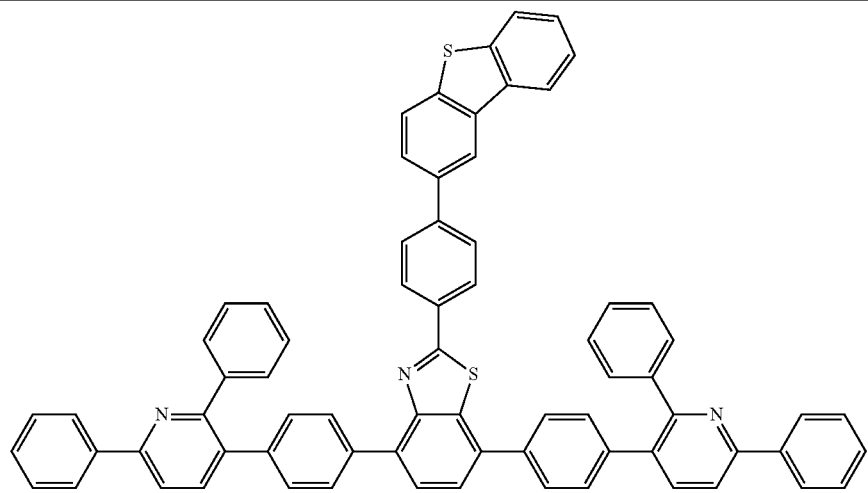 |
| 9 | 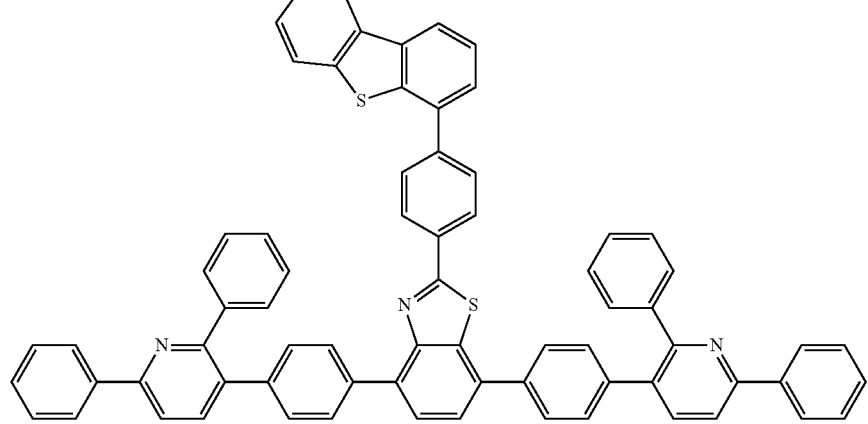 |
| 10 | 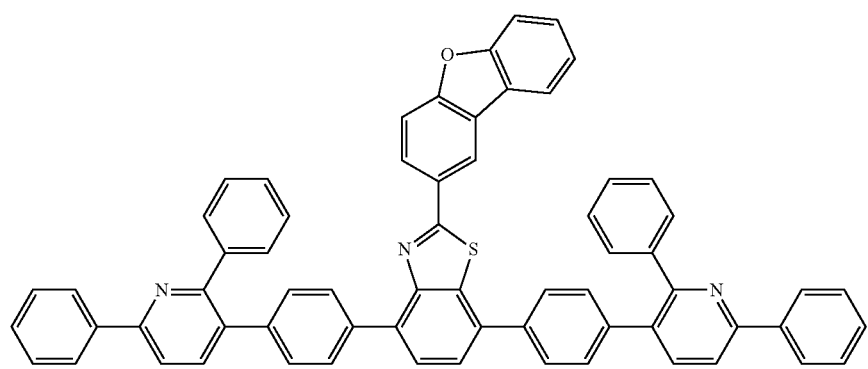 [SMILES: c1ccc(-c2ccc(-c3ccc(-c4ccc(-c5ccc(-c6ccc(-c7ccccc7)nc6-c6ccccc6)cc5)c5sc(-c6ccc7oc8ccccc8c7c6)nc45)cc3)c(-c3ccccc3)n2)cc1] |
| 11 | 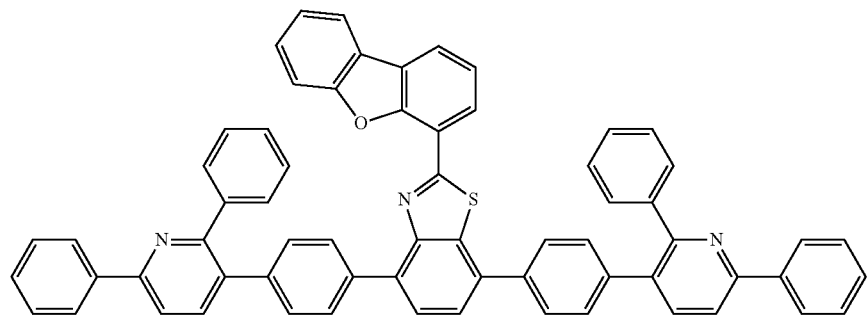 [SMILES: c1ccc(-c2ccc(-c3ccc(-c4ccc(-c5ccc(-c6ccc(-c7ccccc7)nc6-c6ccccc6)cc5)c5sc(-c6cccc7c6oc6ccccc67)nc45)cc3)c(-c3ccccc3)n2)cc1] |

TABLE 20-continued
| No. | Compound |
|---|---|
| 12 | 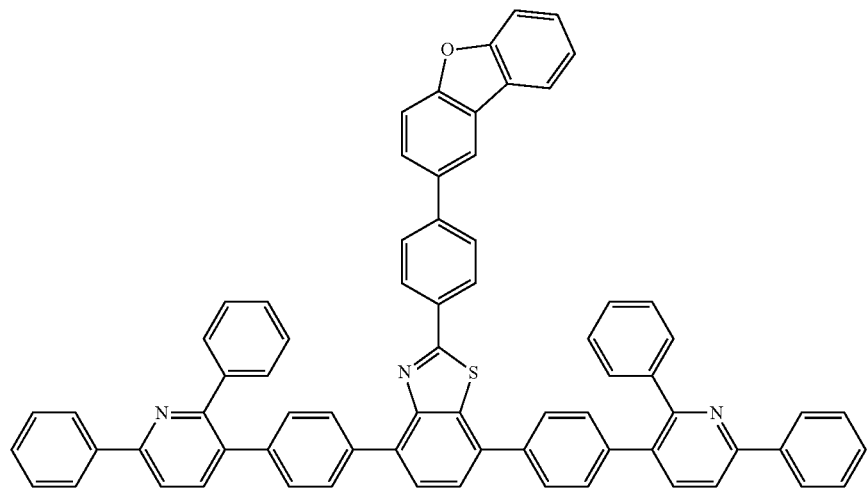 [SMILES: c1ccc(-c2ccc(-c3ccc(-c4ccc(-c5ccc(-c6ccc(-c7ccccc7)nc6-c6ccccc6)cc5)c5sc(-c6ccc(-c7ccc8oc9ccccc9c8c7)cc6)nc45)cc3)c(-c3ccccc3)n2)cc1] |
| 13 | 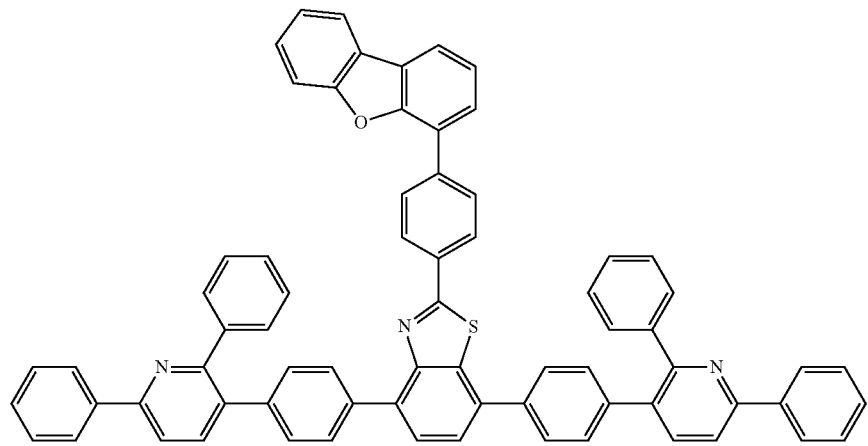 [SMILES: c1ccc(-c2ccc(-c3ccc(-c4ccc(-c5ccc(-c6ccc(-c7ccccc7)nc6-c6ccccc6)cc5)c5sc(-c6ccc(-c7cccc8c7oc7ccccc78)cc6)nc45)cc3)c(-c3ccccc3)n2)cc1] |
| 14 | 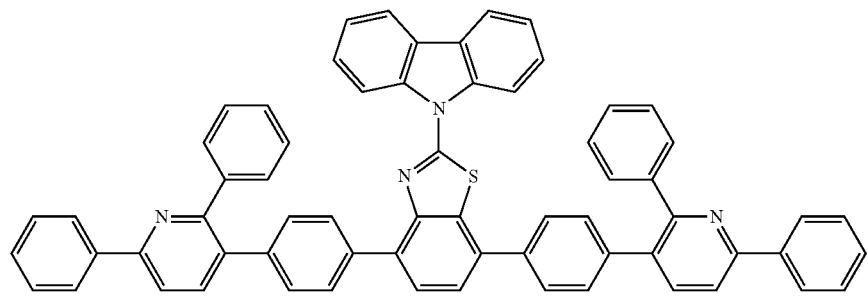 [SMILES: c1ccc(-c2ccc(-c3ccc(-c4ccc(-c5ccc(-c6ccc(-c7ccccc7)nc6-c6ccccc6)cc5)c5sc(-n6c7ccccc7c7ccccc76)nc45)cc3)c(-c3ccccc3)n2)cc1] |

TABLE 20-continued

| No. | Compound |
|---|---|
| 15 | 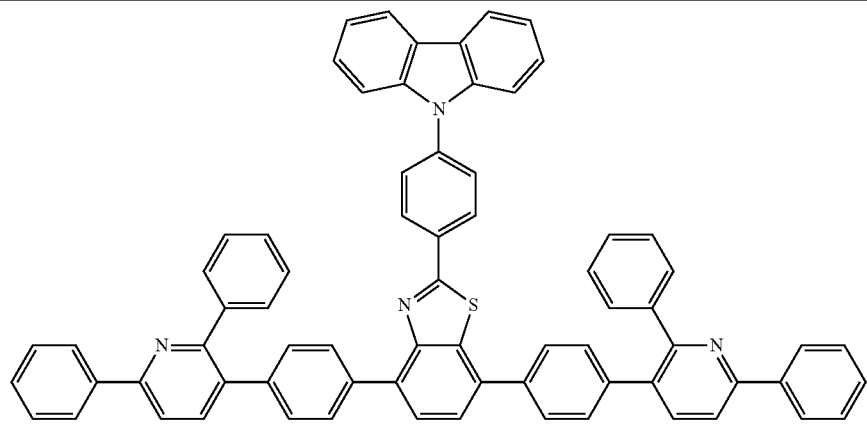 |
| 16 | 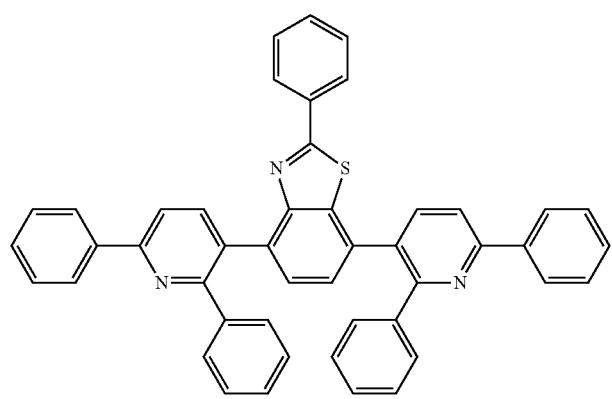 [SMILES: c1ccc(-c2ccc(-c3ccc(-c4ccc(-c5ccccc5)nc4-c4ccccc4)c4sc(-c5ccccc5)nc34)c(-c3ccccc3)n2)cc1] |
| 17 | 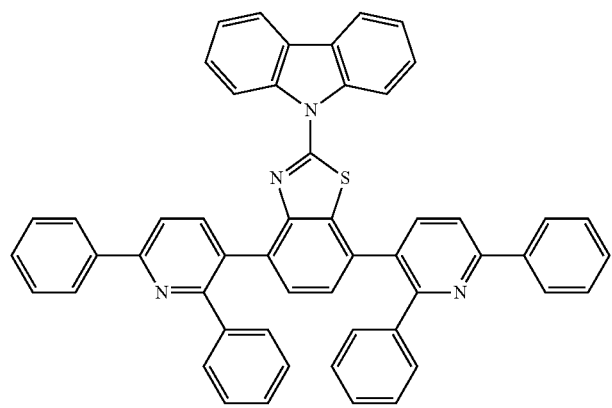 [SMILES: c1ccc(-c2ccc(-c3ccc(-c4ccc(-c5ccccc5)nc4-c4ccccc4)c4sc(-n5c6ccccc6c6ccccc65)nc34)c(-c3ccccc3)n2)cc1] |

The present invention provides a light-emitting element including the compound previously described.

The compounds according to the present invention may be included in any one layer of a hole transporting layer, an electron transporting layer, and a light-emitting layer of a light-emitting element.

In an exemplary embodiment, the light-emitting element may include: a first electrode; a second electrode; a light-emitting layer disposed between the first electrode and the second electrode; and a hole transporting layer disposed between the first electrode and the light-emitting layer, and the hole transporting layer may include the compound according to the present invention.

Further, the hole transporting layer may further include a p-type dopant, and the kind of p-type dopant is not particularly limited.

For example, the hole transporting layer may include a first layer including the compound according to the present invention and a p-type dopant, and a second layer including the compound according to the present invention. Among the compounds according to the present invention, the compound included in the first layer may be the same as or different from the compound included in the second layer.

In an exemplary embodiment, the light-emitting element may include: a first electrode; a second electrode; a light-emitting layer disposed between the first electrode and the second electrode; and an electron transporting layer disposed between the second electrode and the light-emitting layer, and the electron transporting layer may include the compound according to the present invention.

In addition, the electron transporting layer may further include an N-type dopant, and the kind of N-type dopant is not particularly limited.

For example, the electron transporting layer may include: a first layer including the compound according to the present invention and an N-type dopant; and a second layer including the compound according to the present invention. Among the compounds according to the present invention, the compound included in the first layer may be the same as or different from the compound included in the second layer.

When the light-emitting element includes a hole transporting layer disposed between the first electrode and the light-emitting layer together with an electron transporting layer, the hole transporting layer may also include the compound according to the present invention, that is, the compound represented by Formula 1. In this case, the compound included in the hole transporting layer is represented by Formula 1, but may be different from the compound included in the electron transporting layer.

In an exemplary embodiment, the light-emitting element may include: a first electrode; a second electrode; and a light-emitting layer disposed between the first electrode and the second electrode, and the light-emitting layer may include the compound according to the present invention. Furthermore, the light-emitting layer may further include a dopant, and the kind of dopant to be doped in the light-emitting layer is not particularly limited. When the light-emitting element further includes a hole transporting layer disposed between the first electrode and the light-emitting layer and/or an electron transporting layer disposed between the second electrode and the light-emitting layer, the hole transporting layer and/or the electron transporting layer may include the compound according to the present invention, that is, the compound represented by Formula 1. In this case, the compound included in the hole transporting layer or the electron transporting layer is represented by Formula 1, but may be different from the compound included in the light-emitting layer.

Hereinafter, a light-emitting element including the novel compound according to the present invention will be described with reference to the accompanying drawings. The structure of the light-emitting element including the compound is not limited by the accompanying drawings and the following description.

FIG. 1 is a cross-sectional view for describing a light-emitting element according to an exemplary embodiment of the present invention.

Referring to FIG. 1, a light-emitting element 100 includes a first electrode A1, a hole transporting layer 20, a light-emitting layer 30, and a second electrode A2, which are formed on a base substrate 10. The light-emitting element 100 may be an organic light emitting diode (OLED).

The first electrode A1 may be formed of a conductive material on the base substrate 10. As an example, the first electrode A1 may be a transparent electrode. In this case, the first electrode A1 may be formed of indium tin oxide (ITO). In contrast, the first electrode A1 may be an opaque (reflective) electrode. In this case, the first electrode A1 may have an ITO/silver (Ag)/ITO structure. The first electrode A1 may become an anode of the light-emitting element 100.

The hole transporting layer 20 is formed on the first electrode A1 to be interposed between the first electrode A1 and the light-emitting layer 30. The hole transporting layer 20 includes a compound represented by the following Formula 1 as a hole transport compound.

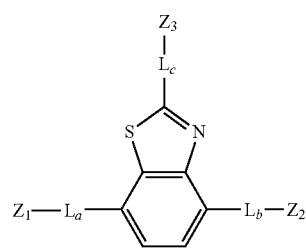

<Formula 1>

The compound represented by Formula 1 is a novel compound according to the present invention and is substantially the same as those described above. Accordingly, the specific description of each of $Z_1$, $Z_2$, $Z_3$, $L_a$, $L_b$, and $L_c$ will be omitted.

The wavelength of light which the light-emitting layer 30 emits may vary according to the kind of compound which forms the light-emitting layer 30.

The second electrode A2 may be formed of a conductive material on the light-emitting layer 30. When the first electrode A1 is a transparent electrode, the second electrode A2 may be an opaque (reflective) electrode. In this case, the second electrode A2 may be an aluminum electrode. In contrast, when the first electrode A1 is an opaque electrode, the second electrode A2 may be a transparent or s electrode. In this case, the second electrode A2 may have a thickness of 100 Å to 150 Å, and may be an alloy including magnesium and silver. The second electrode A2 may become a cathode of the light-emitting element 100.

Between the light-emitting layer 30 and the second electrode A2, an electron transporting layer and/or an electron injecting layer may be formed as an electron transporting layer.

When current flows between the first and second electrodes A1 and A2 of the light-emitting element 100, a hole injected from the first electrode A1 to the light-emitting layer 30 and an electron injected from the second electrode A2 to the light-emitting layer 30 combine with each other to form an exciton. While the exciton is transferred to a bottom state, light having a wavelength at a specific band is produced. In this case, the exciton may be a singlet exciton, and may also be a triplet exciton. Accordingly, the light-emitting element 100 may provide light to the outside.

Even though not illustrated in the drawing, the light-emitting element 100 may further include an electron transporting layer (ETL) and an electron injecting layer (EIL), which are disposed between the light-emitting layer 30 and the second electrode A2. The electron transporting layer and the electron injecting layer may be sequentially stacked and formed on the light-emitting layer 30.

Further, the light-emitting element 100 may further include a first blocking layer (not illustrated) disposed between the first electrode A1 and the light-emitting layer 30 and/or a second blocking layer (not illustrated) disposed between the light-emitting layer 30 and the second electrode A2.

For example, the first blocking layer may be an electron blocking layer (EBL) which is disposed between the hole transporting layer 20 and the light-emitting layer 30 and thus prevents electrons injected from the second electrode A2 from flowing into the hole transporting layer 20 via the light-emitting layer 30. Furthermore, the first blocking layer may be an exciton blocking layer which prevents an exciton formed in the light-emitting layer 30 from being diffused in a direction of the first electrode A1 and thus being non-radiatively decayed.

In this case, the first blocking layer may include the compound according to the present invention, which is described above.

The second blocking layer may be a hole blocking layer (HBL) which is disposed between the light-emitting layer 30 and the second electrode A2, specifically, the light-emitting layer 30 and the electron transporting layer, and thus prevents holes from flowing into the electron transporting layer via the light-emitting layer 30 from the first electrode A1. Further, the second blocking layer may be an exciton blocking layer which prevents an exciton formed in the light-emitting layer 30 from being diffused in a direction of the second electrode A2 and thus being non-radiatively decayed.

When the thickness of each of the first and second blocking layers is adjusted so as to be suitable for the resonance length of the light-emitting element 100, the light-emitting efficiency may be increased, and the exciton may be adjusted so as to be formed in the central part of the light-emitting layer 30.

FIG. 2 is a cross-sectional view for describing a light-emitting element according to another exemplary embodiment of the present invention.

Referring to FIG. 2, a light-emitting element 102 includes a first electrode A1, a hole transporting layer 22, a light-emitting layer 30, and a second electrode A2, which are formed on a base substrate 10. Except for the hole transporting layer 22, the other constituent elements are substantially the same as those described in FIG. 1, and thus the overlapping description thereof will be omitted.

The hole transporting layer 22 includes the compound represented by Formula 1 and a P-type dopant. Since a compound included in the hole transporting layer 22 is substantially the same as that described above, the overlapping specific description thereof will be omitted.

The P-type dopant may include a P-type organic dopant and/or a P-type inorganic dopant.

Specific examples of the P-type organic dopant include compounds represented by the following Formulae 7 to 11, hexadecafluorophthalocyanine (F16CuPc), 11,11,12,12-tetracyanonaphtho-2,6-quinodimethane (TNAP), 3,6-difluoro-2,5,7,7,7,8,8-hexacyano-quinodimethane (F2-HCNQ), or tetracyanoquinodimethane (TCNQ), and the like. These may be used either alone or in combination of two or more thereof.

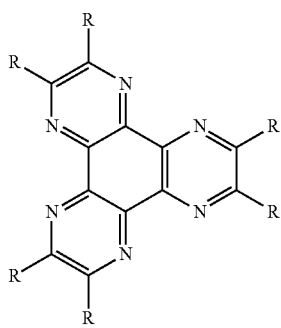

[Formula 7]

In Formula 7, R may represent a cyano group, a sulfone group, a sulfoxide group, a sulfonamide group, a sulfonate group, a nitro group, or a trifluoromethyl group.

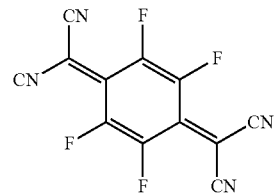

[Formula 8]

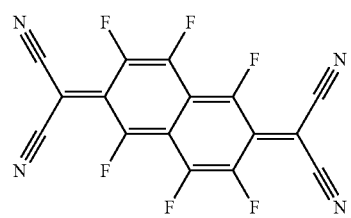

[Formula 9]

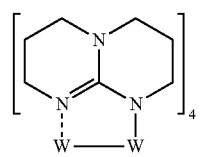

[Formula 10]

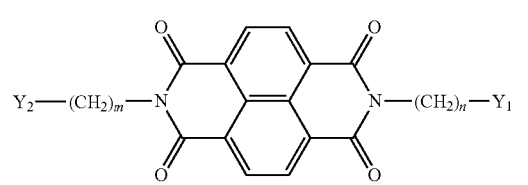

[Formula 11]

In Formula 11, m and n may each independently represent an integer of 1 to 5, and $Y_1$ and $Y_2$ may each independently represent an aryl group having 6 to 20 carbon atoms, or a heteroaryl group having 2 to 20 carbon atoms. In this case, hydrogen of the aryl group or heteroaryl group represented by $Y_1$ and $Y_2$ may be unsubstituted or substituted with an alkyl group having 1 to 5 carbon atoms, an alkoxy group having 1 to 5 carbon atoms, or a hydroxyl group, and hydrogen atoms of substituted or unsubstituted $Y_1$ and $Y_2$ may be each independently unsubstituted or substituted with a halogen group.

For example, the compound represented by Formula 11 may include a compound represented by the following Formula 11a or the following Formula 11b.

[Formula 11a]

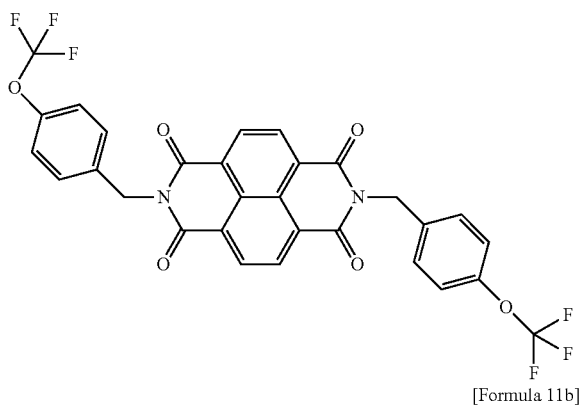

[Formula 11b]

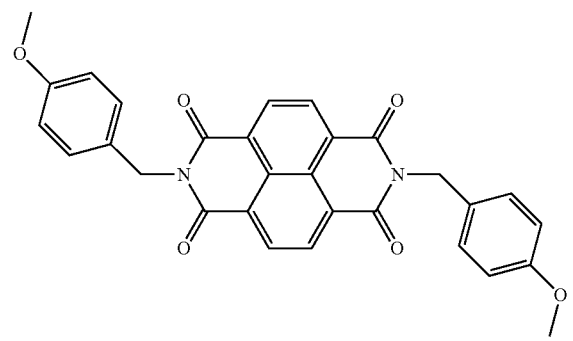

Examples of the P-type inorganic dopant include metal oxide or metal halide, and the like. Specific examples of the P-type inorganic dopant include $MoO_3$, $V_2O_5$, $WO_3$, $SnO_2$, $ZnO$, $MnO_2$, $CoO_2$, $ReO3$, $TiO_2$, $FeCl_3$, $SbCl_5$ or $MgF_2$, and the like. These may be used either alone or in combination of two or more thereof.

The content of the P-type dopant may be about 0.5 part by weight to about 20 parts by weight based on 100 parts by weight of the novel compound according to the present invention, which is a hole transport compound. For example, the content of the P-type dopant may be about 0.5 part by weight to about 15 parts by weight, or about 0.5 part by weight to about 5 parts by weight, based on 100 parts by weight of the hole transport compound. In contrast, the content of the P-type dopant may be about 1 part by weight to about 10 parts by weight, about 1 part by weight to about 5 parts by weight, about 1.5 parts by weight to about 6 parts by weight, or about 2 parts by weight to about 5 parts by weight, based on 100 parts by weight of the hole transport compound.

When the content of the P-type dopant is about 0.5 part by weight to about 20 parts by weight based on 100 parts by weight of the hole transport compound, the P-type dopant may prevent an excessive leakage current from being generated without degrading physical properties of the hole transport compound. In addition, the energy barrier at the interface with each of the upper and lower layers, which are brought into contact with the hole transporting layer 22, may be reduced by the P-type dopant.

Even though not illustrated in the drawing, the light-emitting element 102 may further include an electron transporting layer, an electron injecting layer, a first blocking layer, and/or a second blocking layer. Since the layers are substantially the same as those described in the light-emitting element 100 of FIG. 1, the specific description thereof will be omitted. When the light-emitting element 102 includes the first blocking layer, the first blocking layer may include the compound according to the present invention, which is described above.

Meanwhile, the light-emitting element 100 illustrated in FIG. 1 may further include an interlayer (not illustrated). The interlayer may be disposed between the first electrode A1 and the hole transporting layer 20 of FIG. 1, and may be formed of the compound used as the P-type dopant described in FIG. 2.

FIG. 3 is a cross-sectional view for describing a light-emitting element according to still another exemplary embodiment of the present invention.

Referring to FIG. 3, a light-emitting element 104 includes a first electrode A1, a hole transporting layer 24, a light-emitting layer 30, and a second electrode A2, which are formed on a base substrate 10. Except for the hole transporting layer 24, the other constituent elements are substantially the same as those described in FIG. 1, and thus the overlapping description thereof will be omitted.

The hole transporting layer 24 includes a first layer 23a brought into contact with the first electrode A1 and a second layer 23b disposed between the first layer 23a and the light-emitting layer 30. That is, the hole transporting layer 24 may have a two-layer structure. Furthermore, the hole transporting layer 24 may have a multi-layer structure having two or more layers, which includes the first and second layers 23a and 33b.

The first and second layers 23a and 23b may include the same kind of hole transport compound. Since the first layer 23a and the second layer 23b include the same hole transport compound, physical and chemical defects which may be generated at the interface between different species materials may be reduced, thereby facilitating injection of holes into the light-emitting layer. In another aspect, when the same hole transport compound is used for the first layer 23a and the second layer 23b, there are advantages in that the first layer 23a and the second layer 23b may be continuously formed within one chamber, so that the manufacturing process may be simplified and the manufacturing time may be shortened. Furthermore, physical properties such as the glass transition temperature between the layers adjacent to each other become similar to each other, so that there is also an advantage in that durability of the element may be increased.

The first layer 23a includes the novel compound according to the present invention, which is represented by Formula 1, as the hole transport compound, and a P-type dopant. Except for the thickness, the first layer 23a is substantially the same as the hole transporting layer 22 described in FIG. 2. Therefore, the overlapping description thereof will be omitted.

The second layer 23b includes the novel compound according to the present invention, which is represented by Formula 1, as the hole transport compound, but the hole transport compound which constitutes the second layer 23b may be the same as the hole transport compound which constitutes the first layer 23a. Except for the thickness, the second layer 23b is also substantially the same as the hole transporting layer 20 described in FIG. 1, and thus the overlapping detailed description thereof will be omitted.

In contrast, the first and second layers 23a and 23b may include a different kind of hole transport compound. The hole transport compound, which constitutes the first and second layers 23a and 23b, is the novel compound according to the present invention, which is represented by Formula 1, but $Z_1$, $Z_2$, $Z_3$, $L_a$, $L_b$, and $L_c$ may be each independently different from each other. In this case, the compound, which constitutes each of the first and second layers 23a and 23b, may be selected so as to have a HOMO value for efficiently transferring holes to the light-emitting layer 30.

Additionally, the second layer 23b may further include a P-type dopant together with the hole transport compound. In this case, the kinds of P-type dopants doped in the first layer 23a and the second layer 23b may be different from each other, and an amount of doping may vary even though the same kind of P-type dopants are used. For example, a content (P1) of the P-type dopant doped in the first layer 23a and a content (P2) of the P-type dopant doped in the second layer 23b may satisfy the relationship of the following Equation 1.

$$P1/P2 \geq 1 \qquad \text{[Equation 1]}$$

In Equation 1,

"P1" is a content of the P-type dopant doped in the first layer 23a based on 100 parts by weight of the hole transport compound, and "P2" is a content of the P-type dopant doped in the second layer 23b based on 100 parts by weight of the hole transport compound.

For example, the content of the P-type dopant doped in the first layer 23a may range from 0.3 to 20 parts by weight, 1 to 15 parts by weight, 2 to 10 parts by weight, or 4 to 6 parts by weight, based on 100 parts by weight of the hole transport compound. Further, the content of the P-type dopant doped in the second layer 23b may range from 0.3 to 20 parts by weight, 0.5 to 10 parts by weight, 1 to 8 parts by weight, or 2 to 4 parts by weight, based on 100 parts by weight of the hole transport compound.

In addition, even though not illustrated in the drawing, the light-emitting element 104 may further include an electron transporting layer, an electron injecting layer, a first blocking layer, and/or a second blocking layer. Since the layers are substantially the same as those described in the light-emitting element 100 of FIG. 1, the specific description thereof will be omitted.

FIG. 4 is a cross-sectional view for describing a light-emitting element according to yet another exemplary embodiment of the present invention.

Referring to FIG. 4, a light-emitting element 106 includes a first electrode A1, a hole transporting layer 26, a light-emitting layer 30, an electron transporting layer 40, and a second electrode A2. In FIG. 4, except for the hole transporting layer 26 and the electron transporting layer 40, the light-emitting element 106 are substantially the same as the light-emitting element 100 described in FIG. 1, and thus the overlapping specific description thereof will be omitted.

The hole transporting layer 26 may include N,N'-diphenyl-N,N'-bis(1-naphthyl)-1,1'-biphenyl-4,4'-diamine (NPB) or N,N'-diphenyl-N,N'-bis(3-methyl phenyl)-1,1'-biphenyl-4,4'-diamine (TPD), and the like. The kind of compound which constitutes the hole transporting layer 26 is not limited thereto, and various kinds thereof may be used. These may be used either alone or in combination of two or more thereof.

The electron transporting layer 40 includes the novel compound according to the present invention. That is, a compound included in the electron transporting layer 40 may be represented by Formula 1. Therefore, the overlapping specific description of the compound according to the present invention will be omitted. For example, the compound included in the electron transporting layer 40 may include a structure in which at least one of $Z_1$, $Z_2$, and $Z_3$ in Formula 1 is represented by Formula 5 or Formula 6. In this case, the electron transporting layer 40 may further include an electron transport compound different from the novel compound represented by Formula 1. Examples of the electron transport compound include 4,7-diphenyl-1,10-phenanthroline (BPhen), 8-hydroxyquinolinolato-lithium (Liq), 2-(4-(9,10-di(naphthalen-2-yl)anthracen-2-yl)phenyl)-1-phenyl-1H-benzo[d]imidazole, and the like.

The electron transporting layer 40 may further include an N-type dopant. Specific examples of the N-type dopant include an alkaline metal such as Li, Na, K, Rb, and Cs, an alkaline earth metal such as Be, Mg, Ca, and Ba, a rare-earth metal such as Sc, Y, Yb, Eu, Sm, and Ce, a halogen salt thereof (LiF, CsF, and the like) or an oxide salt thereof ($Cs_2MoO_4$, $Cs_2WO_4$, and the like), and the like. These may be used either alone or in combination of two or more thereof. The kind of the N-type dopant is not limited thereto, and various commercially available compounds may be used.

Even though not illustrated in the drawing, the hole transporting layer 26 illustrated in FIG. 4 may be replaced with the hole transporting layer 20 described in FIG. 1. That is, the first electrode A1, the hole transporting layer described in FIG. 1, the light-emitting layer 30, the electron transporting layer 40, and the second electrode A2 may be sequentially stacked to constitute a light-emitting element. However, the compound included in the hole transporting layer 20 is represented by Formula 1, but may have a structure different from the compound included in the electron transporting layer 40. For example, when the compound included in the electron transporting layer 40 includes the structure of Formula 5, the hole transporting layer 20 may include the structure of Formula 2 or 3.

FIG. 5 is a cross-sectional view for describing a light-emitting element according to still yet another exemplary embodiment of the present invention.

Referring to FIG. 5, a light-emitting element 108 includes a first electrode A1, a hole transporting layer 26, a light-emitting layer 32, and a second electrode A2. Since the light-emitting element 108 illustrated in FIG. 5 is substantially the same as the light-emitting element 100 described in FIG. 1, except for the hole transporting layer 26 and the light-emitting layer 32, the overlapping specific description thereof will be omitted.

The hole transporting layer 26 is substantially the same as that described in FIG. 4. Therefore, the overlapping specific description thereof will be omitted.

The light-emitting layer 32 includes the novel compound according to the present invention as a first light-emitting compound. That is, the first light-emitting compound included in the light-emitting layer 32 may be represented by Formula 1. Therefore, the overlapping specific description thereof will be omitted. For example, the first light-emitting compound may include a structure in which at least one of $Z_1$, $Z_2$, and $Z_3$ in Formula 1 is represented by Formula 4.

The light-emitting layer 32 may further include a second light-emitting compound. The second light-emitting compound is not particularly limited, and includes all the examples of various commercially available compounds. In this case, the light-emitting layer 32 includes the first light-emitting compound as a host material, and may include the second light-emitting compound as a dopant material. In this case, the second light-emitting compound may use various compounds used as a commercially available light-emitting dopant.

The light-emitting layer 32 illustrated in FIG. 5 may constitute a light-emitting element together with the hole transporting layers 20, 22, and 24 described in FIGS. 1 to 3, and may also constitute a light-emitting element together with the electron transporting layer 40 described in FIG. 4.

Each of the light-emitting elements 100, 102, 104, 106, and 108 described above includes the novel compound according to the present invention, which is represented by Formula 1, and thus the light-emitting elements 100, 102, 104, 106, and 108 may have excellent thermal stability, and simultaneously, the light-emitting efficiency thereof may be enhanced and the lifespan thereof may be increased.

FIGS. 1 to 5 illustrate that the light-emitting elements 100, 102, 104, 106, and 108 are directly formed on the base substrate 10, but a thin film transistor may be disposed as a driving element, which drives pixels, between the first electrode A1 of each of the light-emitting elements 100, 102, 104, 106, and 108, and the base substrate 10. In this case, the first electrode A1 may become a pixel electrode connected to the thin film transistor. When the first electrode A1 is a pixel electrode, the first electrodes A1 are disposed spaced apart from each other in each of a plurality of pixels, and a partition wall pattern formed along the edge of the first electrode A1 is formed on the base substrate 10, so that layers to be stacked on the first electrode A1 disposed on the pixels adjacent to each other may be isolated from each other. That is, even though not illustrated in the drawings, the light-emitting elements 100, 102, 104, 106, and 108 may be used for a display device which displays an image without a backlight.

Furthermore, the light-emitting elements 100, 102, 104, 106, and 108 may be used as a lighting device.

As described above, the light-emitting elements 100, 102, 104, 106, and 108 exemplified in the present invention may be used for various electronic devices such as the display device or the lighting device.

EXAMPLES

Hereinafter, novel compounds according the present invention will be described in more detail through specific Examples according to the present invention. The Examples to be exemplified below are only provided for the detailed description of the invention, but are not intended to limit the right scope thereby.

Example 1

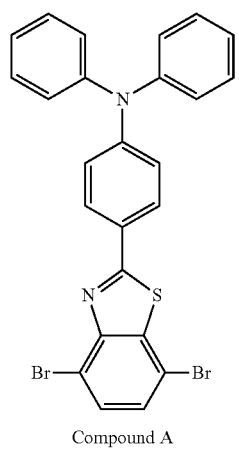

Compound A

+

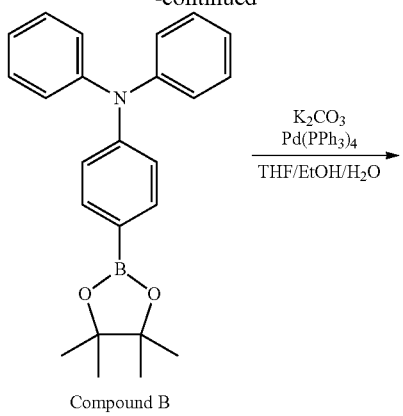

Compound B $$\xrightarrow{\substack{K_2CO_3 \\ Pd(PPh_3)_4 \\ THF/EtOH/H_2O}}$$

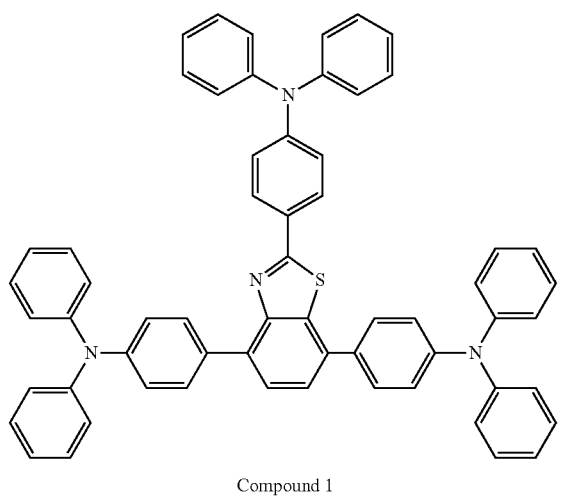

Compound 1

A 500 mL three-neck round-bottom flask was filled with nitrogen, and then Compound A (31.83 mmol, 17.0 g), Compound B (66.86 mmol, 24.81 g), 170 mL of tetrahydrofuran (THF), and 85 mL of ethanol (EtOH) were added thereto, and the resulting mixture was stirred for 30 minutes. Further, potassium carbonate ($K_2CO_3$) (127.32 mmol, 17.59 g) was dissolved in 85 mL of water ($H_2O$), and then the resulting solution was added to the 500 mL three-neck round-bottom flask. Subsequently, tetrakis(triphenylphosphine)palladium ($Pd(PPh_3)_4$) (1.27 mmol, 1.42 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), and the resulting solution was put into 850 mL of methanol and stirred for 20 minutes, and then filtered, thereby obtaining about 23.7 g of a pale green solid Compound 1 (yield 86%).

MALDI-TOF: m/z=864.3345 ($C_{61}H_{44}N_4S$=864.33)

Example 2

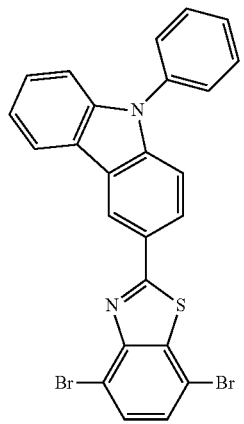

Compound C

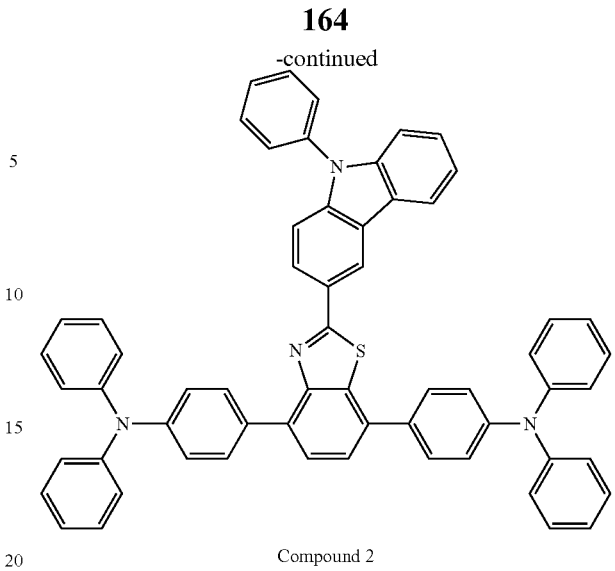

Compound 2

A 500 mL three-neck round-bottom flask was filled with nitrogen, and then Compound C (31.89 mmol, 17.0 g), Compound B (66.97 mmol, 24.86 g), 170 mL of tetrahydrofuran (THF), and 85 mL of ethanol (EtOH) were added thereto, and the resulting mixture was stirred for 20 minutes. Further, potassium carbonate ($K_2CO_3$) (127.56 mmol, 17.63 g) was dissolved in 85 mL of water ($H_2O$), and then the resulting solution was added to the 500 mL three-neck round-bottom flask. Subsequently, tetrakis(triphenylphosphine)palladium ($Pd(PPh_3)_4$) (1.27 mmol, 1.42 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), 850 mL of methanol was added thereto, and the resulting solution was stirred for 20 minutes, and then filtered, thereby obtaining about 23.8 g of a pale green solid Compound 2 (yield 86%).

MALDI-TOF: m/z=864.3356 ($C_{61}H_{42}N_4S$=862.31)

Example 3

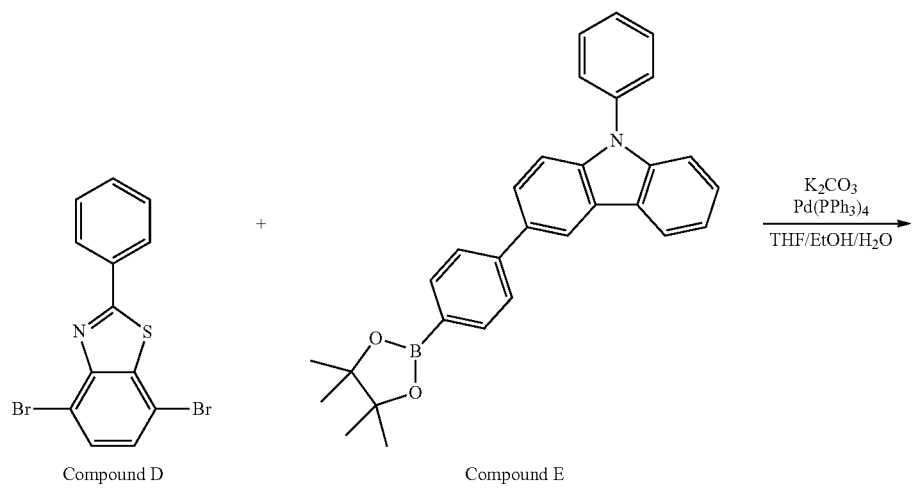

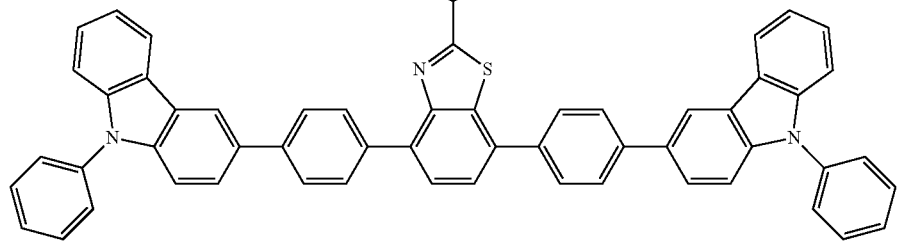

Compound 3

A 500 mL three-neck round-bottom flask was filled with nitrogen, and then Compound D (46.33 mmol, 17.0 g), Compound E (97.31 mmol, 43.32 g), 170 mL of tetrahydrofuran (THF), and 85 mL of ethanol (EtOH) were added thereto, and the resulting mixture was stirred for 30 minutes. Further, potassium carbonate ($K_2CO_3$) (185.32 mmol, 25.61 g) was dissolved in 85 mL of water ($H_2O$), and then the resulting solution was added to the 500 mL three-neck round-bottom flask. Subsequently, tetrakis(triphenylphosphine)palladium ($Pd(PPh_3)_4$) (1.85 mmol, 2.68 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), and the resulting solution was put into 850 mL of methanol and stirred for 20 minutes, and then filtered, thereby obtaining about 34.5 g of a yellow solid Compound 3 (yield 88%).

MALDI-TOF: m/z=845.2934 ($C_{61}H_{39}N_3S$=845.29)

Example 4

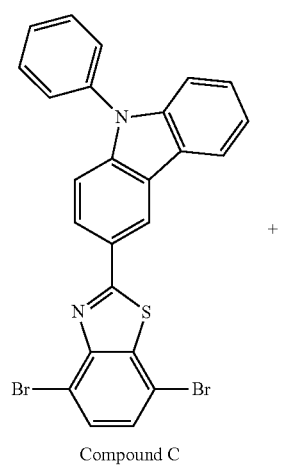

Compound C

+

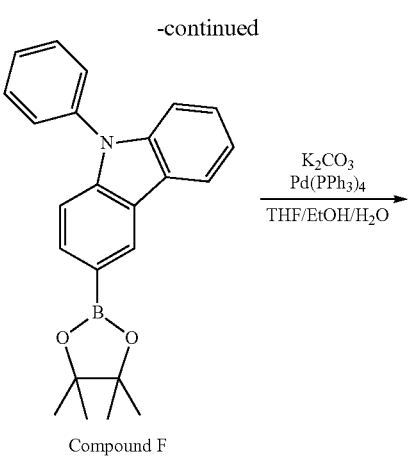

Compound F $\xrightarrow[\text{THF/EtOH/H}_2\text{O}]{K_2CO_3 \; Pd(PPh_3)_4}$

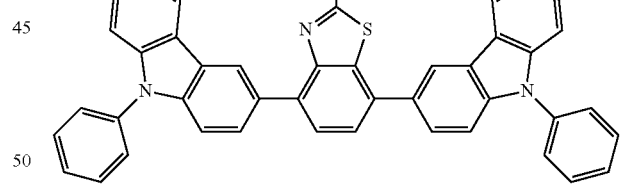

Compound 4

A 500 mL three-neck round-bottom flask was filled with nitrogen, and then Compound C (33.84 mmol, 18.0 g), Compound F (71.06 mmol, 26.23 g), 180 mL of tetrahydrofuran (THF), and 90 mL of ethanol (EtOH) were added thereto, and the resulting mixture was stirred for 35 minutes. Further, potassium carbonate ($K_2CO_3$) (135.36 mmol, 18.70 g) was dissolved in 90 mL of water ($H_2O$), and then the resulting solution was added to the 500 mL three-neck round-bottom flask. Subsequently, tetrakis(triphenylphosphine)palladium ($Pd(PPh_3)_4$) (1.35 mmol, 1.51 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 90 mL of tetrahydrofuran (THF), the resulting solution was put into 900 mL of methanol, stirred for 20 minutes, and then filtered, thereby obtaining about 19.7 g of a brown solid Compound 4 (yield 89%).

MALDI-TOF: m/z=858.2825 ($C_{61}H_{38}N_4S=858.28$)

Example 5

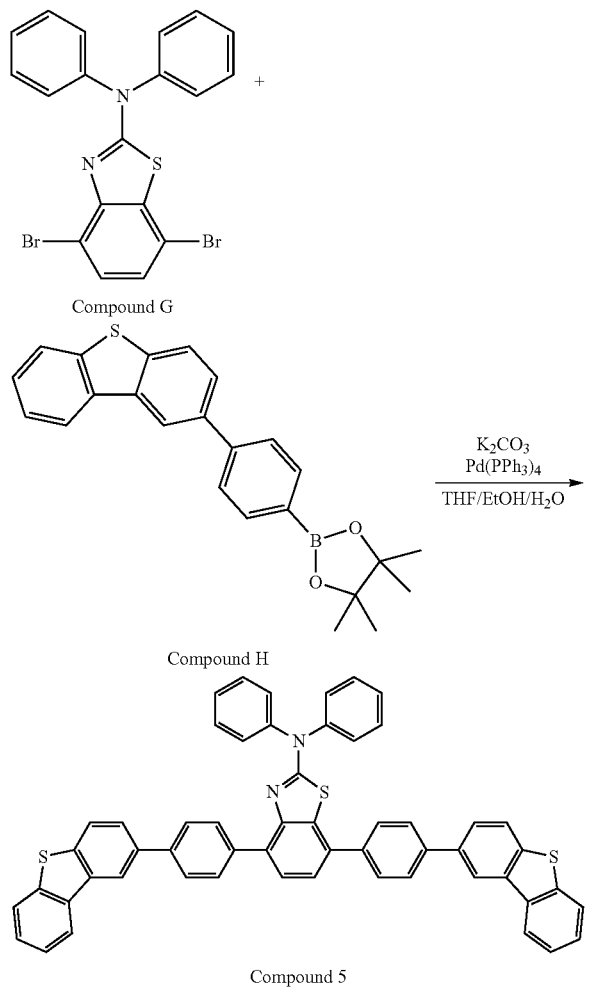

A 500 mL three-neck round-bottom flask was filled with nitrogen, and then Compound G (28.39 mmol, 13.0 g), Compound H (59.62 mmol, 23.02 g), 130 mL of tetrahydrofuran (THF), and 60 mL of ethanol (EtOH) were added thereto, and the resulting mixture was stirred for 25 minutes. Further, potassium carbonate ($K_2CO_3$) (133.56 mmol, 15.69 g) was dissolved in 60 mL of water ($H_2O$), and then the resulting solution was added to the 500 mL three-neck round-bottom flask. Subsequently, tetrakis(triphenylphosphine)palladium (Pd(PPh$_3$)$_4$) (1.18 mmol, 1.31 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 60 mL of tetrahydrofuran (THF), the resulting solution was put into 600 mL of methanol, stirred for 20 minutes, and then filtered, thereby obtaining about 21.7 g of a white solid Compound 5 (yield 94%).

MALDI-TOF): m/z=818.1925 ($C_{55}H_{34}N_2S_3=818.19$)

Example 6

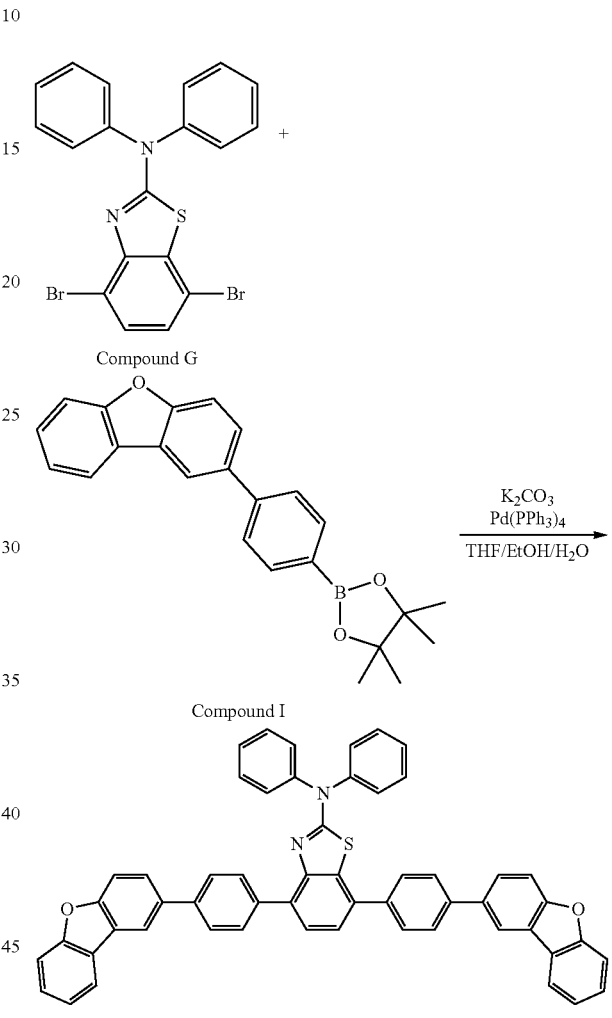

A 500 mL three-neck round-bottom flask was filled with nitrogen, and then Compound G (41.49 mmol, 19.0 g), Compound I (86.92 mmol, 32.17 g), 190 mL of tetrahydrofuran (THF), and 90 mL of ethanol (EtOH) were added thereto, and the resulting mixture was stirred for 40 minutes. Further, potassium carbonate ($K_2CO_3$) (165.96 mmol, 22.93 g) was dissolved in 90 mL of water ($H_2O$), and then the resulting solution was added to the 500 mL three-neck round-bottom flask. Subsequently, tetrakis(triphenylphosphine)palladium (Pd(PPh$_3$)$_4$) (1.66 mmol, 1.85 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 90 mL of tetrahydrofuran (THF), the resulting solution was put into 900 mL of methanol, stirred for 20 minutes, and then filtered, thereby obtaining about 28.6 g of a dark brown solid Compound 6 (yield 88%).

MALDI-TOF: m/z=786.2341 ($C_{55}H_{34}N_2O_2S$=786.23)

Example 7

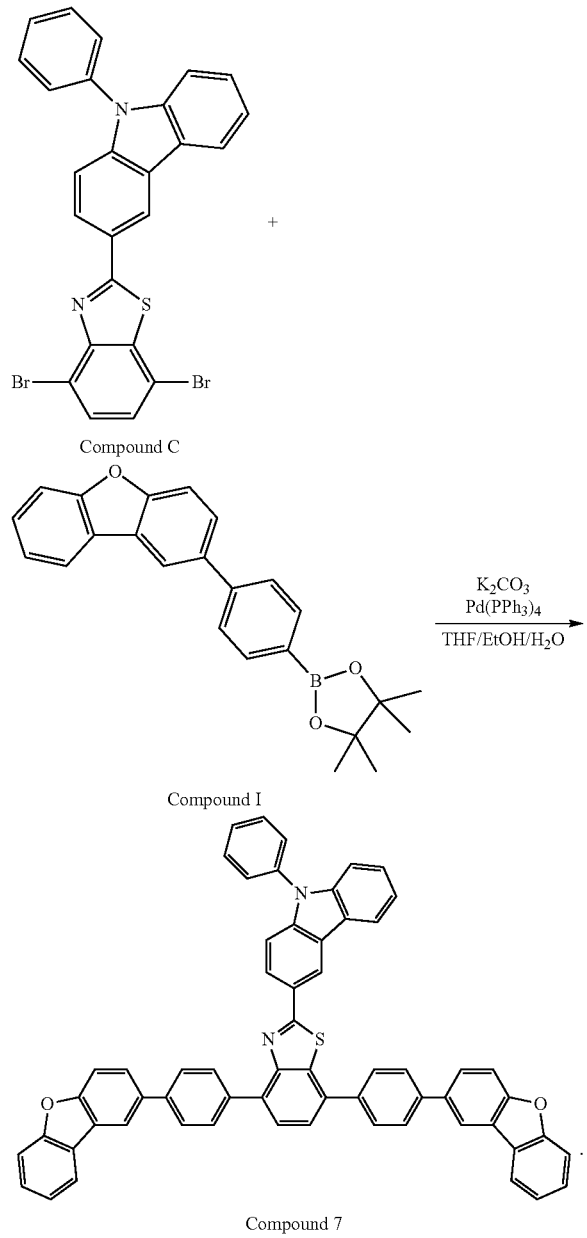

Compound 7

A 500 mL three-neck round-bottom flask was filled with nitrogen, and then Compound C (31.96 mmol, 17.0 g), Compound I (67.11 mmol, 24.84 g), 170 mL of tetrahydrofuran (THF), and 85 mL of ethanol (EtOH) were added thereto, and the resulting mixture was stirred for 25 minutes. Further, potassium carbonate ($K_2CO_3$) (127.84 mmol, 17.67 g) was dissolved in 85 mL of water ($H_2O$), and then the resulting solution was added to the 500 mL three-neck round-bottom flask. Subsequently, tetrakis(triphenylphosphine)palladium (Pd(PPh$_3$)$_4$) (1.280 mmol, 1.43 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), and the resulting solution was put into 850 mL of methanol and stirred for 20 minutes, and then filtered, thereby obtaining about 23.1 g of a yellow solid Compound 7 (yield 85%).

MALDI-TOF: m/z=860.2525 ($C_{61}H_{36}N_2O_2S$=860.25)

Example 8

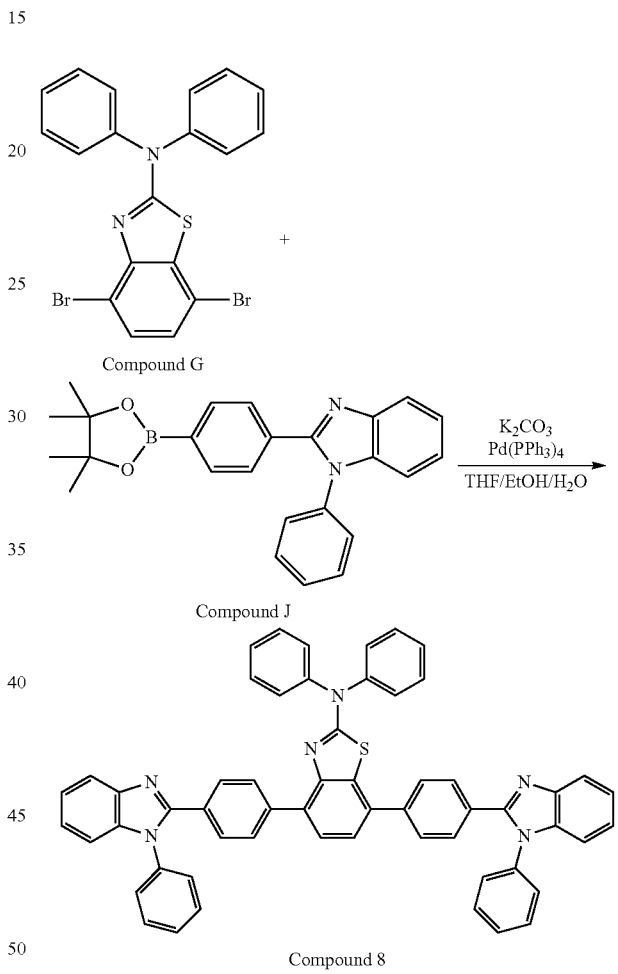

Compound 8

A 500 mL three-neck round-bottom flask was filled with nitrogen, and then Compound G (43.67 mmol, 20.0 g), Compound J (92.72 mmol, 36.34 g), 200 mL of tetrahydrofuran (THF), and 100 mL of ethanol (EtOH) were added thereto, and the resulting mixture was stirred for 35 minutes. Further, potassium carbonate ($K_2CO_3$) (174.68 mmol, 24.14 g) was dissolved in 100 mL of water ($H_2O$), and then the resulting solution was added to the 500 mL three-neck round-bottom flask. Subsequently, tetrakis(triphenylphosphine)palladium (Pd(PPh$_3$)$_4$) (1.741 mmol, 2.0 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 100 mL of tetrahydrofuran (THF), and the resulting solution was put into 1,000 mL of methanol and stirred for 20 minutes, and then filtered, thereby obtaining about 31.1 g of a yellowish green solid Compound 8 (yield 86%).

MALDI-TOF: m/z=838.2941 ($C_{57}H_{38}N_6S$=838.29)

Example 9

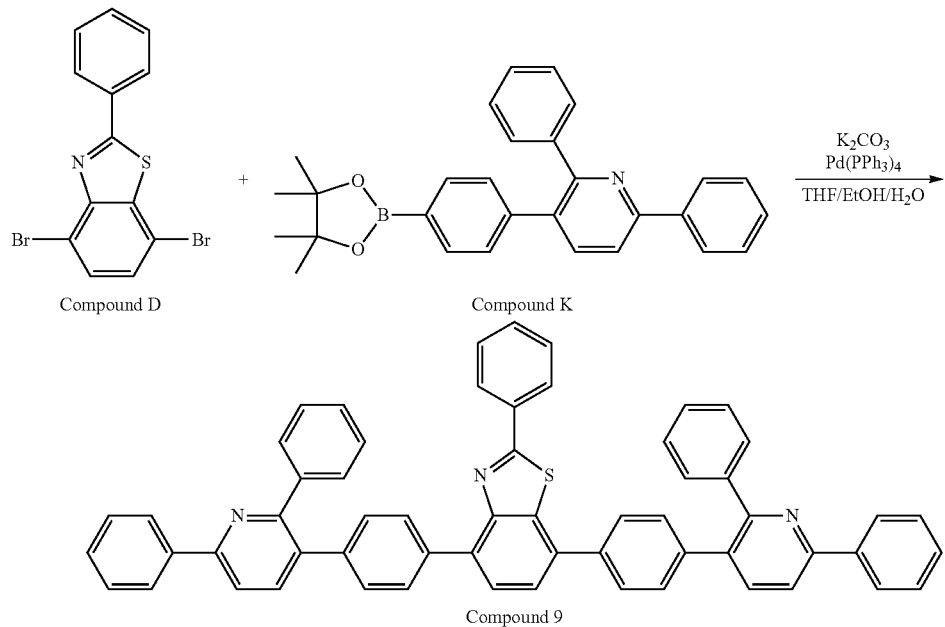

Compound D + Compound K

Compound 9

A 500 mL three-neck round-bottom flask was filled with nitrogen, and then Compound D (49.06 mmol, 18.0 g), Compound K (103.03 mmol, 44.63 g), 180 mL of tetrahydrofuran (THF), and 90 mL of ethanol (EtOH) were added thereto, and the resulting mixture was stirred for 30 minutes. Further, potassium carbonate ($K_2CO_3$) (196.24 mmol, 27.12 g) was dissolved in 90 mL of water ($H_2O$), and then the resulting solution was added to the 500 mL three-neck round-bottom flask. Subsequently, tetrakis(triphenylphosphine)palladium (Pd(PPh$_3$)$_4$) (1.96 mmol, 2.19 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 90 mL of tetrahydrofuran (THF), and the resulting solution was put into 900 mL of methanol and stirred for 20 minutes, and then filtered, thereby obtaining about 33.8 g of a pale green solid Compound 9 (yield 84%).

MALDI-TOF: m/z=821.2924 ($C_{59}H_{39}N_3S$=821.29)

Example 10

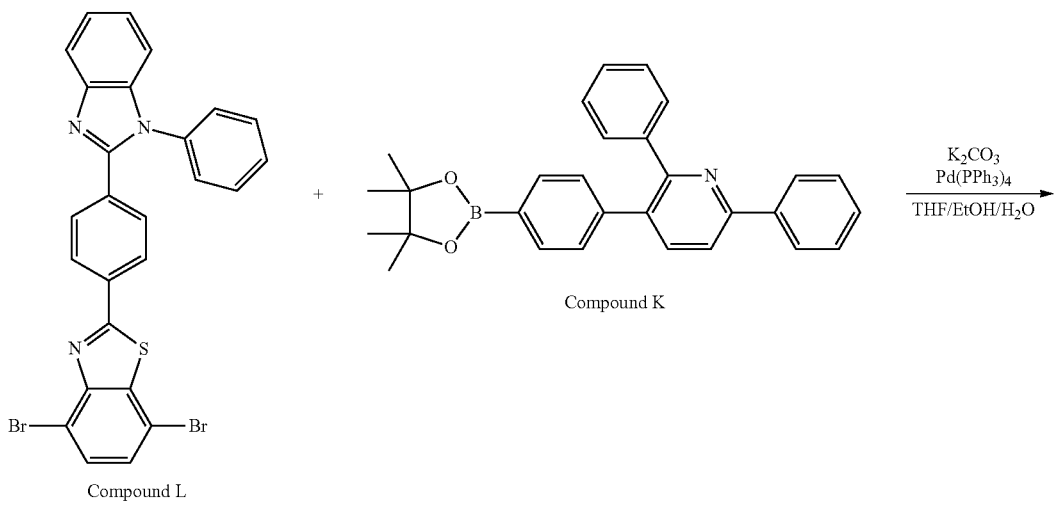

Compound L + Compound K

-continued

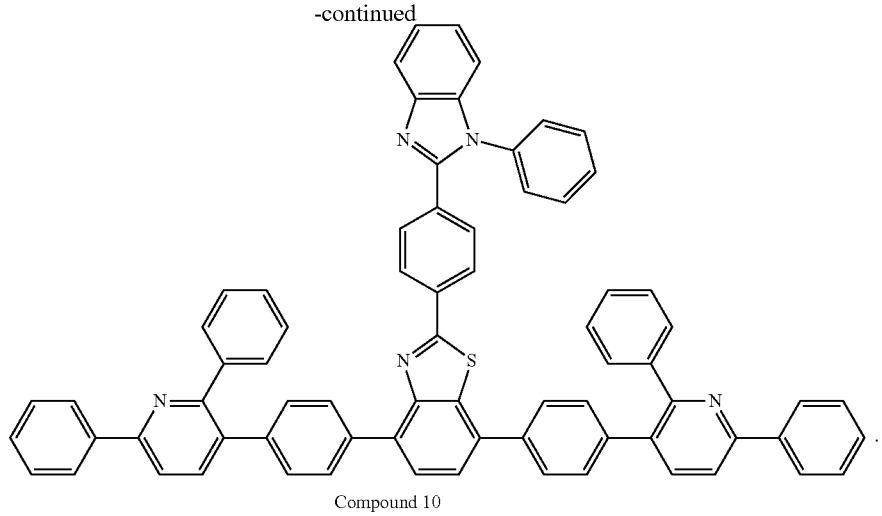

Compound 10

A 500 mL three-neck round-bottom flask was filled with nitrogen, and then Compound L (33.99 mmol, 19.0 g), Compound K (71.38 mmol, 30.92 g), 190 mL of tetrahydrofuran (THF), and 95 mL of ethanol (EtOH) were added thereto, and the resulting mixture was stirred for 25 minutes. Further, potassium carbonate ($K_2CO_3$) (135.96 mmol, 18.79 g) was dissolved in 95 mL of water ($H_2O$), and then the resulting solution was added to the 500 mL three-neck round-bottom flask. Subsequently, tetrakis(triphenylphosphine)palladium (Pd(PPh$_3$)$_4$) (1.36 mmol, 1.51 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 95 mL of tetrahydrofuran (THF), and the resulting solution was put into 950 mL of methanol and stirred for 20 minutes, and then filtered, thereby obtaining about 27.8 g of a yellow solid Compound 10 (yield 81%).

MALDI-TOF: m/z=1013.3636 ($C_{72}H_{47}N_5S$=1013.36)

Example 11

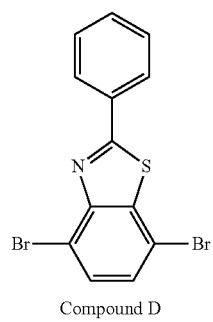

Compound D

+

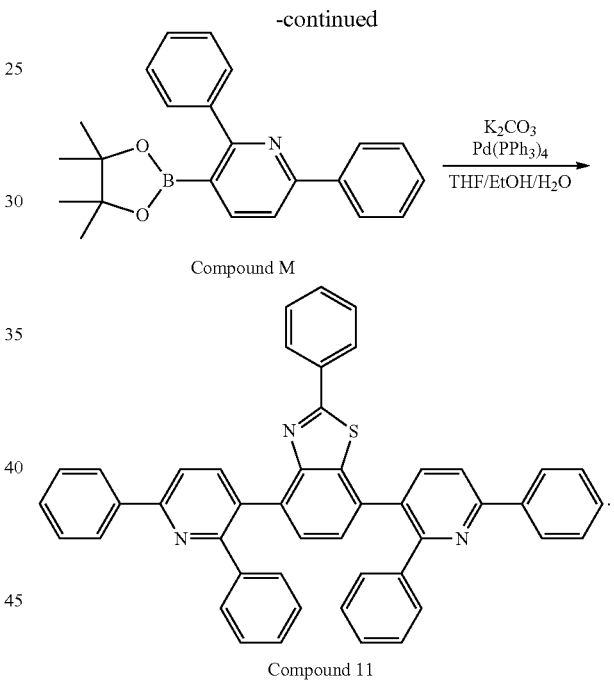

A 500 mL three-neck round-bottom flask was filled with nitrogen, and then Compound D (46.33 mmol, 17.0 g), Compound M (92.67 mmol, 33.10 g), 170 mL of tetrahydrofuran (THF), and 85 mL of ethanol (EtOH) were added thereto, and the resulting mixture was stirred for 30 minutes. Further, potassium carbonate ($K_2CO_3$) (185.32 mmol, 25.61 g) was dissolved in 85 mL of water ($H_2O$), and then the resulting solution was added to the 500 mL three-neck round-bottom flask. Subsequently, tetrakis(triphenylphosphine)palladium (Pd(PPh$_3$)$_4$) (1.85 mmol, 2.07 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), and the resulting solution was put into 850 mL of methanol and stirred for 20 minutes, and then filtered, thereby obtaining about 25.9 g of a brown solid Compound 11 (yield 84%).

MALDI-TOF: m/z=669.2243 ($C_{47}H_{31}N_3S$=669.22)

Example 12

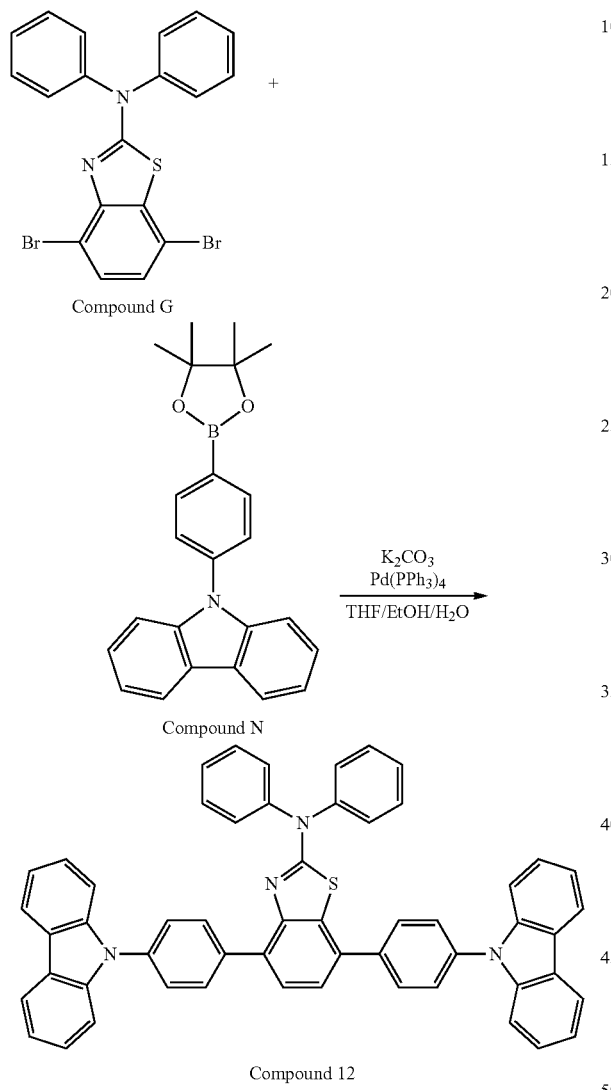

Compound 12

A 500 mL three-neck round-bottom flask was filled with nitrogen, and then Compound G (41.49 mmol, 19.0 g), Compound N (87.13 mmol, 32.17 g), 190 mL of tetrahydrofuran (THF), and 90 mL of ethanol (EtOH) were added thereto, and the resulting mixture was stirred for 30 minutes. Further, potassium carbonate ($K_2CO_3$) (165.96 mmol, 22.94 g) was dissolved in 30 mL of water ($H_2O$), and then the resulting solution was added to the 500 mL three-neck round-bottom flask. Subsequently, tetrakis(triphenylphosphine)palladium (Pd(PPh$_3$)$_4$) (1.66 mmol, 1.85 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 90 mL of tetrahydrofuran (THF), the resulting solution was put into 900 mL of methanol, stirred for 20 minutes, and then filtered, thereby obtaining about 26.7 g of a brown solid Compound 12 (yield 82%).

MALDI-TOF: m/z=784.2741 ($C_{55}H_{36}N_4S$=784.27)

Example 13

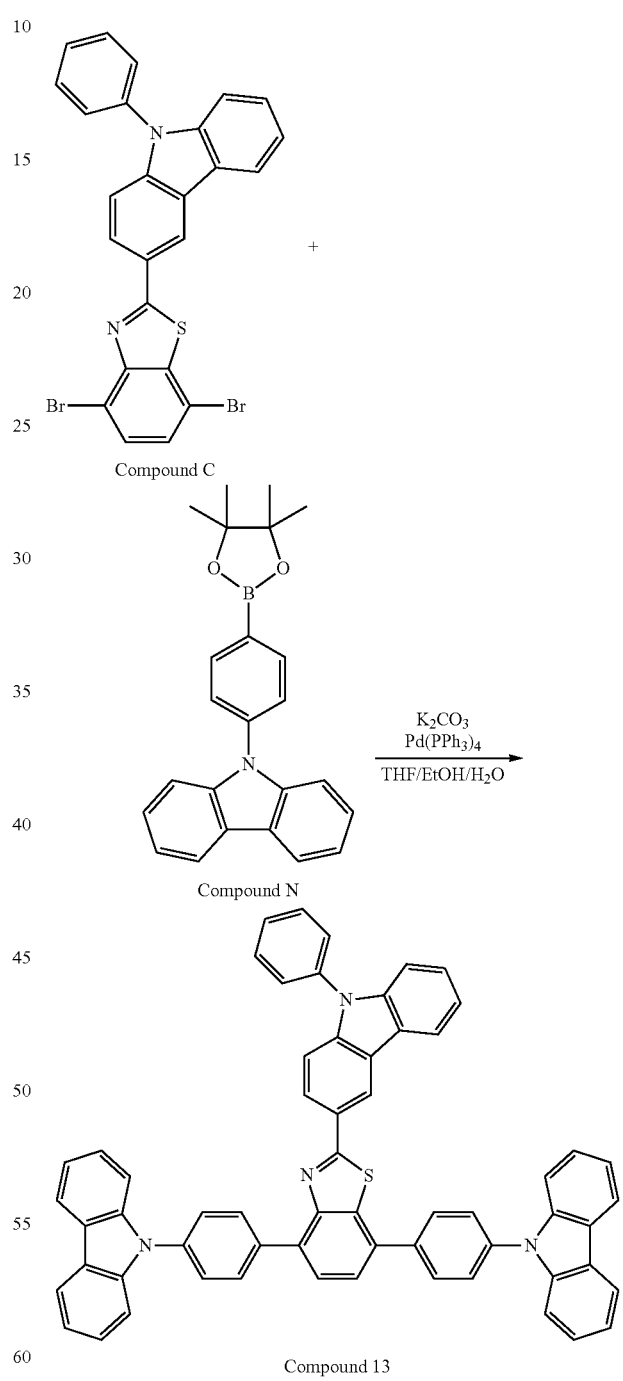

Compound 13

A 500 mL three-neck round-bottom flask was filled with nitrogen, and then Compound C (31.95 mmol, 17.0 g), Compound N (67.11 mmol, 24.77 g), 170 mL of tetrahydrofuran (THF), and 85 mL of ethanol (EtOH) were added thereto, and the resulting mixture was stirred for 20 minutes.

Further, potassium carbonate (K$_2$CO$_3$) (127.8 mmol, 17.66 g) was dissolved in 85 mL of water (H$_2$O), and then the resulting solution was added to the 500 mL three-neck round-bottom flask. Subsequently, tetrakis(triphenylphosphine)palladium (Pd(PPh$_3$)$_4$) (1.280 mmol, 1.42 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), and the resulting solution was put into 850 mL of methanol and stirred for 30 minutes, and then filtered, thereby obtaining about 22.4 g of a yellow solid Compound 13 (yield 82%).

MALDI-TOF: m/z=858.2825 (C$_{61}$H$_{38}$N$_4$S=858.28)

Example 14

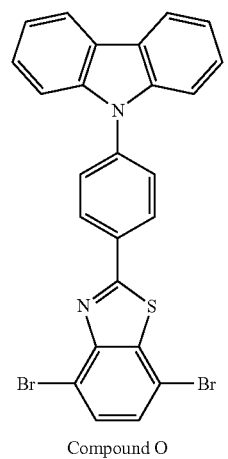

Compound O

+

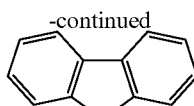

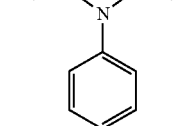

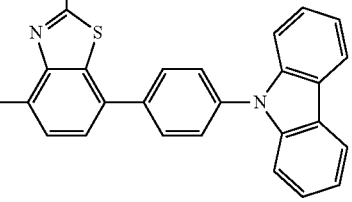

Compound N

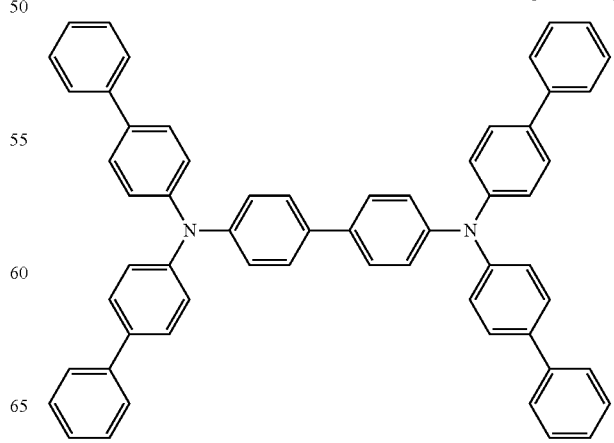

Compound 14

A 500 mL three-neck round-bottom flask was filled with nitrogen, and then Compound O (31.95 mmol, 17.0 g), Compound N (67.12 mmol, 24.77 g), 170 mL of tetrahydrofuran (THF), and 85 mL of ethanol (EtOH) were added thereto, and the resulting mixture was stirred for 30 minutes. Further, potassium carbonate (K$_2$CO$_3$) (127.8 mmol, 17.66 g) was dissolved in 85 mL of water (H$_2$O), and then the resulting solution was added to the 500 mL three-neck round-bottom flask. Subsequently, tetrakis(triphenylphosphine)palladium (Pd(PPh$_3$)$_4$) (1.28 mmol, 1.43 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), the resulting solution was put into 850 mL of methanol, stirred for 20 minutes, and then filtered, thereby obtaining about 22.7 g of a white solid Compound 14 (yield 83%).

MALDI-TOF: m/z=858.2825 (C$_{61}$H$_{38}$N$_4$S=858.28)

Comparative Examples 1 to 5

Compounds having the structures of the following Formulae a, b, c, d, and e were commercially purchased or prepared and were used as Comparative Examples 1 to 5, respectively.

[Formula a]

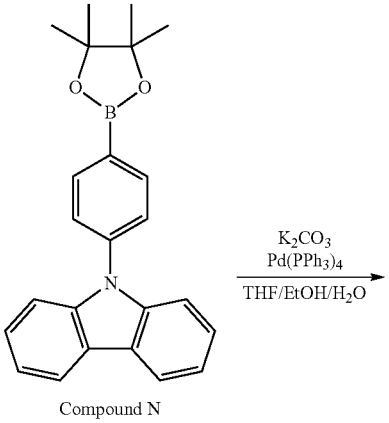

[Formula b]

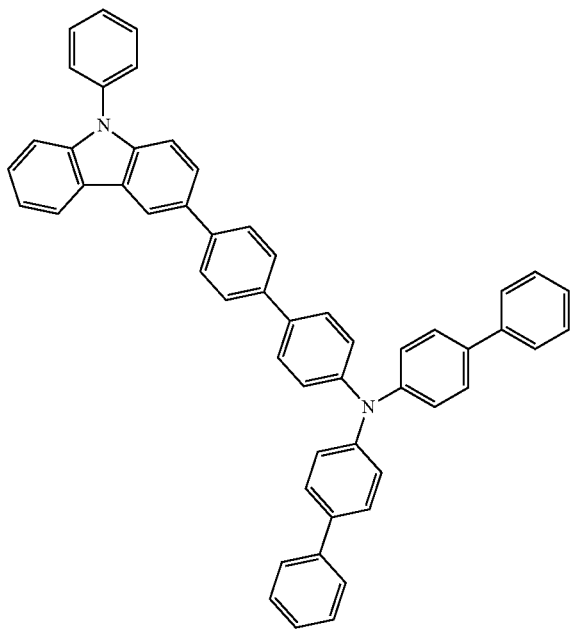

[Formula c]

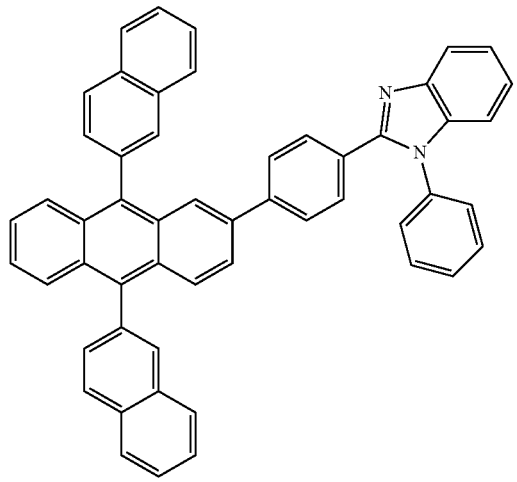

[Formula d]

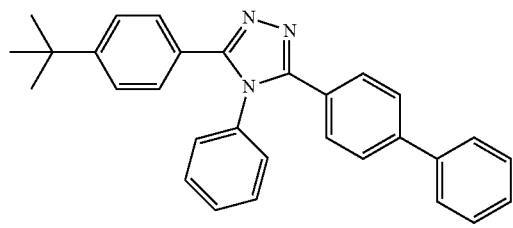

[Formula e]

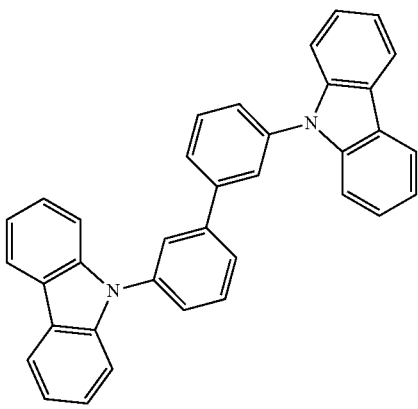

Manufacture of Light-Emitting Elements A-1 to A-7

The compound according to Example 1 as a host material of a hole transporting layer was deposited at a rate of 1 Å/sec, and simultaneously, a P-type dopant (HAT-CN) represented by the following Formula 12 was co-evaporated at a ratio of about 5 parts by weight based on 100 parts by weight of the host material, on a first electrode formed of indium tin oxide (ITO), thereby forming a first layer having a thickness of 100 Å. The compound according to Example 1 was deposited to have a thickness of 300 Å on the first layer, thereby forming a second layer.

mCBP (3,3-di(9H-carbazol-9-yl)biphenyl) represented by the following Formula 13 and Ir(ppy)$_3$ represented by the following Formula 14 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, Bphen represented by the following Formula 15 and Alq3 represented by the following Formula 16 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by the following Formula 17.

A second electrode using an aluminum thin film having a thickness of 1,000 Å was formed on the electron injecting layer.

[Formula 12]

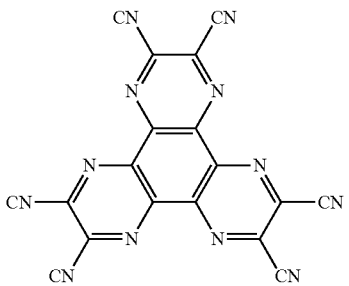

-continued

[Formula 13]
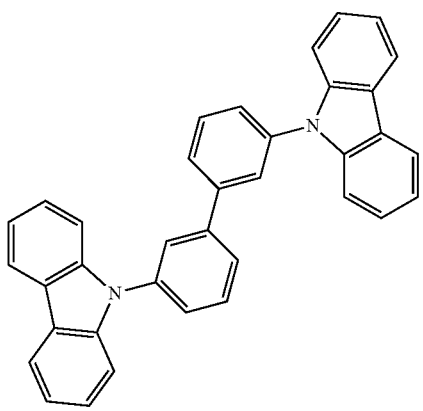

[Formula 14]
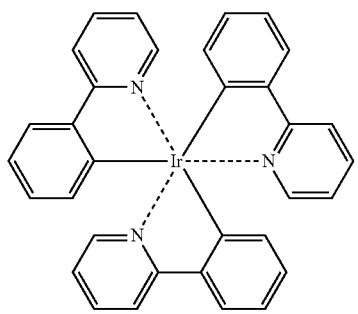

[Formula 15]
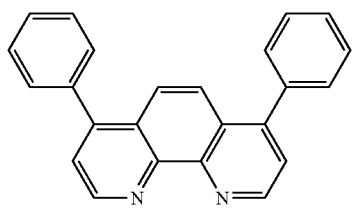

[Formula 16]
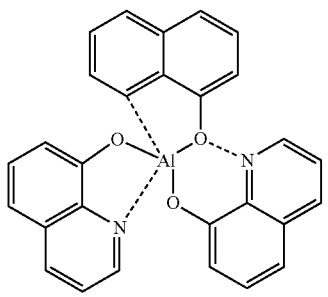

[Formula 17]
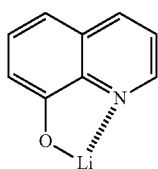

Light-Emitting Element A-1 including the compound according to Example 1 of the present invention was manufactured by the above method.

In addition, Light-Emitting Element A-2 to Light-Emitting Element A-7 were manufactured through a process which is substantially the same as the process of manufacturing Light-Emitting Element A-1, except that a hole transporting layer was formed by using each of the compounds according to Examples 2 to 7 as a host material of a hole transporting layer.

Manufacture of Comparative Elements 1 and 2

Comparative Elements 1 and 2 were manufactured through a process which is substantially the same as the process of manufacturing light-emitting element A-1, except that a first layer and a second layer were formed by using the compounds according to Comparative Examples 1 and 2 as a host material of a hole transporting layer.

Evaluation-1 of Power Efficiency and Lifespan of Light-Emitting Element

For each of Light-Emitting Elements A-1 to A-7 and Comparative Elements 1 and 2, a sealant for UV curing was dispensed at the edge of a cover glass, to which a moisture absorbent (Getter) was attached, in a glove box under a nitrogen atmosphere, and then each of the light-emitting elements and the comparative elements was cohered to the cover glass, and the sealant was cured by irradiating UV light thereon. For each of Light-Emitting Elements A-1 to A-7 and Comparative Elements 1 and 2 thus prepared above, the power efficiency was measured based on the value when the brightness was 500 cd/m$^2$ by using PR655 (trade name, manufactured by Photo Research Corp., USA) as a luminance meter. The result is shown in Table 21.

Further, the lifespan of each of Light-Emitting Elements A-1 to A-7 and Comparative Elements 1 and 2 was measured by using a lifetime measurement device provided in a measurement oven which was maintained constantly at a temperature of about 85° C. The result is shown in Table 21.

In Table 21, the unit of the result of measuring the power efficiency is lm/W. In addition, in Table 21, $T_{75}$ means a time for brightness of the light-emitting element to become 75% as compared to the initial brightness, when the initial brightness of the light-emitting element is 1,000 cd/m$^2$.

TABLE 21

| Element No. | Power efficiency [lm/W] | Lifespan ($T_{75}$@85° C. [hr]) |
|---|---|---|
| Light-Emitting Element A-1 | 28.6 | 659 |
| Light-Emitting Element A-2 | 33.1 | 764 |
| Light-Emitting Element A-3 | 31.0 | 715 |
| Light-Emitting Element A-4 | 34.3 | 794 |
| Light-Emitting Element A-5 | 24.4 | 552 |
| Light-Emitting Element A-6 | 24.8 | 561 |
| Light-Emitting Element A-7 | 24.5 | 566 |
| Comparative Element 1 | 9.2 | 227 |
| Comparative Element 2 | 9.8 | 254 |

Referring to Table 21, it can be seen that the power efficiency of each of the light-emitting elements manufactured by using the compounds according to Examples 1 to 7 of the present invention is about 24.4 lm/W or more, whereas the power efficiencies of Comparative Elements 1 and 2 is less than 10 lm/W. That is, it can be seen that the power efficiencies of the light-emitting elements including the compounds according to the present invention are better than those of Comparative Elements 1 and 2.

In addition, the lifespan of each of the light-emitting elements manufactured by using the compounds according to Examples 1 to 7 of the present invention is at least about 552 hours, and it can be seen that when the lifespan is compared to 227 hours and 254 hours, which are the lifespan of Comparative Elements 1 and 2, respectively, the lifespan of the light-emitting element including the compound according to the present invention is better than those of Comparative Elements 1 and 2.

Furthermore, considering that the evaluation of lifespan characteristics of the light-emitting element was performed under the acceleration (harsh) condition of 85° C., through the fact that the lifespan characteristics of the light-emitting elements including the compounds according to Examples 1 to 7 of the present invention are better than those of Comparative Elements 1 and 2, it can be seen that the heat resistances of the light-emitting elements manufactured by using the compound according to the present invention are better than those of Comparative Elements 1 and 2.

Manufacture of Light-Emitting Elements B-1 to B-3

The HAT-CN represented by Formula 12 was deposited to have a thickness of about 100 Å on a first electrode formed of indium tin oxide (ITO), thereby forming a first layer, and NPB (N,N'-diphenyl-N,N'-bis(1-naphthyl)-1,1'-biphenyl-4,4'-diamine) was formed to have a thickness of about 300 Å on the first layer, thereby forming a second layer.

The compound according to Example 2 was used to form a first blocking layer having a thickness of about 100 Å on the second layer, mCBP represented by Formula 13 and Ir(ppy)$_3$ represented by Formula 14 were co-deposited on the first blocking layer at a weight ratio of 100:9, thereby forming a light-emitting layer having a thickness of about 300 Å, and mCBP was deposited again to have a thickness of about 50 Å on the light-emitting layer, thereby forming a second blocking layer.

And then, Bphen represented by Formula 15 and Alq3 represented by Formula 16 were co-deposited at a weight ratio of 50:50 on the second blocking layer, thereby forming an electron transporting layer having a thickness of about 400 Å. Subsequently, an electron injecting layer having a thickness of about 10 Å was formed on the electron transporting layer by using Liq represented by Formula 17.

A second electrode was formed on the electron injecting layer by using an aluminum thin film having a thickness of 1,000 Å, thereby manufacturing Light-Emitting Element B-1 including the compound according to Example 2 of the present invention.

Light-Emitting Elements B-2 and B-3 were manufactured through a process which is substantially the same as the process of manufacturing Light-Emitting Element B-1, except that the first blocking layer was manufactured by using each of the compounds according to Examples 4 and 5 of the present invention.

Manufacture of Comparative Element 3

Comparative Element 3 was manufactured through a process which is substantially the same as the process of manufacturing Light-Emitting Element B-1, except that the first blocking layer was manufactured by using the compound according to Comparative Example 1, which is represented by Formula a.

Evaluation-2 of Power Efficiency and Lifespan of Light-Emitting Element

For each of Light-Emitting Element B-1 to B-3 and Comparative Element 3 thus prepared above, the power efficiency was measured by the method, which is substantially the same as in the experiment of measuring the power efficiency for Light-Emitting Elements A-1 to A-7, based on the value when the brightness was 500 cd/m$^2$ by using PR655 (trade name, manufactured by Photo Research Corp., USA) as a luminance meter.

In addition, the lifespan of each of Light-Emitting Elements B-1 to B-3 and Comparative Element 3 was measured by the method which is substantially the same as in the experiment of evaluating the lifespan for Light-Emitting Elements A-1 to A-7 described above.

The results of the power efficiency and lifespan of each of Light-Emitting Elements B-1 to B-3 and Comparative Element 3 are shown in Table 22. In Table 22, the unit of the result of measuring the power efficiency is lm/W. Furthermore, in Table 22, T$_{75}$ means a time for brightness of the light-emitting element to become 75% as compared to the initial brightness, when the initial brightness of the light-emitting element is 1,000 cd/m$^2$.

TABLE 22

| Element No. | Power efficiency [lm/W] | Lifespan (T$_{75}$@85° C. [hr]) |
|---|---|---|
| Light-Emitting Element B-1 | 33.6 | 789 |
| Light-Emitting Element B-2 | 34.7 | 820 |
| Light-Emitting Element B-3 | 25.9 | 584 |
| Comparative Element 3 | 7.9 | 185 |

Referring to Table 22, it can be seen that the power efficiency of each of the light-emitting elements manufactured by using the compounds according to Examples 2, 4, and 5 of the present invention is at least 25.9 lm/W or more, and it is also possible to manufacture a light-emitting element which exhibits a power efficiency of about 30 lm/W or more, whereas the power efficiency of Comparative Element 3 is only about 7.9 lm/W. Accordingly, it can be seen that the power efficiencies of the light-emitting elements including the compound according to the present invention are better than that of Comparative Element 3.

Further, the lifespan of each of the light-emitting elements manufactured by using the compounds according to Examples 2, 4, and 5 of the present invention is at least about 584 hours, and it can be seen that the lifespan of the light-emitting element including the compound according to the present invention is better than about 185 hours as the lifespan of Comparative Element 3.

In addition, considering that the evaluation of lifespan characteristics of the light-emitting element was performed under the acceleration (harsh) condition of 85° C., through the fact that the lifespan characteristics of the light-emitting elements including the compounds according to Examples 2, 4, and 5 of the present invention are better than those of Comparative Element 3, it can be seen that the heat resistance of the light-emitting element manufactured by using the compound according to the present invention is good.

Manufacture of Light-Emitting Elements C-1 to C-3

NPB as a host material of a hole transporting layer was deposited at a rate of 1 Å/sec, and simultaneously, the P-type dopant (HAT-CN) represented by Formula 12 was co-deposited at a ratio of about 5 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. The compound according to Example 2 was used to form a first blocking layer having a thickness of about 100 Å on the second layer, mCBP represented by Formula 13 and Ir(ppy)$_3$ represented by Formula 14 were co-deposited at a weight ratio of 100:9 on the first blocking layer, thereby forming a light-emitting layer having a thickness of about 300 Å, and mCBP was deposited again to have a thickness of about 50 Å on the light-emitting layer, thereby forming a second blocking layer.

And then, Bphen represented by Formula 15 and Alq3 represented by Formula 16 were co-deposited at a weight ratio of 50:50 on the second blocking layer, thereby forming an electron transporting layer having a thickness of about 400 Å. Subsequently, an electron injecting layer having a thickness of about 10 Å was formed on the electron transporting layer by using Liq represented by Formula 17.

A second electrode was formed on the electron injecting layer by using an aluminum thin film having a thickness of 1,000 Å, thereby manufacturing Light-Emitting Element C-1 including the compound according to Example 2 of the present invention.

Light-Emitting Elements C-2 and C-3 were manufactured through a process which is substantially the same as the process of manufacturing Light-Emitting Element C-1, except that the first blocking layer was manufactured by using each of the compounds according to Examples 4 and 7 of the present invention.

Manufacture of Comparative Element 4

Comparative Element 4 was manufactured through a process which is substantially the same as the process of manufacturing Light-Emitting Element C-1, except that the first blocking layer was manufactured by using the compound according to Comparative Example 1, which is represented by Formula a.

Evaluation-3 of Power Efficiency and Lifespan of Light-Emitting Element

For each of Light-Emitting Elements C-1 to C-3 and Comparative Element 4 thus prepared above, the power efficiency was measured by the method, which is substantially the same as in the experiment of measuring the power efficiency for Light-Emitting Elements A-1 to A-7, based on the value when the brightness was 500 cd/m² by using PR655 (trade name, manufactured by Photo Research Corp., USA) as a luminance meter.

Further, the lifespan of each of Light-Emitting Elements C-1 to C-3 and Comparative Element 4 was measured by the method which is substantially the same as in the experiment of evaluating the lifespan for Light-Emitting Elements A-1 to A-7 described above.

The results of the power efficiency and lifespan of each of Light-Emitting Elements C-1 to C-3 and Comparative Element 4 are shown in Table 23. In Table 23, the unit of the result of measuring the power efficiency is lm/W. In addition, in Table 23, $T_{75}$ means a time for brightness of the light-emitting element to become 75% as compared to the initial brightness, when the initial brightness of the light-emitting element is 1,000 cd/m².

TABLE 23

| Element No. | Power efficiency [lm/W] | Lifespan ($T_{75}$@85° C. [hr]) |
|---|---|---|
| Light-Emitting Element C-1 | 34.2 | 681 |
| Light-Emitting Element C-2 | 36.1 | 707 |
| Light-Emitting Element C-3 | 28.5 | 528 |
| Comparative Element 4 | 8.2 | 201 |

Referring to Table 23, it can be seen that the power efficiency of each of the light-emitting elements manufactured by using the compounds according to Examples 2, 4, and 7 of the present invention is at least 28.5 lm/W or more, and it is also possible to manufacture a light-emitting element which exhibits a power efficiency of about 36 lm/W or more, whereas the power efficiency of Comparative Element 4 is only about 8.2 lm/W. Accordingly, it can be seen that the power efficiencies of the light-emitting elements including the compound according to the present invention are better than that of Comparative Element 4.

Further, the lifespan of each of the light-emitting elements manufactured by using the compounds according to Examples 2, 4, and 7 of the present invention is at least about 528 hours, and it can be seen that the lifespan of the light-emitting element including the compound according to the present invention is better than about 201 hours as the lifespan of Comparative Element 4.

In addition, considering that the evaluation of lifespan characteristics of the light-emitting element was performed under the acceleration (harsh) condition of 85° C., through the fact that the lifespan characteristics of the light-emitting elements including the compounds according to Examples 2, 4, and 7 of the present invention are better than those of Comparative Element 4, it can be seen that the heat resistance of the light-emitting element manufactured by using the compound according to the present invention is good.

Manufacture of Light-Emitting Elements D-1 to D-3

The compound according to Example 1 as a host material of a hole transporting layer was deposited at a rate of 1 Å/sec, and simultaneously, the P-type dopant (HAT-CN) represented by Formula 12 was co-deposited at a ratio of about 5 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. mCBP represented by Formula 13 and Ir(ppy)$_3$ represented by Formula 14 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, Bphen represented by Formula 15 and Alq3 represented by Formula 16 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by Formula 17.

A second electrode was formed on the electron injecting layer by using an aluminum thin film having a thickness of 1,000 Å, thereby manufacturing Light-Emitting Element D-1 including the compound according to Example 1 of the present invention.

Light-Emitting Elements D-2 and D-3 were manufactured through a process which is substantially the same as the process of manufacturing Light-Emitting Element D-1, except that the first layer was manufactured by using each of the compounds according to Examples 3 and 6 of the present invention.

Manufacture of Comparative Element 5

Comparative Element 5 was manufactured through a process which is substantially the same as the process of manufacturing Light-Emitting Element D-1, except that the host material of the first layer was prepared by using the compound according to Comparative Example 1, which is represented by Formula a.

Evaluation-4 of Power Efficiency and Lifespan of Light-Emitting Element

For each of Light-Emitting Element D-1 to D-3 and Comparative Element 5 thus prepared above, the power efficiency was measured by the method, which is substantially the same as in the experiment of measuring the power efficiency for Light-Emitting Elements A-1 to A-7, based on the value when the brightness was 500 cd/m² by using PR655 (trade name, manufactured by Photo Research Corp., USA) as a luminance meter.

Further, the lifespan of each of Light-Emitting Elements D-1 to D-3 and Comparative Element 5 was measured by the method which is substantially the same as in the experiment of evaluating the lifespan for Light-Emitting Elements A-1 to A-7 described above.

The results of the power efficiency and lifespan of each of Light-Emitting Elements D-1 to D-3 and Comparative Element 5 are shown in Table 24. In Table 24, the unit of the result of measuring the power efficiency is lm/W. In addition, in Table 24, $T_{75}$ means a time for brightness of the light-emitting element to become 75% as compared to the initial brightness, when the initial brightness of the light-emitting element is 1,000 cd/m².

TABLE 24

| Element No. | Power efficiency [lm/W] | Lifespan ($T_{75}$@85° C. [hr]) |
|---|---|---|
| Light-Emitting Element D-1 | 20.9 | 448 |
| Light-Emitting Element D-2 | 26.7 | 633 |
| Light-Emitting Element D-3 | 22.3 | 502 |
| Comparative Element 5 | 9.5 | 258 |

Referring to Table 24, it can be seen that the power efficiency of each of the light-emitting elements manufactured by using the compounds according to Examples 1, 3, and 6 of the present invention is at least 20.9 lm/W or more, and it is also possible to manufacture a light-emitting element which exhibits a power efficiency of about 26 lm/W or more, whereas the power efficiency of Comparative Element 5 is only about 9.5 lm/W. That is, it can be seen that the power efficiencies of the light-emitting elements including the compound according to the present invention are better than that of Comparative Element 5.

Further, the lifespan of each of the light-emitting elements manufactured by using the compounds according to Examples 1, 3, and 6 of the present invention is at least about 448 hours or more, and it can be seen that the lifespan of the light-emitting element is better than only about 258 hours as the lifespan of Comparative Element 5.

In addition, considering that the evaluation of lifespan characteristics of the light-emitting element was performed under the acceleration (harsh) condition of 85° C., through the fact that the lifespan characteristics of the light-emitting elements including the compounds according to Examples 1, 3, and 6 of the present invention are better than those of Comparative Element 5, it can be seen that the heat resistance of the light-emitting element manufactured by using the compound according to the present invention is good.

Manufacture of Light-Emitting Elements E-1 to E-3

NPB as a host material of a hole transporting layer was deposited at a rate of 1 Å/sec, and simultaneously, the P-type dopant (HAT-CN) represented by Formula 12 was co-deposited at a ratio of about 5 parts by weight based on 100 parts by weight of the host material, on a first electrode formed of indium tin oxide (ITO), thereby forming a first layer having a thickness of 100 Å. The compound according to Example 2 was deposited to have a thickness of 300 Å on the first layer, thereby forming a second layer. mCBP represented by Formula 13 and Ir(ppy)₃ represented by Formula 14 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, Bphen represented by Formula 15 and Alq3 represented by Formula 16 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by Formula 17.

A second electrode was formed on the electron injecting layer by using an aluminum thin film having a thickness of 1,000 Å, thereby manufacturing Light-Emitting Element E-1 including the compound according to Example 2 of the present invention.

Light-Emitting Elements E-2 and E-3 were manufactured through a process which is substantially the same as the process of manufacturing Light-Emitting Element E-1, except that the second layer was manufactured by using each of the compounds according to Examples 5 and 7 of the present invention.

Manufacture of Comparative Element 6

Comparative Element 6 was manufactured through a process which is substantially the same as the process of manufacturing Light-Emitting Element E-1, except that the second layer was manufactured by using the compound according to Comparative Example 1, which is represented by Formula a.

Evaluation-5 of Power Efficiency and Lifespan of Light-Emitting Element

For each of Light-Emitting Element E-1 to E-3 and Comparative Element 6 thus prepared above, the power efficiency was measured by the method, which is substantially the same as in the experiment of measuring the power efficiency for Light-Emitting Elements A-1 to A-7, based on the value when the brightness was 500 cd/m² by using PR655 (trade name, manufactured by Photo Research Corp., USA) as a luminance meter.

Further, the lifespan of each of Light-Emitting Elements E-1 to E-3 and Comparative Element 6 was measured by the method which is substantially the same as in the experiment of evaluating the lifespan for Light-Emitting Elements A-1 to A-7 described above.

The results of the power efficiency and lifespan of each of Light-Emitting Elements E-1 to E-3 and Comparative Element 6 are shown in Table 25. In Table 25, the unit of the result of measuring the power efficiency is lm/W. In addition, in Table 25, $T_{75}$ means a time for brightness of the light-emitting element to become 75% as compared to the initial brightness, when the initial brightness of the light-emitting element is 1,000 cd/m².

TABLE 25

| Element No. | Power efficiency [lm/W] | Lifespan ($T_{75}$@85° C. [hr]) |
|---|---|---|
| Light-Emitting Element E-1 | 31.7 | 731 |
| Light-Emitting Element E-2 | 23.1 | 528 |
| Light-Emitting Element E-3 | 23.9 | 542 |
| Comparative Element 6 | 9.1 | 220 |

Referring to Table 25, it can be seen that the power efficiency of each of the light-emitting elements manufactured by using the compounds according to Examples 2, 5, and 7 of the present invention is at least 23.1 lm/W or more, and it is also possible to manufacture a light-emitting element which exhibits a power efficiency of about 31 lm/W or more, whereas the power efficiency of Comparative Element 6 is only about 9.1 lm/W. That is, it can be seen that the power efficiencies of the light-emitting elements including the compound according to the present invention are better than that of Comparative Element 6.

Further, the lifespan of each of the light-emitting elements manufactured by using the compounds according to Examples 2, 5, and 7 of the present invention is at least about 528 hours or more, and it can be seen that the lifespan of the light-emitting element is better than only about 220 hours as the lifespan of Comparative Element 6.

In addition, considering that the evaluation of lifespan characteristics of the light-emitting element was performed under the acceleration (harsh) condition of 85° C., through the fact that the lifespan characteristics of the light-emitting elements including the compounds according to Examples 2, 5, and 7 of the present invention are better than those of Comparative Element 6, it can be seen that the heat resistance of the light-emitting element manufactured by using the compound according to the present invention is good.

According to those described above, it is possible to manufacture a light-emitting element, of which the power efficiency, lifespan, and thermal stability have been improved, by using the novel compound according to the present invention.

Manufacture of Light-Emitting Elements F-1 to F-4

NPB as a host material of a hole transporting layer was deposited at a rate of 1 Å/sec, and simultaneously, the P-type dopant (HAT-CN) represented by Formula 12 was co-deposited at a ratio of about 5 parts by weight based on 100 parts by weight of the host material NPB, on a first electrode formed of indium tin oxide (ITO), thereby forming a first layer having a thickness of 100 Å. NPB was deposited to have a thickness of 300 Å on the first layer, thereby forming a second layer. mCBP represented by Formula 13 and Ir(ppy)$_3$ represented by Formula 14 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, the compound according to Example 8 was deposited to have a thickness of about 400 Å on the blocking layer, thereby forming an electron transporting layer. Subsequently, an electron injecting layer having a thickness of about 10 Å was formed on the electron transporting layer by using Liq represented by Formula 17.

A second electrode was formed on the electron injecting layer by using an aluminum thin film having a thickness of 1,000 Å, thereby manufacturing Light-Emitting Element F-1 including the compound according to Example 8 of the present invention.

Light-Emitting Elements F-2 to F-4 were manufactured through a process which is substantially the same as the process of manufacturing Light-Emitting Element F-1, except that the electron transporting layer was manufactured by using each of the compounds according to Examples 9 to 11 of the present invention.

Manufacture of Comparative Elements 7 and 8

Comparative Element 7 was manufactured through a process which is substantially the same as the process of manufacturing Light-Emitting Element F-1, except that the electron transporting layer was manufactured by using the compound according to Comparative Example 3, which is represented by Formula c.

Furthermore, Comparative Element 8 was manufactured through a process which is substantially the same as the process of manufacturing Light-Emitting Element F-1, except that the electron transporting layer was manufactured by using the compound according to Comparative Example 4, which is represented by Formula d.

Evaluation-6 of Power Efficiency and Lifespan of Light-Emitting Element

For each of Light-Emitting Elements F-1 to F-4 and Comparative Elements 7 and 8 thus prepared above, the power efficiency was measured by the method, which is substantially the same as in the experiment of measuring the power efficiency for Light-Emitting Elements A-1 to A-7, based on the value when the brightness was 500 cd/m$^2$ by using PR655 (trade name, manufactured by Photo Research Corp., USA) as a luminance meter.

Further, the lifespan of each of Light-Emitting Elements F-1 to F-4 and Comparative Elements 7 and 8 was measured by the method which is substantially the same as in the experiment of evaluating the lifespan for Light-Emitting Elements A-1 to A-7 described above.

The results of the power efficiency and lifespan of each of Light-Emitting Elements F-1 to F-4 and Comparative Elements 7 and 8 are shown in Table 26. In Table 26, the unit of the result of measuring the power efficiency is lm/W. In addition, in Table 26, T$_{75}$ means a time for brightness of the light-emitting element to become 75% as compared to the initial brightness, when the initial brightness of the light-emitting element is 1,000 cd/m$^2$.

TABLE 26

| Element No. | Power efficiency [lm/W] | Lifespan (T$_{75}$@85° C. [hr]) |
|---|---|---|
| Light-Emitting Element F-1 | 28.1 | 648 |
| Light-Emitting Element F-2 | 30.2 | 690 |
| Light-Emitting Element F-3 | 26.8 | 618 |
| Light-Emitting Element F-4 | 27.7 | 641 |
| Comparative Element 7 | 21.8 | 507 |
| Comparative Element 8 | 19.6 | 459 |

Referring to Table 26, it can be seen that the power efficiency of each of the light-emitting elements manufactured by using the compounds according to Examples 8 to 11 of the present invention is at least 26.8 lm/W or more, and it is also possible to manufacture a light-emitting element which exhibits a power efficiency of about 30 lm/W or more, whereas the power efficiency of Comparative Element 7 is only about 21.8 lm/W, and the power efficiency of Comparative Element 8 is only about 19.6 lm/W.

In addition, the lifespan of each of the light-emitting elements manufactured by using the compounds according to Examples 8 to 11 of the present invention is at least about 618 hours or more, and it can be seen that when the lifespan is compared to 507 hours and 459 hours, which are the lifespan of Comparative Elements 7 and 8, respectively, the lifespan of the light-emitting element including the compound according to the present invention is better than those of Comparative Elements 7 and 8.

Furthermore, considering that the evaluation of lifespan characteristics of the light-emitting element was performed under the acceleration (harsh) condition of 85° C., through the fact that the lifespan characteristics of the light-emitting elements including the compounds according to Examples 8 to 11 of the present invention are better than those of Comparative Elements 7 and 8, it can be seen that the heat resistance of the light-emitting element manufactured by using the compound according to the present invention is good.

According to those described above, it is possible to manufacture a light-emitting element, of which the power efficiency, lifespan, and thermal stability have been improved, by using the novel compound according to the present invention.

Manufacture of Light-Emitting Elements G-1 to G-4

NPB as a host material of a hole transporting layer was deposited at a rate of 1 Å/sec, and simultaneously, the P-type dopant (HAT-CN) represented by Formula 12 was co-deposited at a ratio of about 5 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. mCBP represented by Formula 13 and Ir(ppy)$_3$ represented by Formula 14 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, the compound represented by Formula 8 and Liq represented by Formula 17 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by Formula 17.

A second electrode was formed on the electron injecting layer by using an aluminum thin film having a thickness of 1,000 Å, thereby manufacturing Light-Emitting Element G-1 including the compound according to Example 8 of the present invention.

Light-Emitting Elements G-2 to G-4 were manufactured through a process which is substantially the same as the process of manufacturing Light-Emitting Element G-1, except that the electron transporting layer was manufactured by performing co-deposition with Liq using each of the compounds according to Examples 9 to 11 of the present invention.

Manufacture of Comparative Elements 9 and 10

Comparative Element 9 was manufactured through a process which is substantially the same as the process of manufacturing Light-Emitting Element G-1, except that the electron transporting layer was manufactured by performing co-deposition with Liq using the compound according to Comparative Example 3, which is represented by Formula c.

Further, Comparative Element 10 was manufactured through a process which is substantially the same as the process of manufacturing Light-Emitting Element G-1, except that the electron transporting layer was manufactured by performing co-deposition with Liq using the compound according to Comparative Example 4, which is represented by Formula d.

Evaluation-7 of Power Efficiency and Lifespan of Light-Emitting Element

For each of Light-Emitting Element G-1 to G-4 and Comparative Elements 9 and 10 thus prepared above, the power efficiency was measured by the method, which is substantially the same as in the experiment of measuring the power efficiency for Light-Emitting Elements A-1 to A-7, based on the value when the brightness was 500 cd/m$^2$ by using PR655 (trade name, manufactured by Photo Research Corp., USA) as a luminance meter.

Further, the lifespan of each of Light-Emitting Elements G-1 to G-4 and Comparative Elements 9 and 10 was measured by the method which is substantially the same as in the experiment of evaluating the lifespan for Light-Emitting Elements A-1 to A-7 described above.

The results of the power efficiency and lifespan of each of Light-Emitting Elements G-1 to G-4 and Comparative Elements 9 and 10 are shown in Table 27. In Table 27, the unit of the result of measuring the power efficiency is lm/W. In addition, in Table 27, $T_{75}$ means a time for brightness of the light-emitting element to become 75% as compared to the initial brightness, when the initial brightness of the light-emitting element is 1,000 cd/m$^2$.

TABLE 27

| Element No. | Power efficiency [lm/W] | Lifespan ($T_{75}$@85° C. [hr]) |
|---|---|---|
| Light-Emitting Element G-1 | 31.1 | 716 |
| Light-Emitting Element G-2 | 33.2 | 762 |
| Light-Emitting Element G-3 | 29.6 | 681 |
| Light-Emitting Element G-4 | 30.7 | 707 |
| Comparative Element 9 | 26.9 | 616 |
| Comparative Element 10 | 21.4 | 503 |

Referring to Table 27, it can be seen that the power efficiency of each of the light-emitting elements manufactured by using the compounds according to Examples 8 to 11 of the present invention is at least 29.6 lm/W or more, whereas the power efficiencies of Comparative Elements 9 and 10 are only about 26.9 lm/W and about 21.4 lm/W, respectively. Accordingly, it can be seen that the power efficiencies of the light-emitting elements including the compound according to the present invention are better than those of Comparative Elements 9 and 10.

In addition, the lifespan of each of the light-emitting elements manufactured by using the compounds according to Examples 8 to 11 of the present invention is at least about 681 hours or more, and it can be seen that the lifespan of the light-emitting element including the compound according to the present invention is better than 616 hours and 503 hours, which are the lifespan of Comparative Elements 9 and 10, respectively.

Furthermore, considering that the evaluation of lifespan characteristics of the light-emitting element was performed under the acceleration (harsh) condition of 85° C., through the fact that the lifespan characteristics of the light-emitting elements including the compounds according to Examples 8 to 11 of the present invention are better than those of Comparative Elements 9 and 10, it can be seen that the heat resistance of the light-emitting element manufactured by using the compound according to the present invention is good.

According to those described above, it is possible to manufacture a light-emitting element, of which the power efficiency, lifespan, and thermal stability have been improved, by using the novel compound according to the present invention.

Manufacture of Light-Emitting Elements H-1 to H-3

NPB as a host material of a hole transporting layer was deposited at a rate of 1 Å/sec, and simultaneously, the P-type dopant (HAT-CN) represented by Formula 12 was co-deposited at a ratio of about 5 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. The compound represented by Example 12 and Ir(ppy)$_3$ represented by Formula 14 were co-deposited at a weight ratio of 100:9 on the second layer, thereby forming a light-emitting layer having a thickness of about 300 Å, and mCBP represented by Formula 13 was deposited again to have a thickness of about 50 Å on the light-emitting layer, thereby forming a blocking layer.

And then, Bphen represented by Formula 15 and Alq3 represented by Formula 16 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by Formula 17.

A second electrode was formed on the electron transporting layer by using an aluminum thin film having a thickness of 1,000 Å, thereby manufacturing Light-Emitting Element H-1 including the compound according to Example 12 of the present invention.

Light-Emitting Elements H-2 and H-3 were manufactured through a process which is substantially the same as the process of manufacturing Light-Emitting Element H-1, except that the light-emitting layer was manufactured by performing the co-deposition with Ir(ppy)$_3$ using each of the compounds according to Examples 3 and 14 of the present invention.

Manufacture of Comparative Element 11

Comparative Element 11 was manufactured through a process which is substantially the same as the process of manufacturing Light-Emitting Element H-1, except that the light-emitting layer was manufactured by performing the co-deposition with Ir(ppy)$_3$ using the compound according to Comparative Example 5, which is represented by Formula e.

Evaluation-8 of Power Efficiency, Color Coordinate, and Lifespan of Light-Emitting Element For each of Light-Emitting Element H-1 to H-3 and Comparative Element 11 thus prepared above, the power efficiency and the color coordinate were measured by the method, which is substantially the same as in the experiment of measuring the power efficiency for Light-Emitting Elements A-1 to A-7, based on the value when the brightness was 500 cd/m$^2$ by using PR655 (trade name, manufactured by Photo Research Corp., USA) as a luminance meter.

Further, the lifespan of each of Light-Emitting Elements H-1 to H-3 and Comparative Element 11 was measured by the method which is substantially the same as in the experiment of evaluating the lifespan for Light-Emitting Elements A-1 to A-7 described above.

The results of the power efficiency, color coordinate, and lifespan characteristics of each of Light-Emitting Elements H-1 to H-3 and Comparative Element 11 are shown in Table 28. In Table 28, the unit of the result of measuring the power efficiency is lm/W. In addition, in Table 28, T$_{75}$ means a time for brightness of the light-emitting element to become 75% as compared to the initial brightness, when the initial brightness of the light-emitting element is 1,000 cd/m$^2$. Furthermore, in Table 28, the color coordinate is in accordance with the CIE1931 chromaticity coordinate system established by the International Commission on Illumination (CIE) in 1931.

TABLE 28

| Element No. | Power efficiency [lm/W] | Color Coordinate (x, y) | Lifespan (T$_{75}$@85° C. [hr]) |
|---|---|---|---|
| Light-Emitting Element H-1 | 20.4 | (0.26, 0.62) | 469 |
| Light-Emitting Element H-2 | 22.2 | (0.27, 0.63) | 512 |
| Light-Emitting Element H-3 | 23.4 | (0.28, 0.63) | 540 |
| Comparative Element 11 | 18.7 | (0.25, 0.60) | 426 |

Referring to Table 28, it can be seen that the power efficiency of each of the light-emitting elements manufactured by using the compounds according to Examples 12 to 14 of the present invention is at least 20.4 lm/W or more, and it is also possible to manufacture a light-emitting element which exhibits a power efficiency of about 23 lm/W or more, whereas the power efficiency of Comparative Element 11 is only about 18.7 lm/W. Accordingly, it can be seen that the power efficiency of the light-emitting element including the compound according to the present invention is better than that of Comparative Element 11.

Further, the lifespan of each of the light-emitting elements manufactured by using the compounds according to Examples 12 to 14 of the present invention is at least about 469 hours or more, and it can be seen that when the lifespan is compared to about 426 hours as the lifespan of Comparative Element 11, the lifespan of the light-emitting elements including the compounds according to the present invention is good.

Meanwhile, it can be seen that the color coordinate (x, y) of each of the light-emitting elements manufactured by using the compounds according to Examples 12 to 14 of the present invention exhibits (0.26, 0.62), (0.27, 0.63), and (0.28, 0.63). As compared to the color coordinate (x, y) of Comparative Element 11 which is (0.25, 0.60), it can be seen that the color coordinate of the light-emitting elements according to the present invention is at a level which is substantially similar to the color coordinate of Comparative Element 11. That is, it can be seen that the compounds according to the present invention do not emit light in the light-emitting layer of the light-emitting element, and serve as a host of the light-emitting layer which helps to enhance the light-emitting efficiency of Ir(ppy)$_3$ represented by Formula 14 at a level similar to mCBP.

Furthermore, considering that the evaluation of lifespan characteristics of the light-emitting element was performed under the acceleration (harsh) condition of 85° C., through the fact that the lifespan characteristics of the light-emitting elements including the compounds according to Examples 12 to 14 of the present invention are better than those of Comparative Element 11, it can be seen that the heat resistance of the light-emitting element manufactured by using the compound according to the present invention is good.

According to those described above, it is possible to manufacture a light-emitting element, of which the power efficiency, lifespan, and thermal stability have been improved, by using the novel compound according to the present invention.

What is claimed is:

1. A compound represented by the following Formula 1:

<Formula 1>

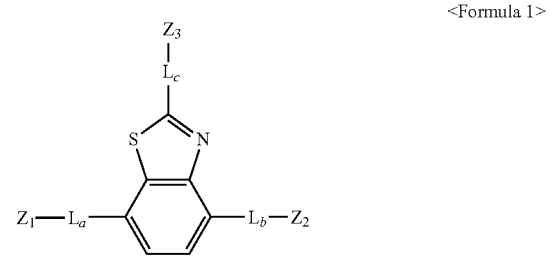

in which, $Z_1$ and $Z_2$ are each independently represented by Formula 3,

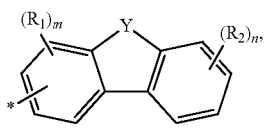

$Z_3$ represents an aryl group having 6 to 60 carbon atoms, or any one structure of the following Formulae 2 to 6, <Formula 2>

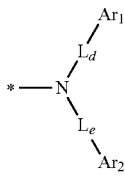

<Formula 3>

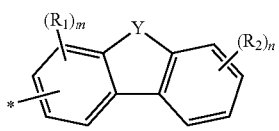

<Formula 4>

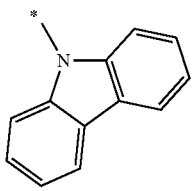

<Formula 5>

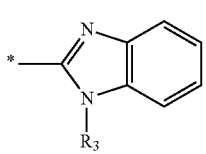

<Formula 6>

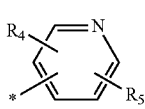

Y represents S, O, or N-$L_f$-$Ar_3$, $L_a$, $L_b$, $L_c$, $L_d$, $L_e$, and $L_f$ each independently represent *-$L_1$-$L_2$-$L_3$-$L_4$-*, $L_1$, $L_2$, $L_3$, and $L_4$ each independently represent a single bond, —O—, —S—, a linear or branched alkylene group (—(CH$_2$)$_j$—, here, j is an integer of 1 to 60) having 1 to 60 carbon atoms, an arylene group having 6 to 60 carbon atoms, a heteroarylene group having 2 to 60 carbon atoms, an alkenylene group having 2 to 60 carbon atoms, an alkynylene group having 2 to 60 carbon atoms, a cycloalkylene group having 3 to 60 carbon atoms, a heterocycloalkylene group 2 to 60 carbon atoms, an adamantylene group, or a bicycloalkylene group having 7 to 60 carbon atoms, $Ar_1$, $Ar_2$, and $Ar_3$ each independently represent hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, an alkenyl group having 2 to 60 carbon atoms, or an alkynyl group having 2 to 60 carbon atoms, $R_1$ and $R_2$ each independently represent an aryl group having 6 to 60 carbon atoms, a heteroaryl group having 2 to 60 carbon atoms, an alkenyl group having 2 to 60 carbon atoms, or an alkynyl group having 2 to 60 carbon atoms, $R_3$, $R_4$, and $R_5$ each independently represent an alkyl group having 1 to 3 carbon atoms, or an aryl group having 6 to 30 carbon atoms, m and n each independently represent an integer of 0 to 3, and the hydrogen atoms of $Z_1$, $Z_2$, $Z_3$, $L_a$, $L_b$, and $L_c$ of Formula 1 are each independently unsubstituted or substituted with an alkyl group having 1 to 8 carbon atoms, an alkoxy group having 1 to 8 carbon atoms, a halogen group, a cyano group, or a trimethylsilyl group.

2. The compound of claim 1, wherein $Z_3$ represents any one of the following Substituents 5-1 to 5-9, <Substituent 5-1>

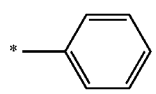

<Substituent 5-2>

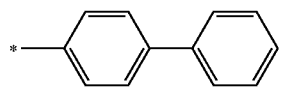

<Substituent 5-3>

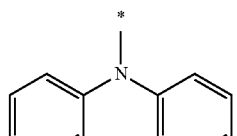

<Substituent 5-4>

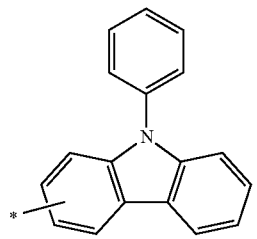

<Substituent 5-5>

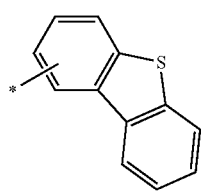

<Substituent 5-6>

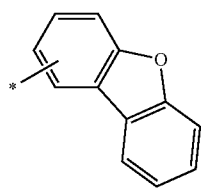

<Substituent 5-7>

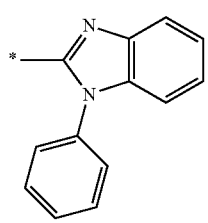

<Substituent 5-8>

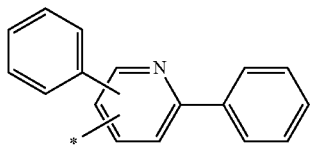

<Substituent 5-9>

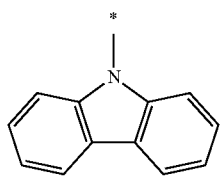

$Z_1$ and $Z_2$ each independently represent any one of the following Substituents 6-1 to 6-3, <Substituent 6-1>

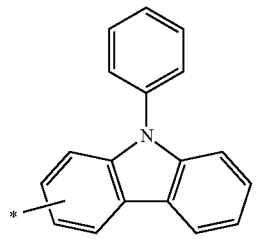

<Substituent 6-2>

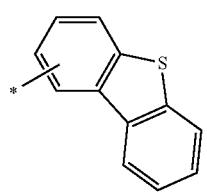

<Substituent 6-3>

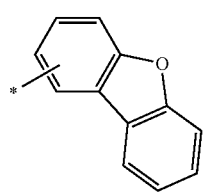

$L_a$, $L_b$, and $L_c$ each independently represent a single bond, or any one of the following Substituents 7-1 and 7-2, <Substituent 7-1>

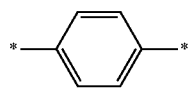

<Substituent 7-2>

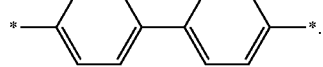

3. The compound of claim 1, wherein the compound is selected from the group consisting of:

<Compound 8-1>

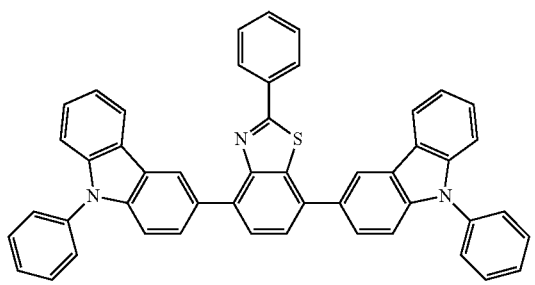

<Compound 8-2>

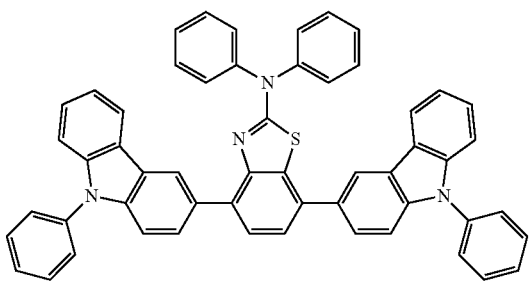

-continued
<Compound 8-3>
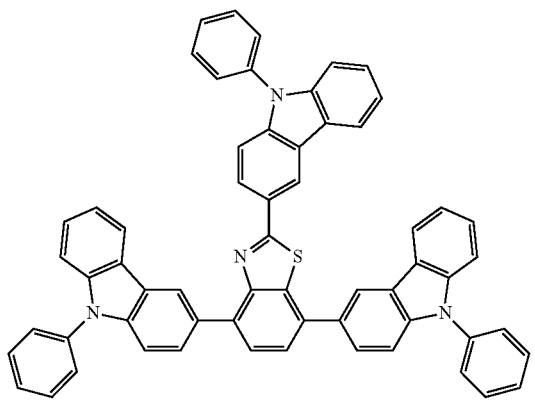
<Compound 8-4>
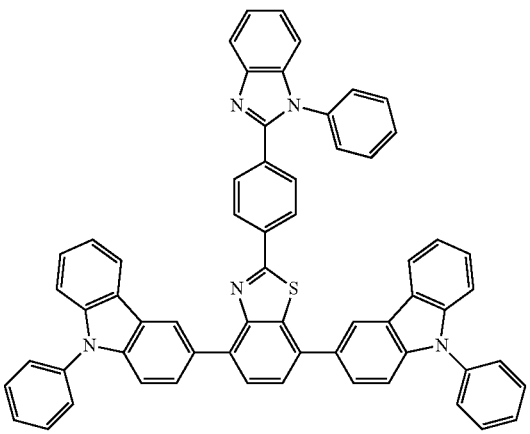
<Compound 8-5>
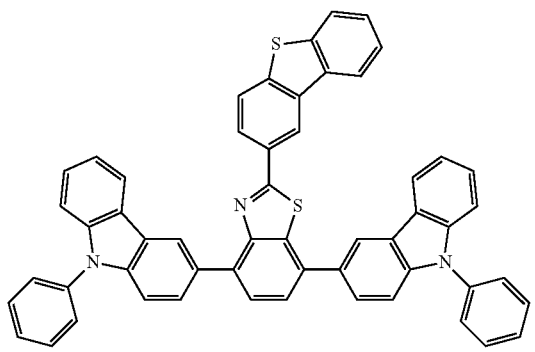
<Compound 8-6>
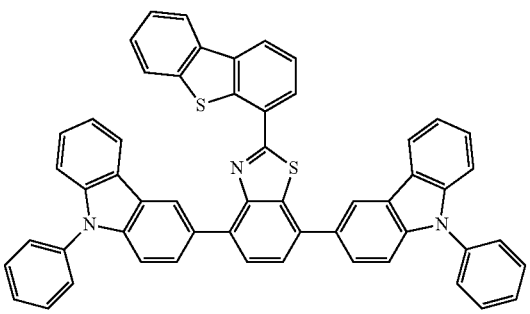
<Compound 8-7>
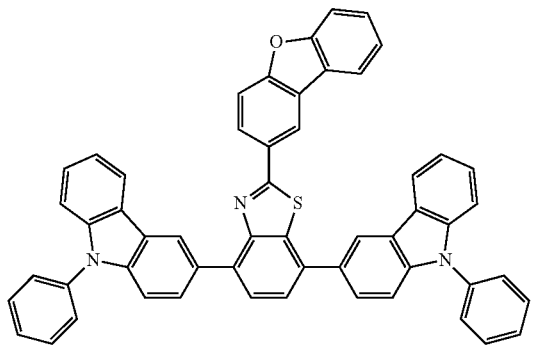
<Compound 8-8>
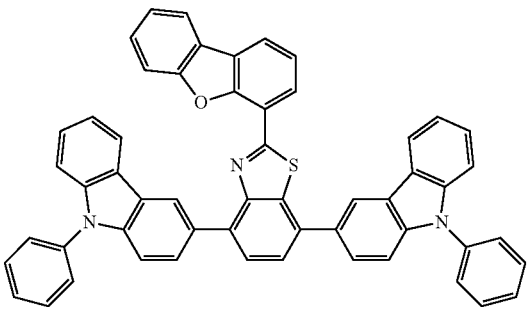
<Compound 8-9>
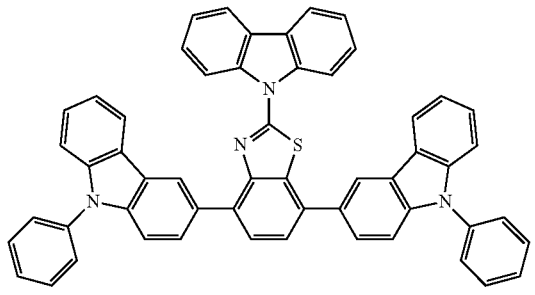
<Compound 8-10>
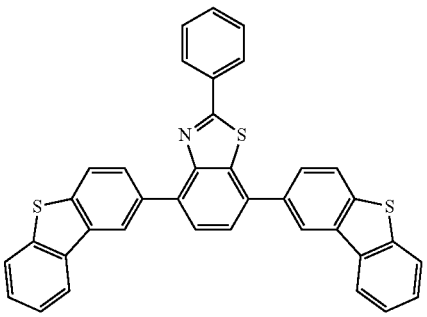

<Compound 8-11>
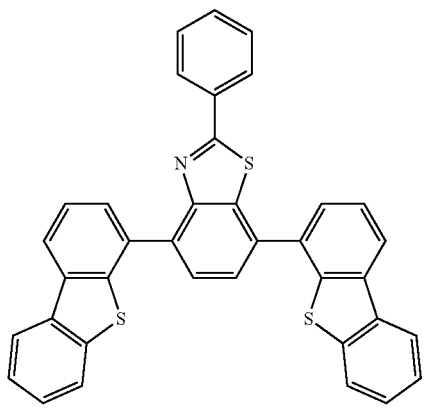
<Compound 8-12>
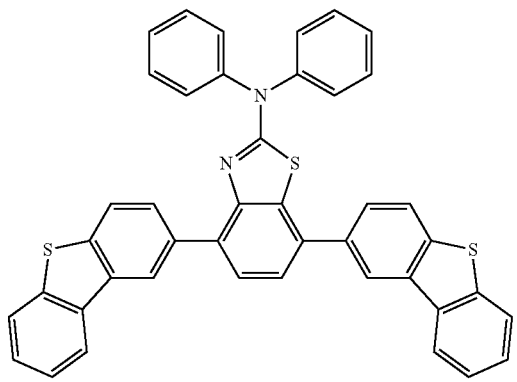
<Compound 8-13>
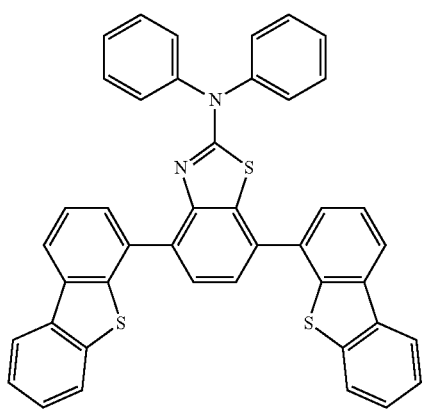
<Compound 8-14>
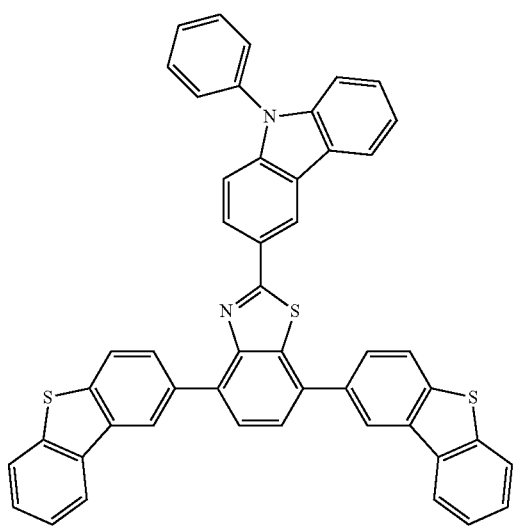
<Compound 8-15>
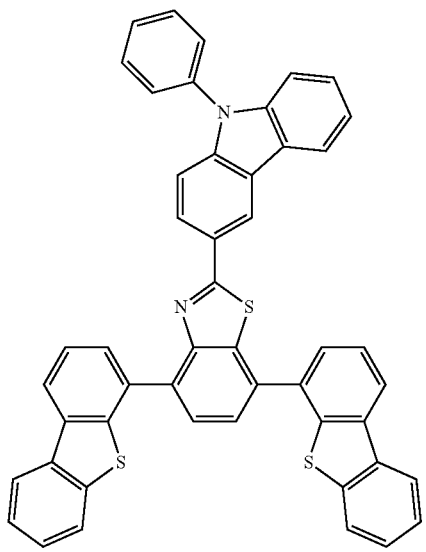
<Compound 8-16>
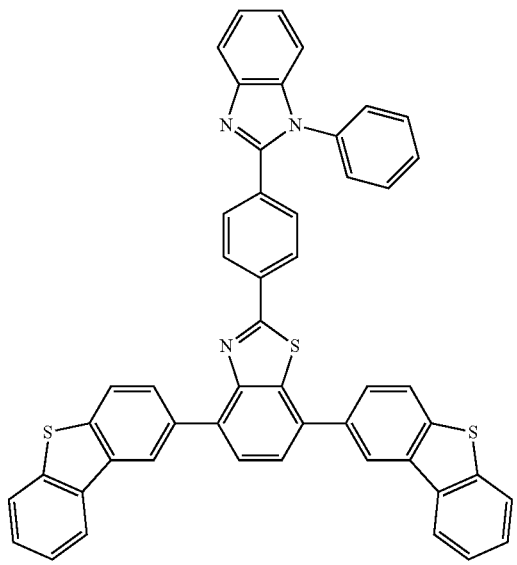

<Compound 8-17>
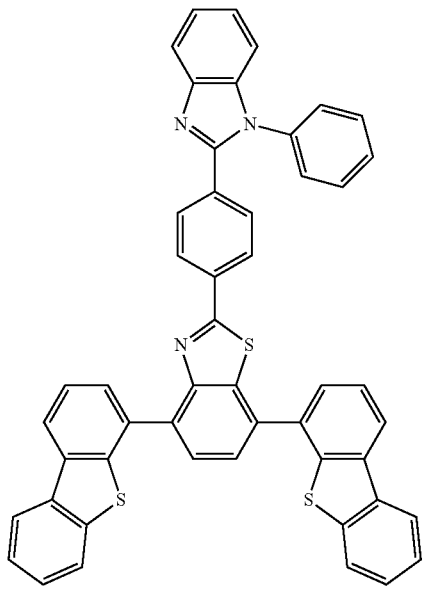
<Compound 8-18>
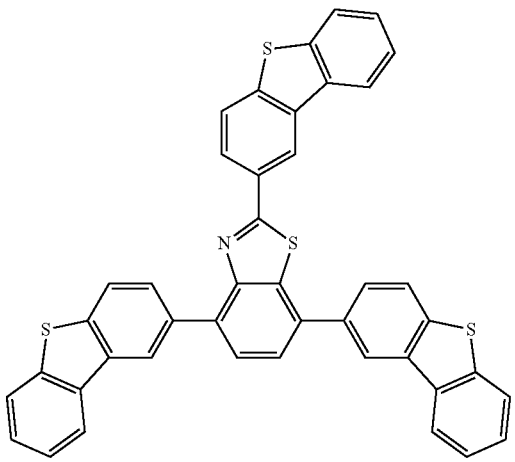
<Compound 8-19>
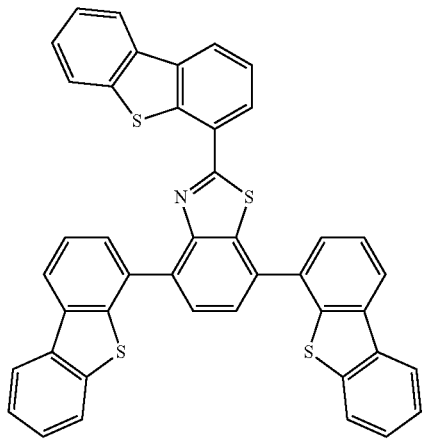
<Compound 8-20>
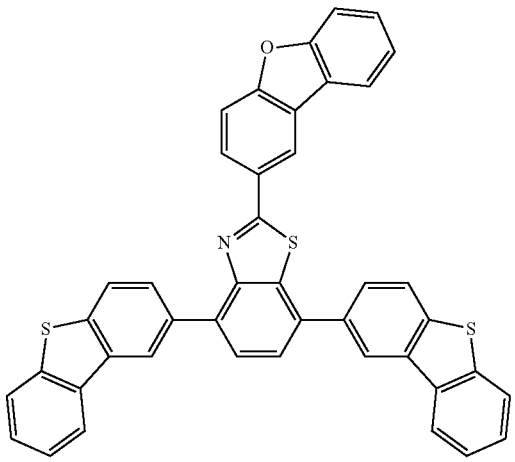
<Compound 8-21>
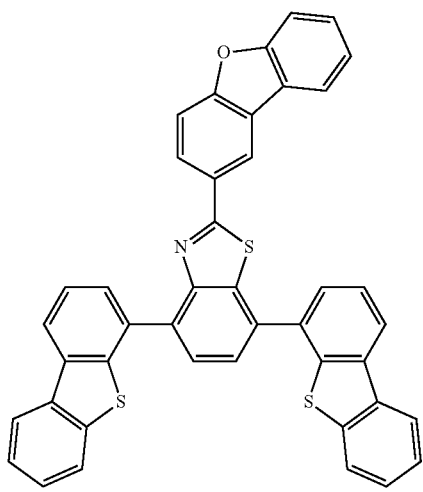
<Compound 8-22>
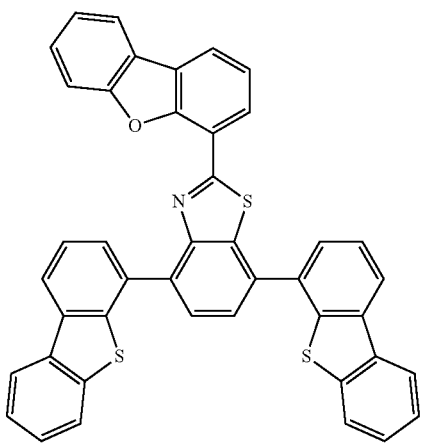

<Compound 8-23>
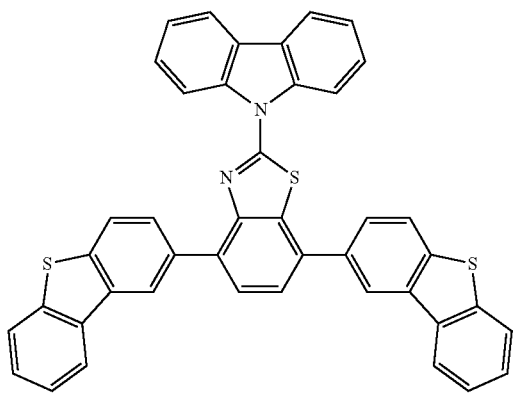
<Compound 8-24>
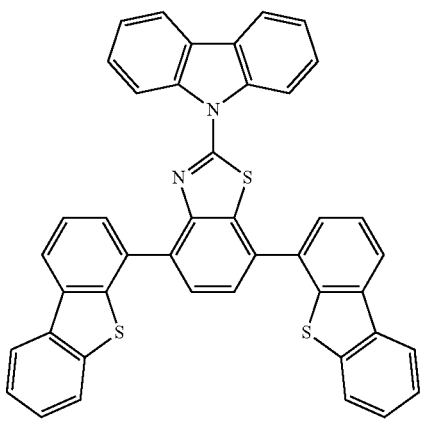
<Compound 8-25>
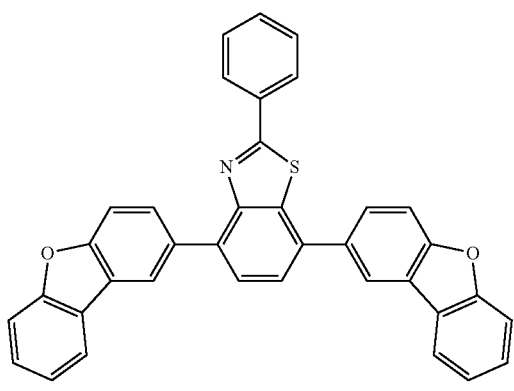
<Compound 8-26>
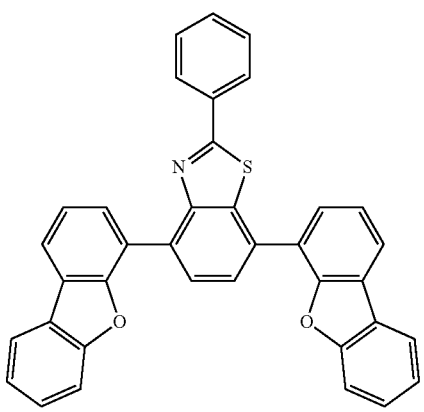
<Compound 8-27>
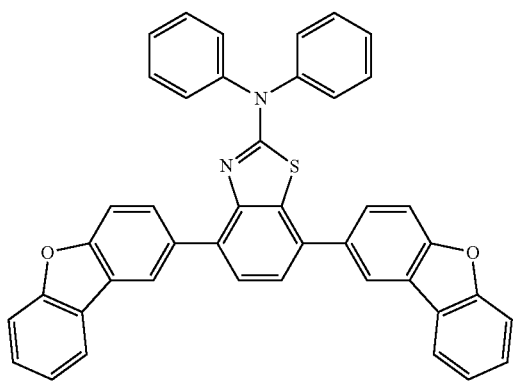
<Compound 8-28>
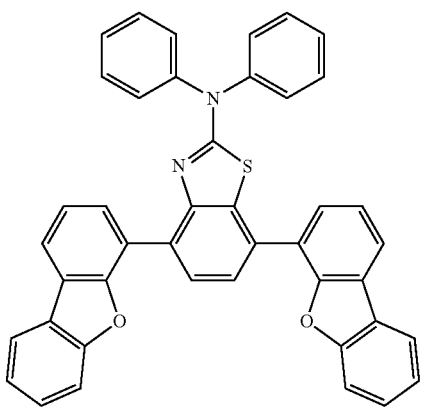

-continued
<Compound 8-29>
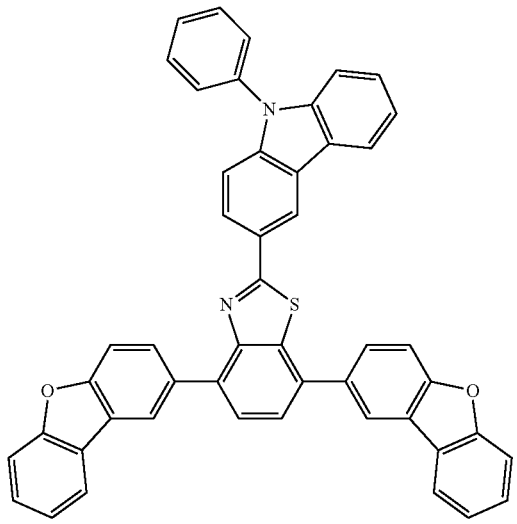
<Compound 8-30>
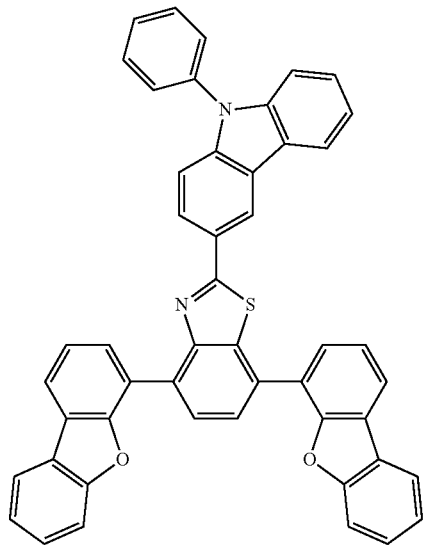
<Compound 8-31>
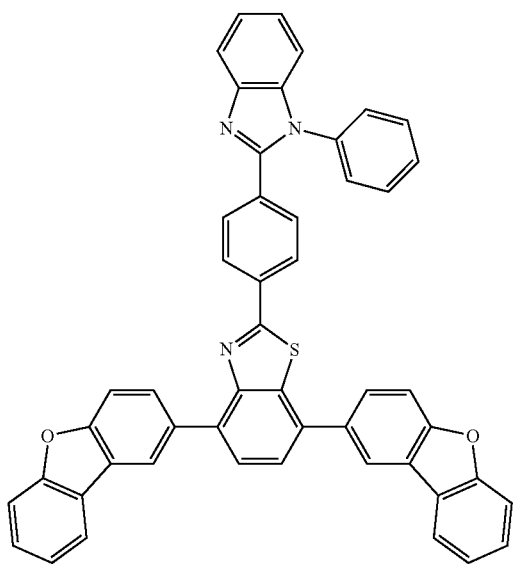
<Compound 8-32>
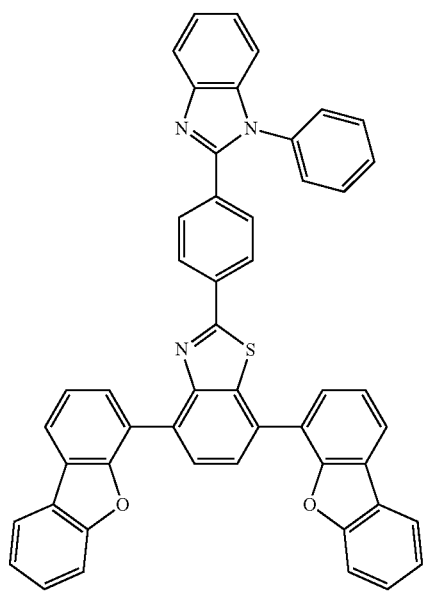

-continued
<Compound 8-33>
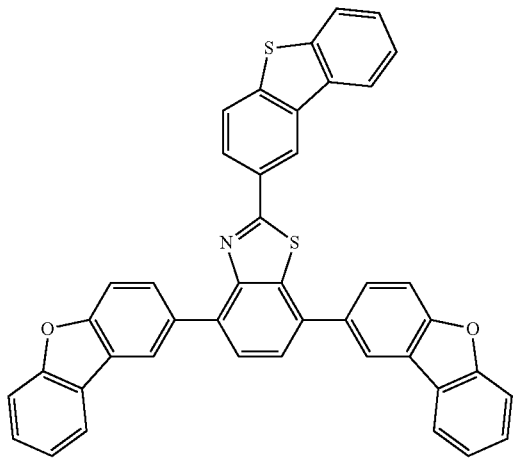
<Compound 8-34>
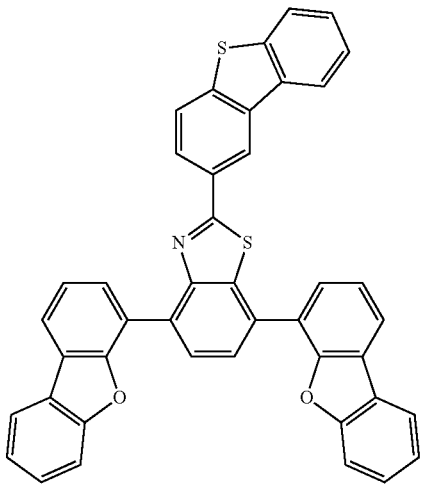
<Compound 8-35>
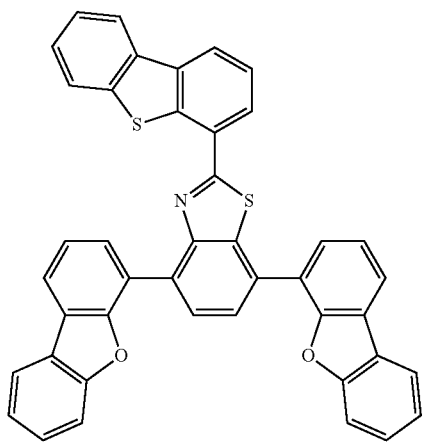
<Compound 8-36>
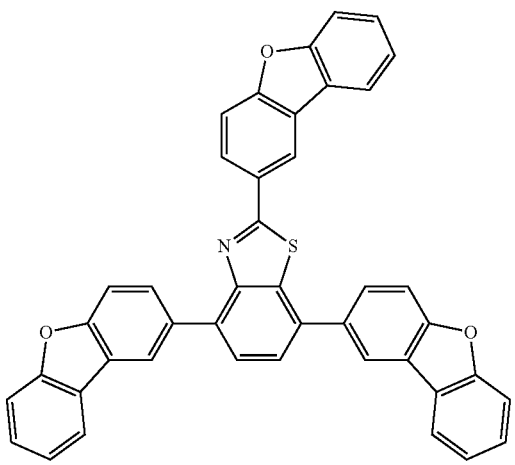
<Compound 8-37>
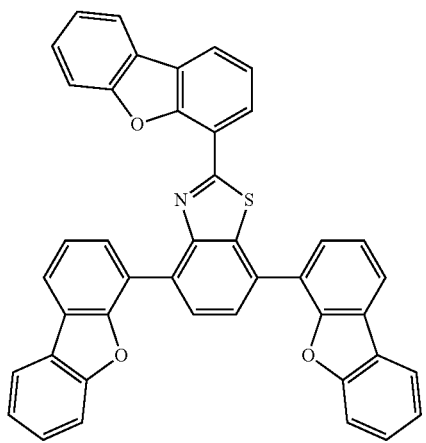
<Compound 8-38>
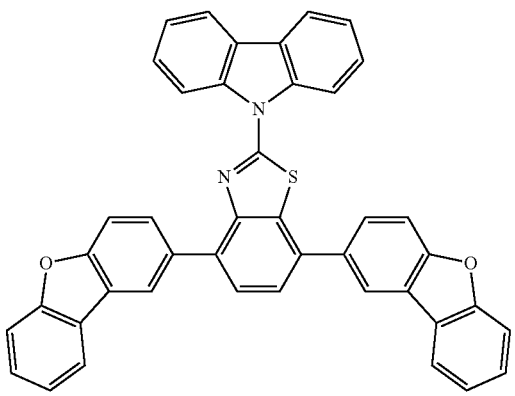

<Compound 8-39>
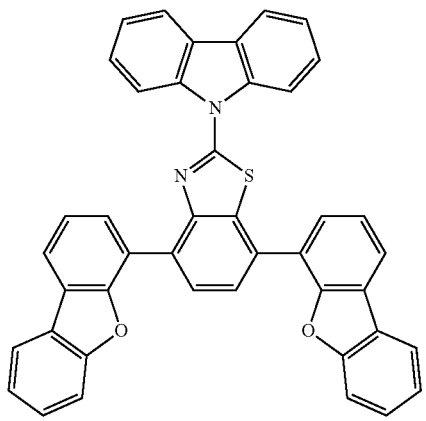
<Compound 8-40>
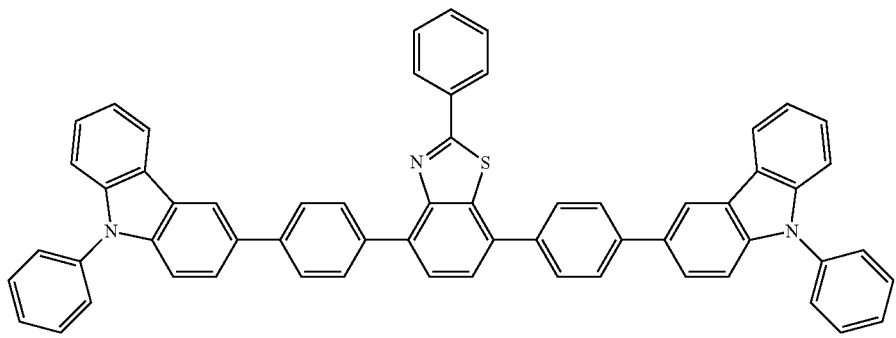
<Compound 8-41>
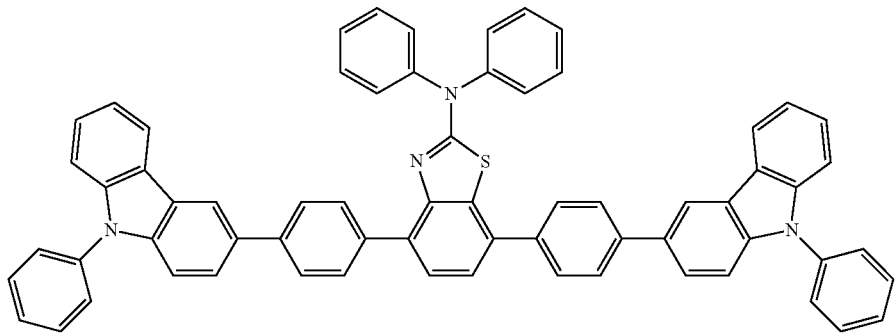
<Compound 8-42>
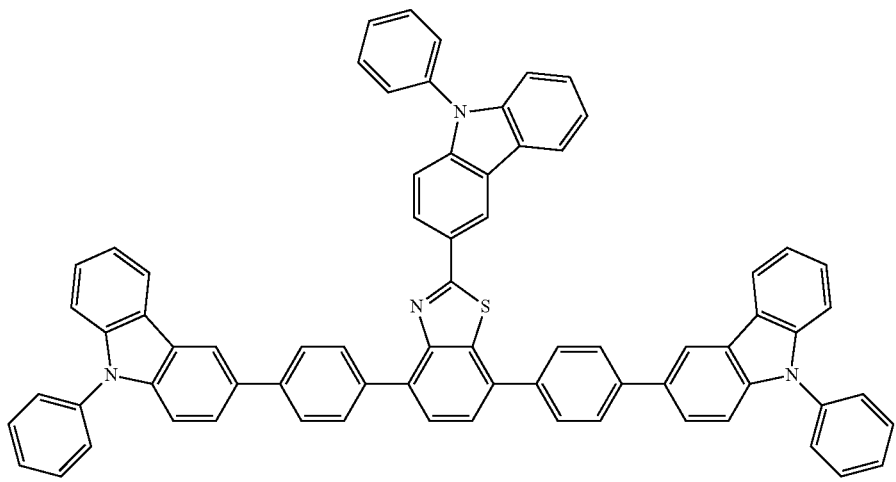

-continued
<Compound 8-43>
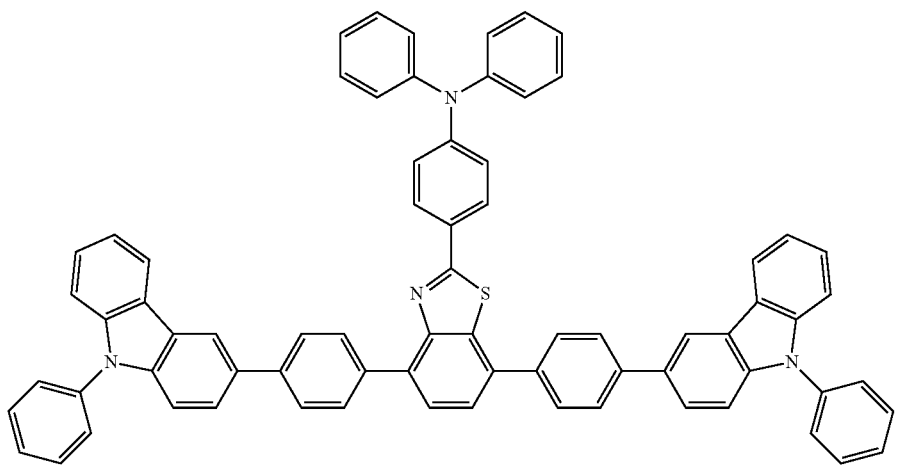
<Compound 8-44>
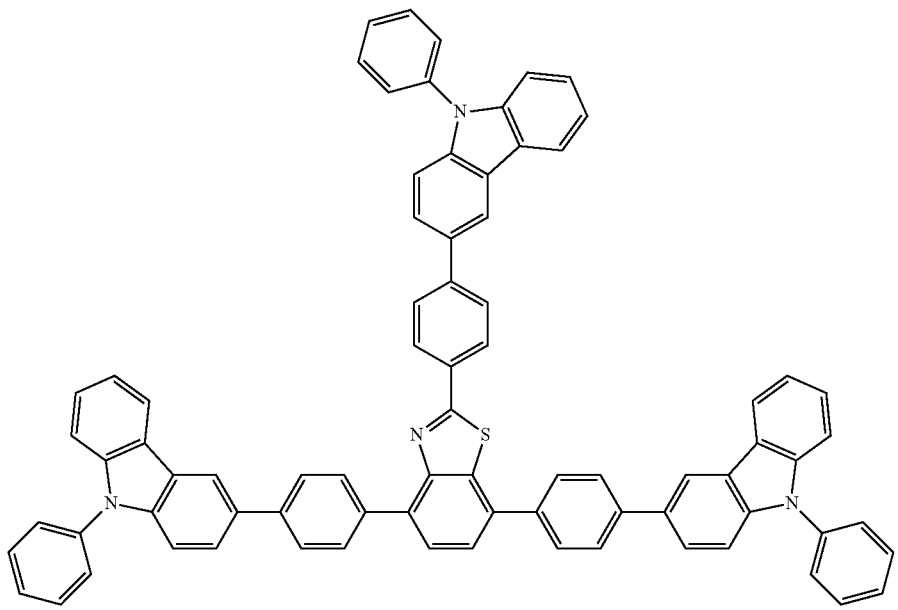
<Compound 8-45>
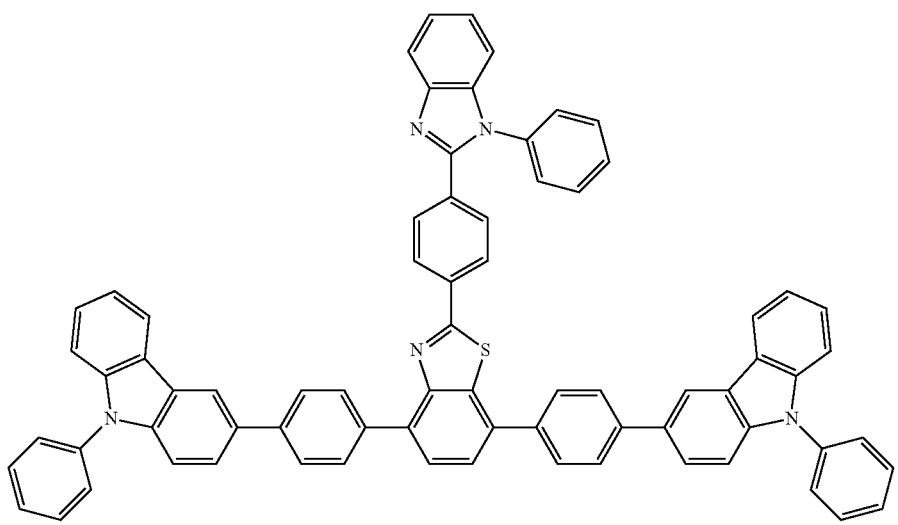

<Compound 8-46>
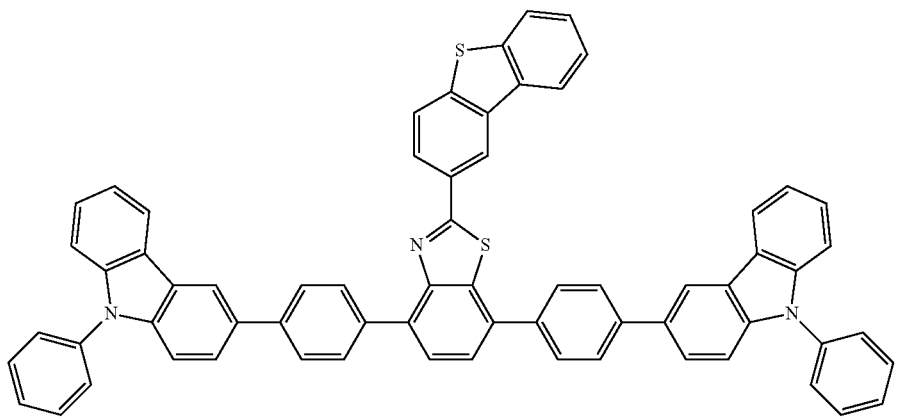
<Compound 8-47>
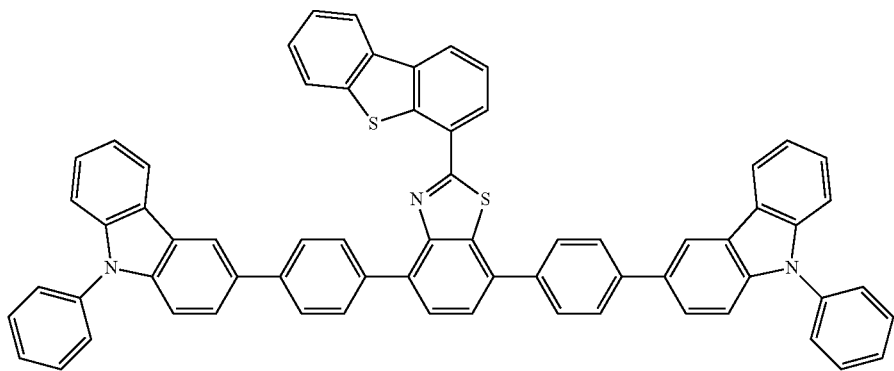
<Compound 8-48>
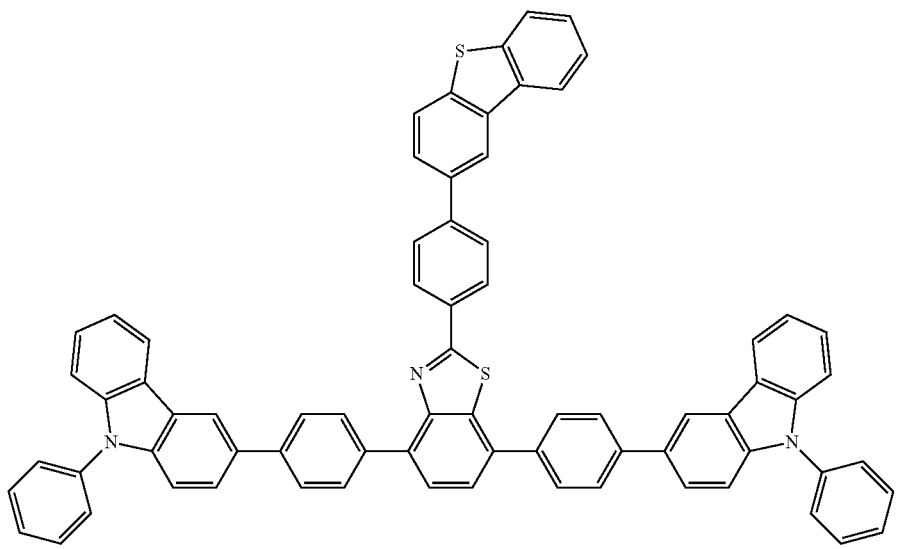

<Compound 8-49>
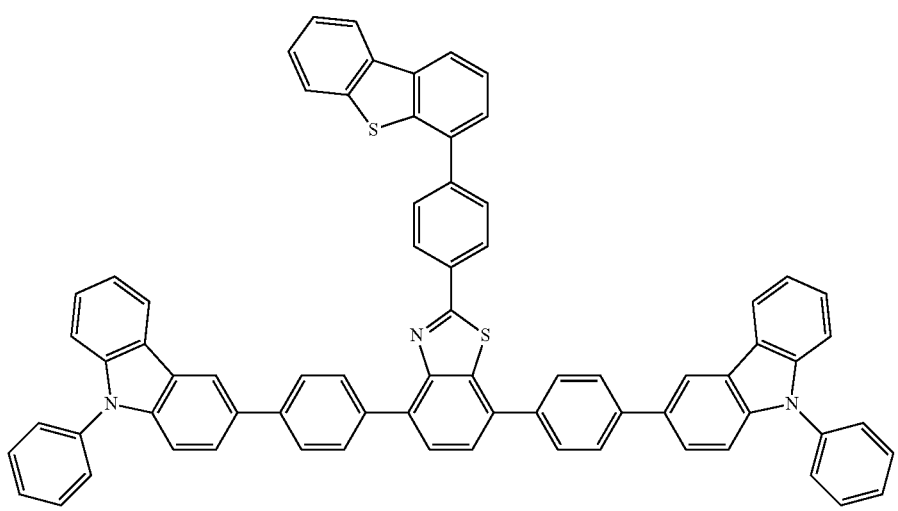
<Compound 8-50>
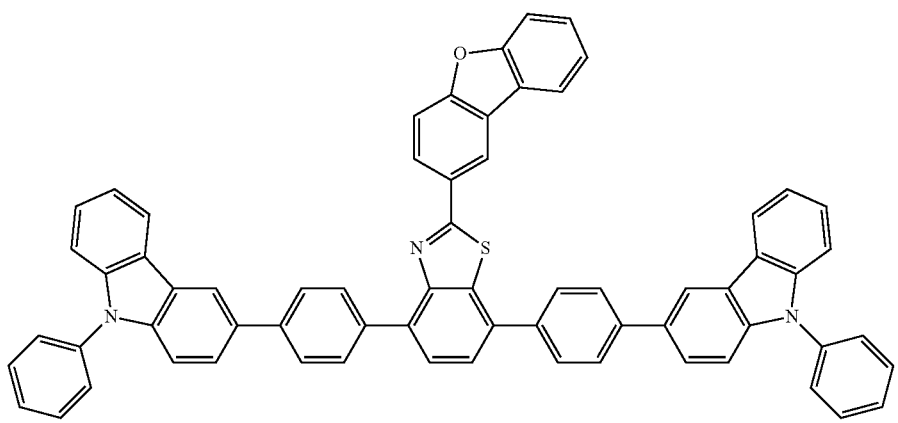
<Compound 8-51>
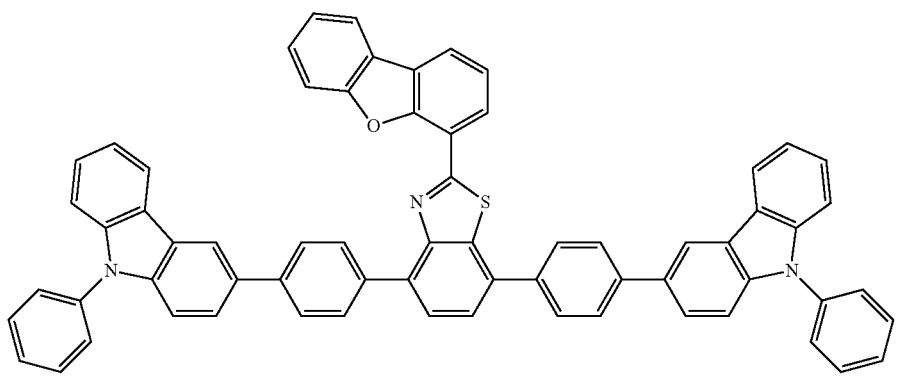

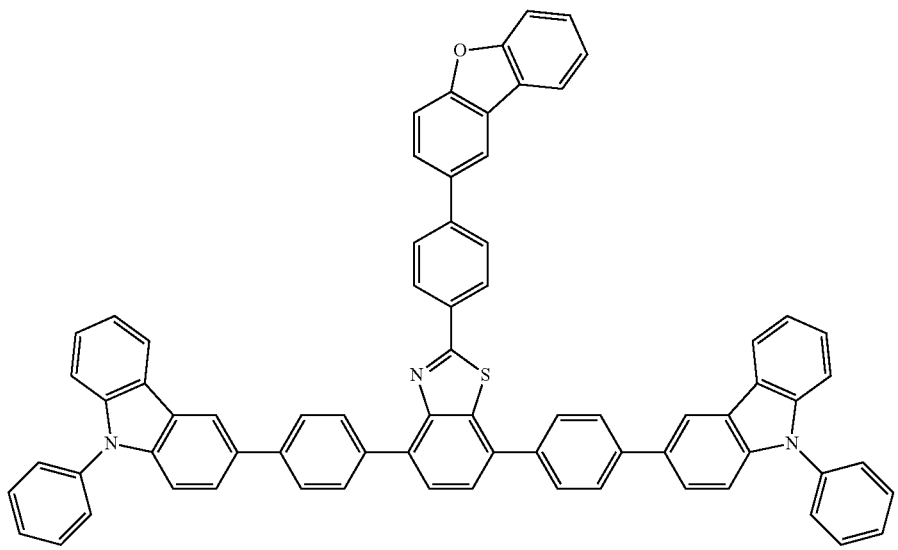
<Compound 8-52>
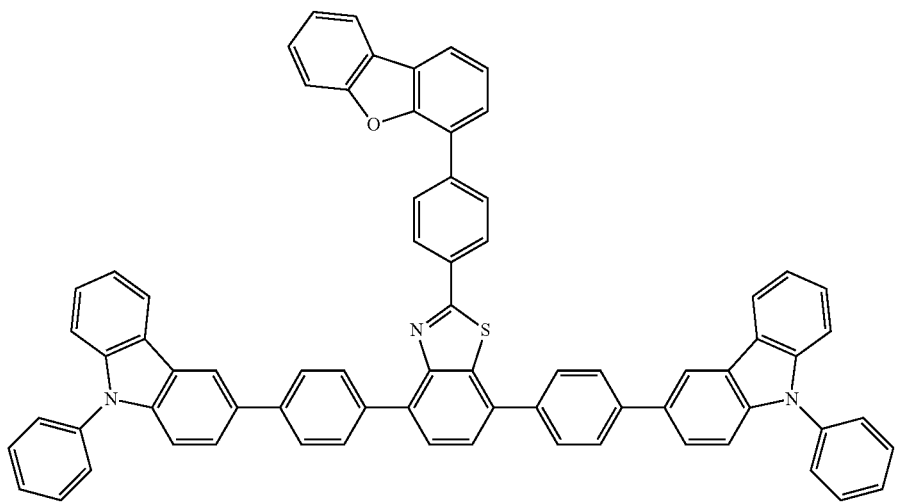
<Compound 8-53>
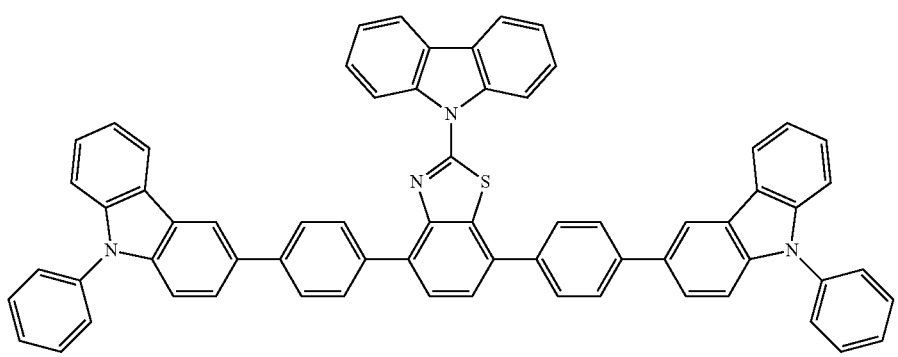
<Compound 8-54>

-continued
<Compound 8-55>
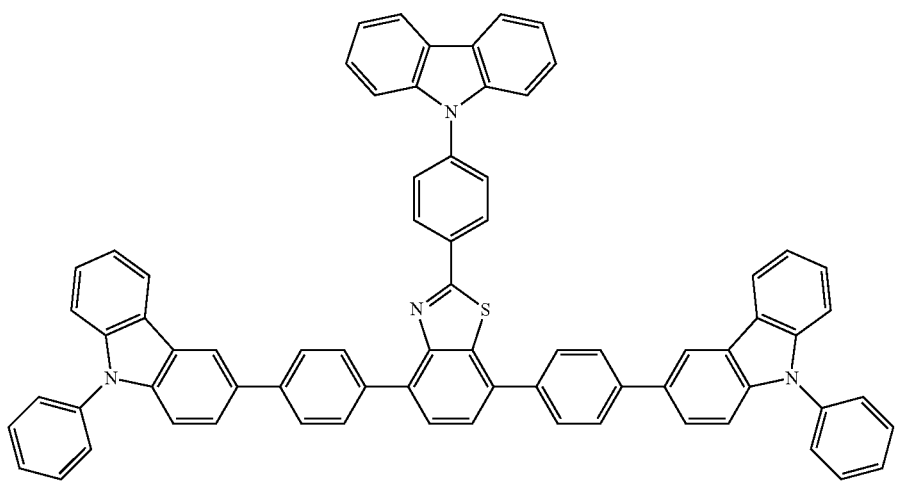
<Compound 8-56>
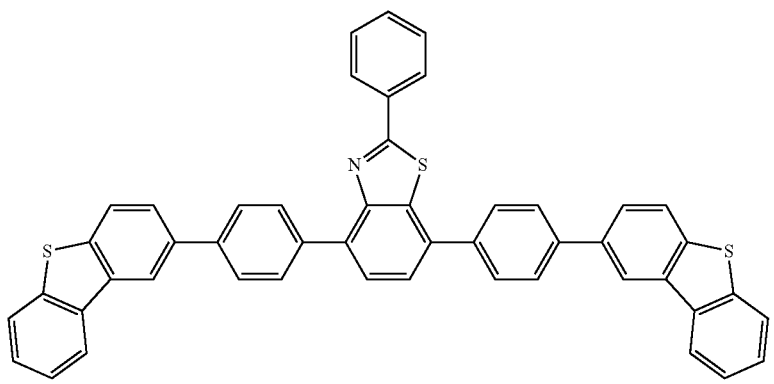
<Compound 8-57>
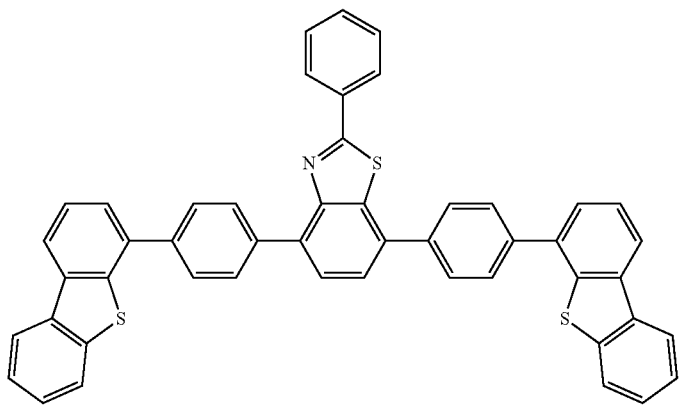
<Compound 8-58>
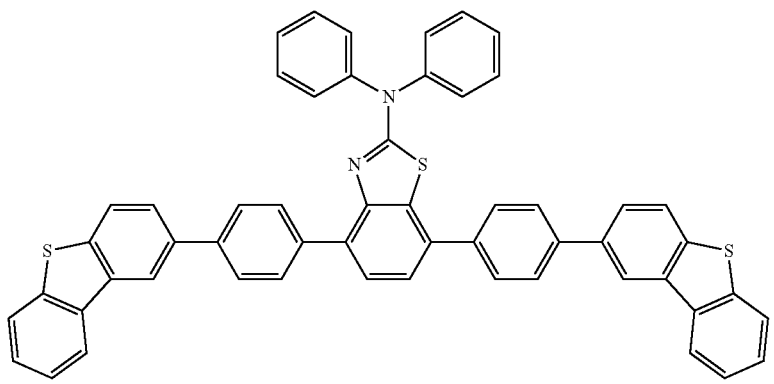

<Compound 8-59>
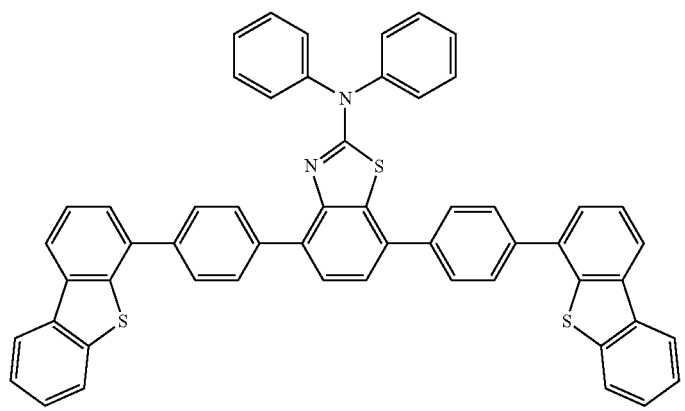
<Compound 8-60>
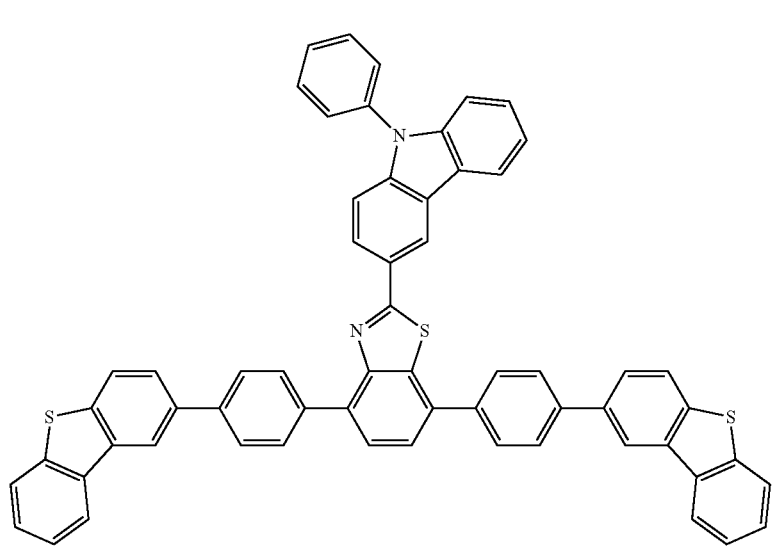
<Compound 8-61>
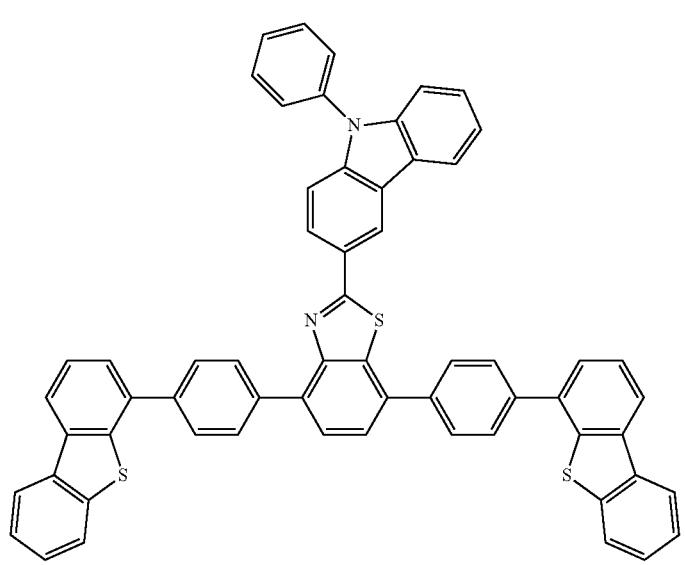

<Compound 8-62>
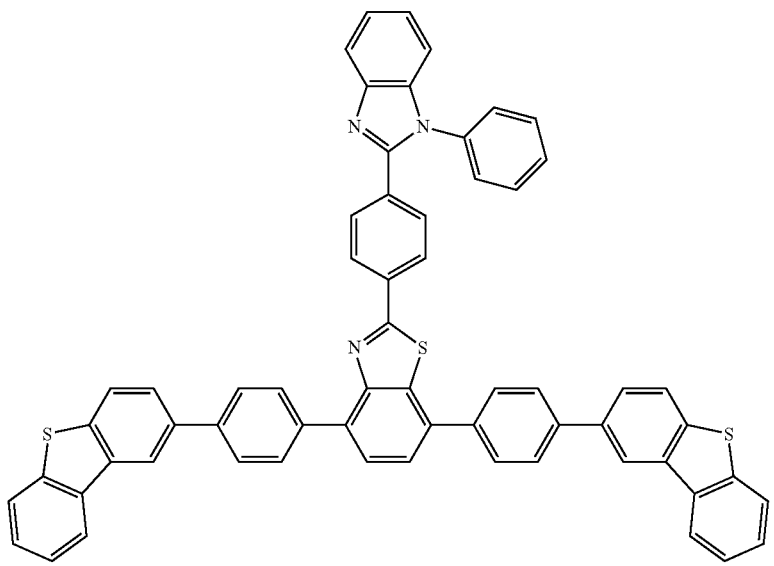
<Compound 8-63>
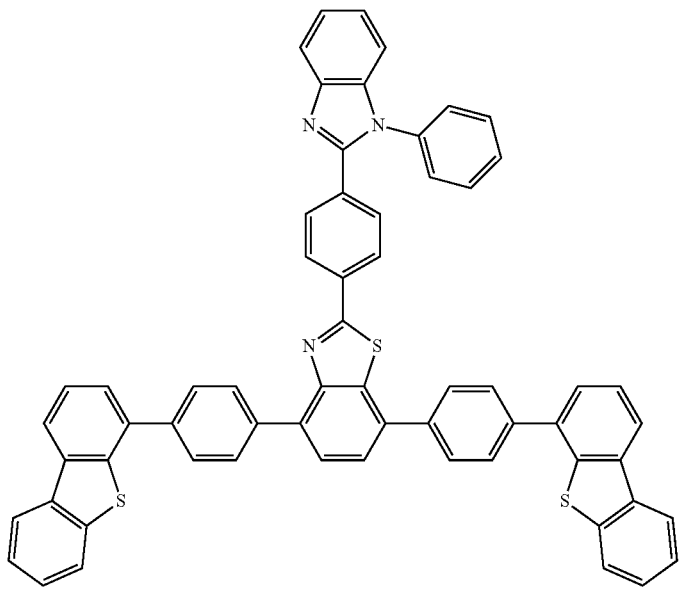
<Compound 8-64>
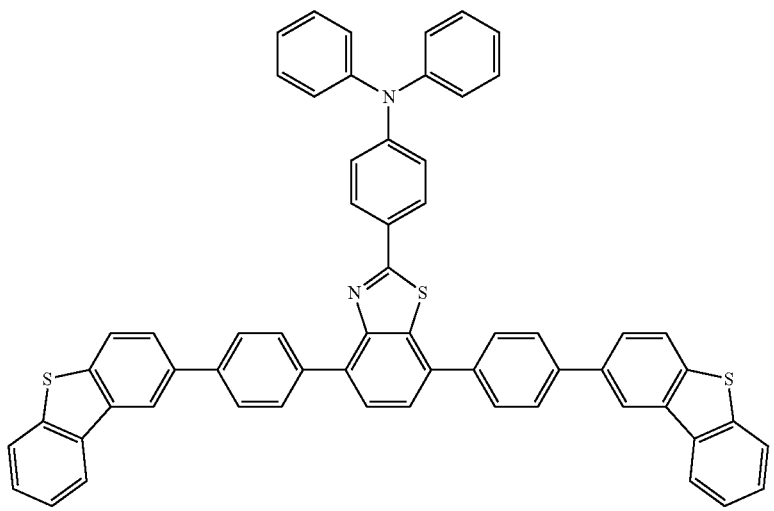

<Compound 8-65>
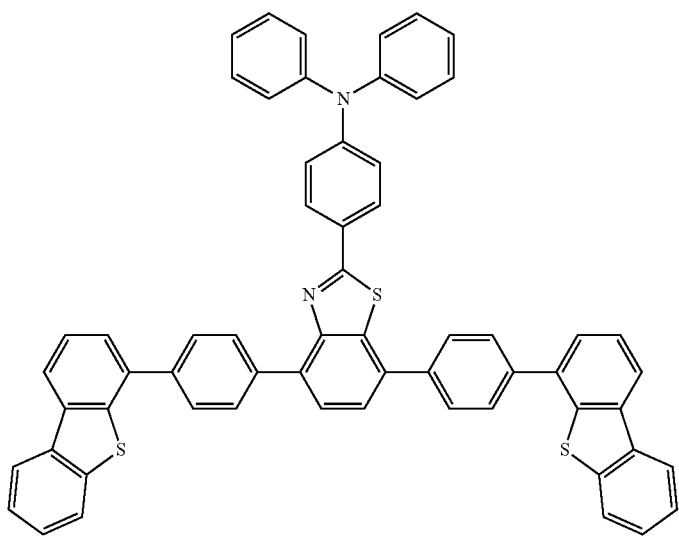
<Compound 8-66>
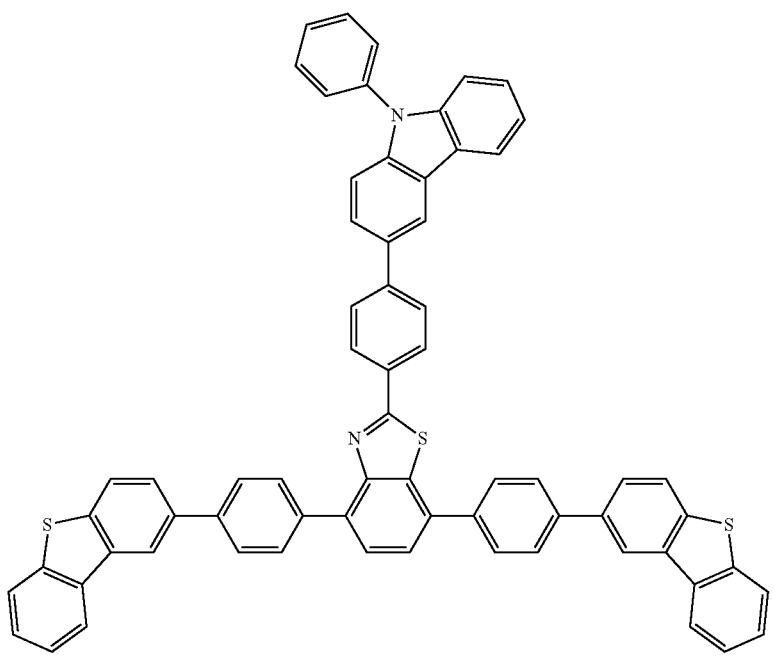

<Compound 8-67>
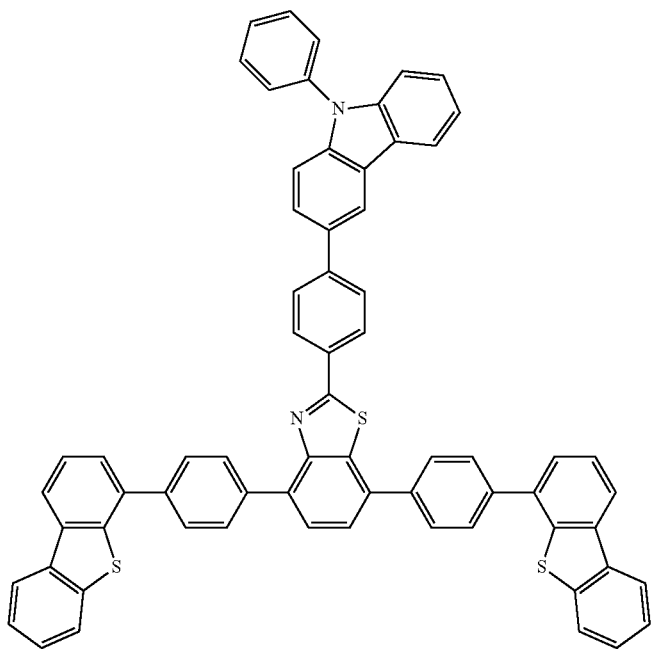
<Compound 8-68>
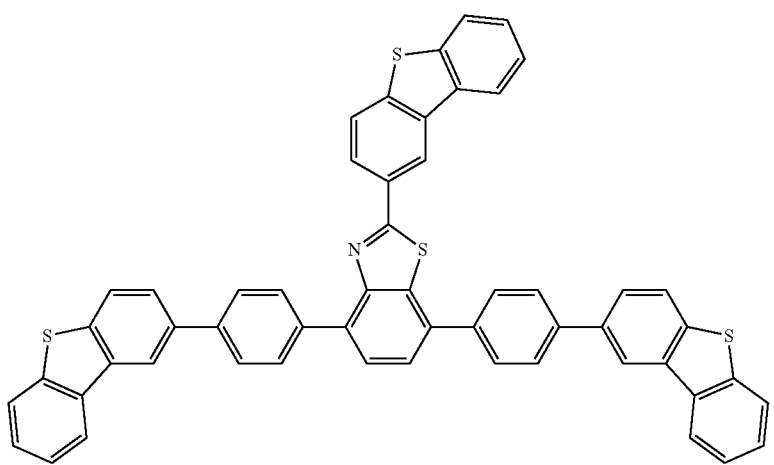
<Compound 8-69>
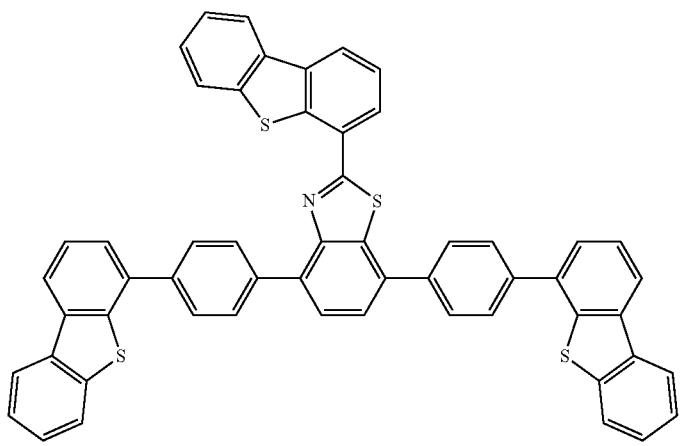

<Compound 8-70>
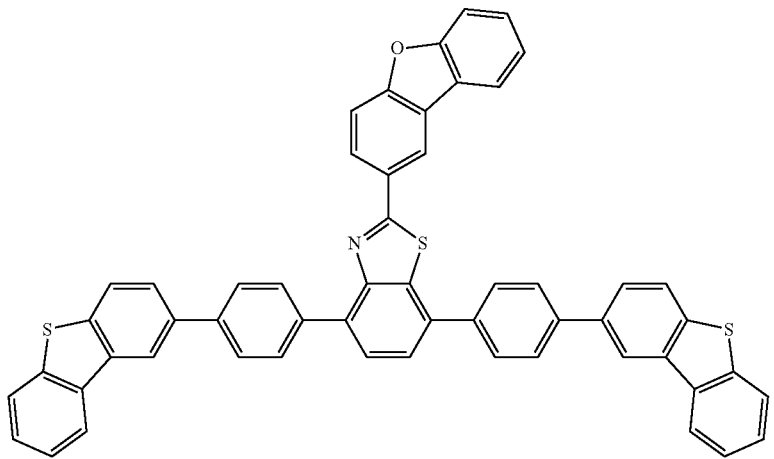
<Compound 8-71>
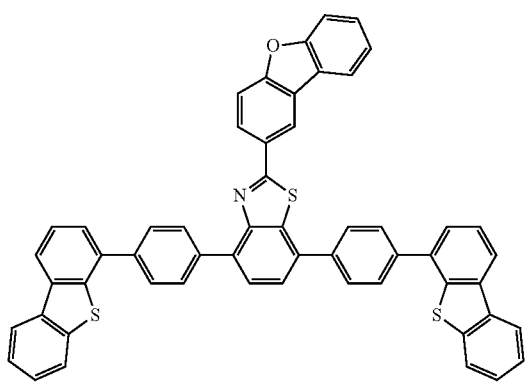
<Compound 8-72>
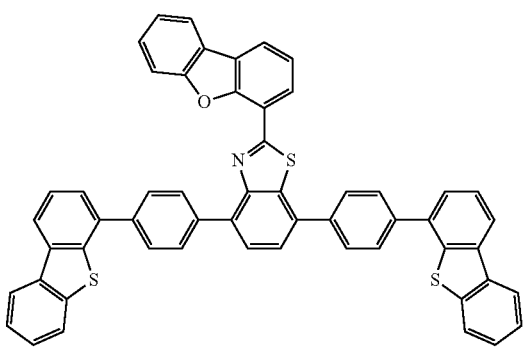
<Compound 8-73>
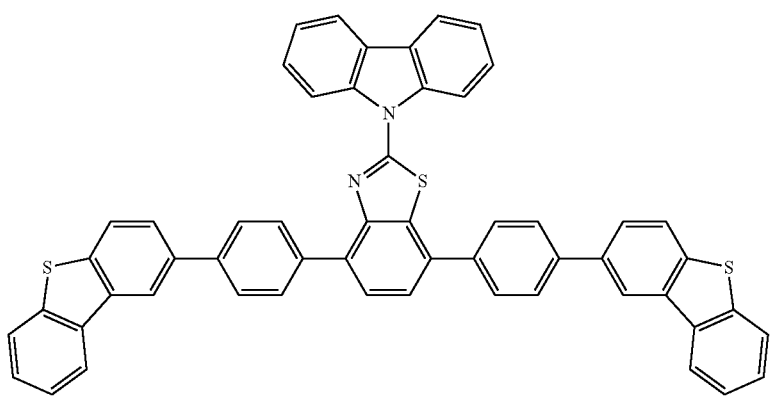

<Compound 8-74>
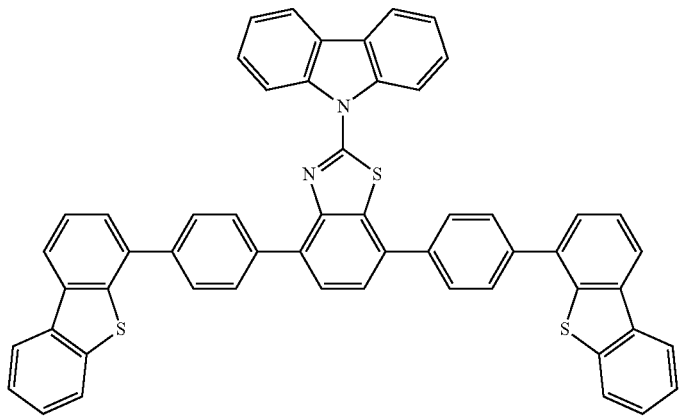
<Compound 8-75>
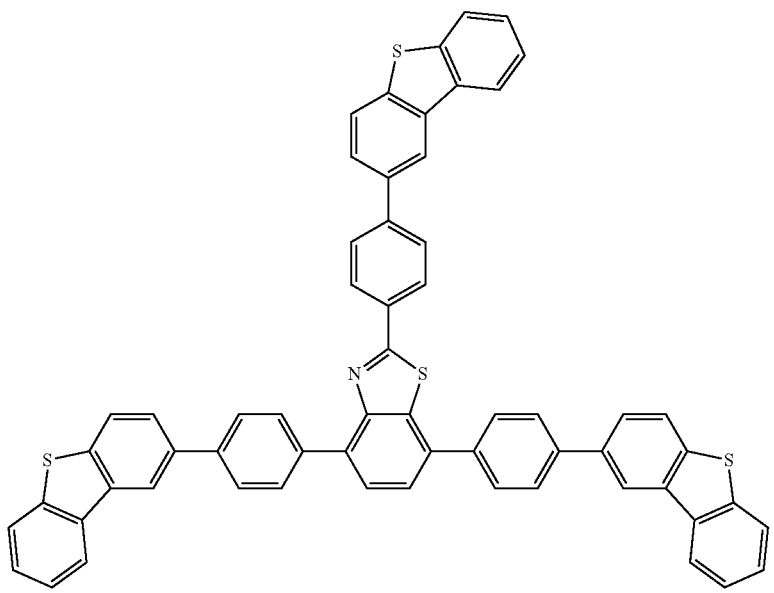
<Compound 8-76>
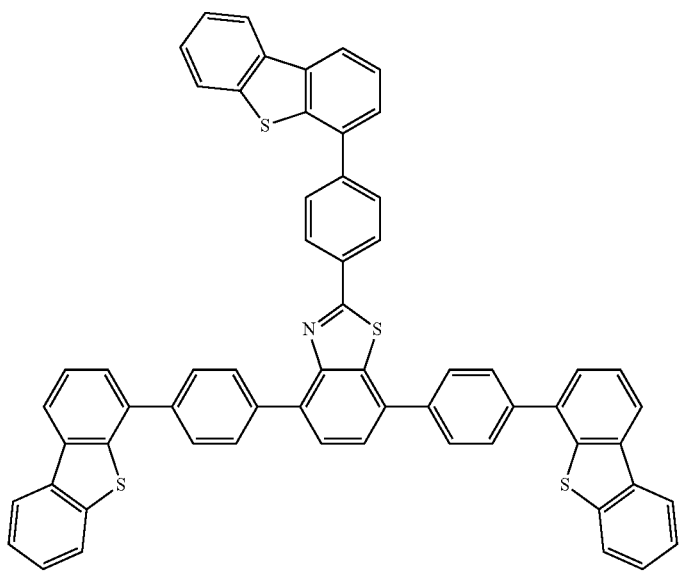

<Compound 8-77>
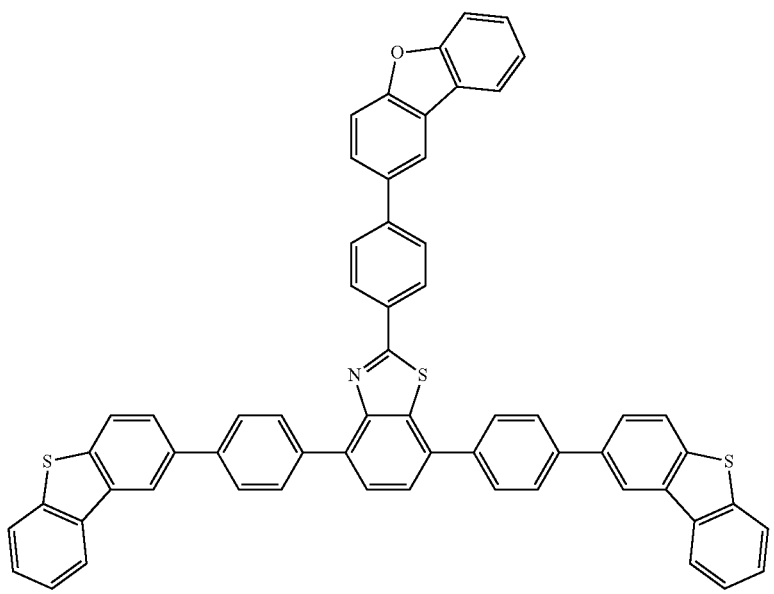
<Compound 8-78>
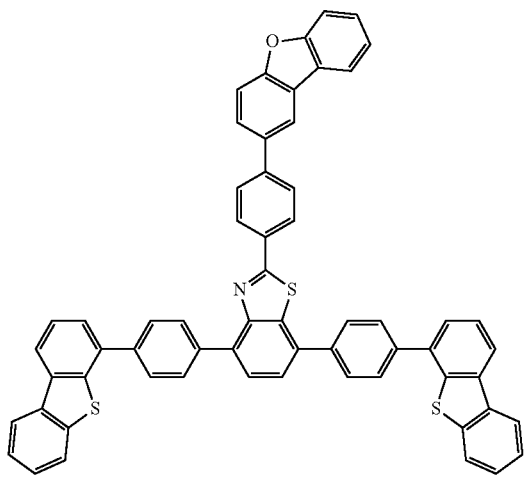
<Compound 8-79>
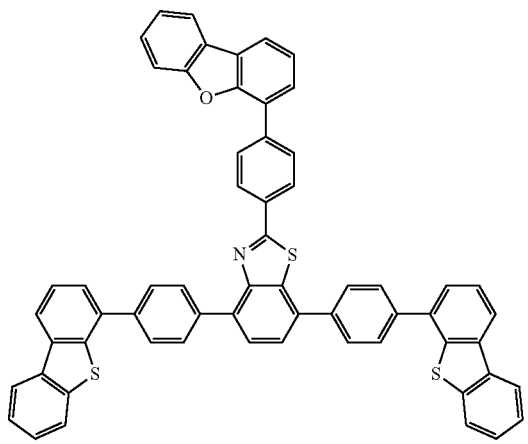
<Compound 8-80>
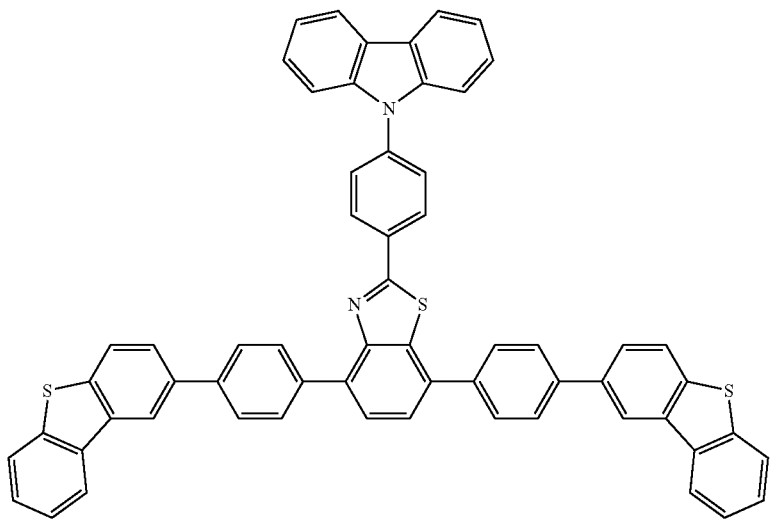

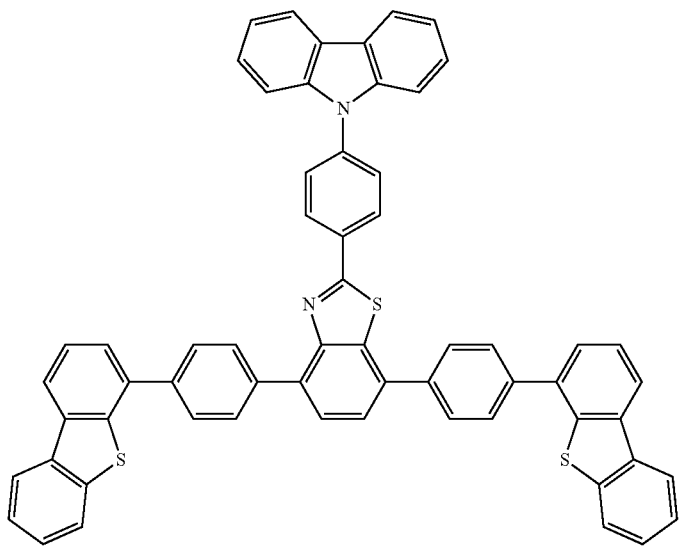
<Compound 8-81>
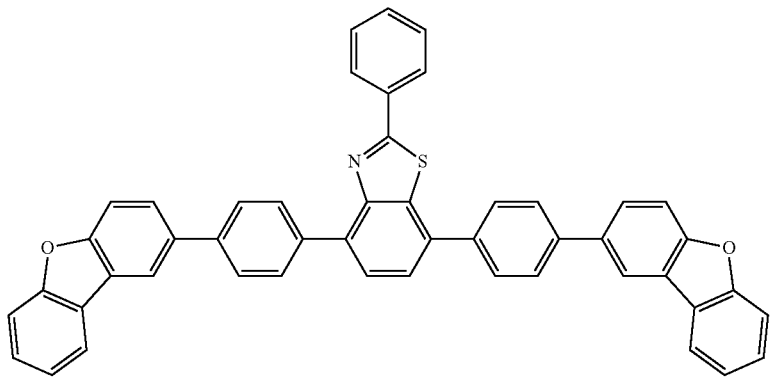
<Compound 8-82>
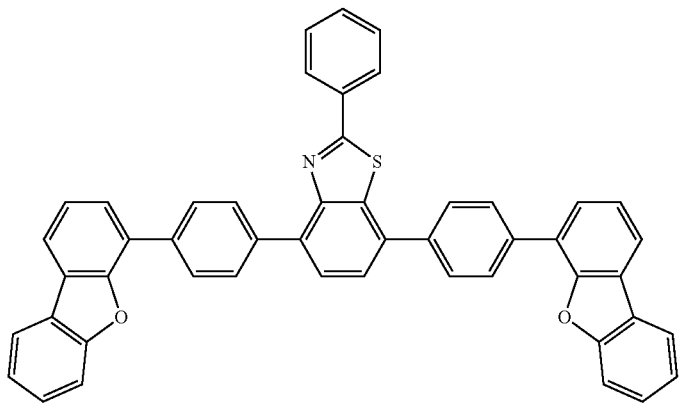
<Compound 8-83>

<Compound 8-84>
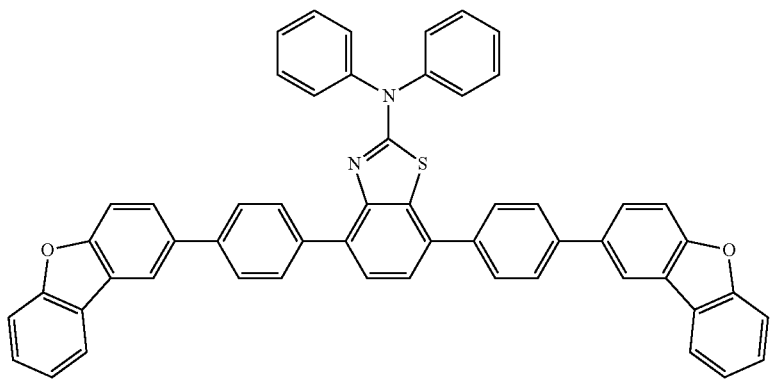
<Compound 8-85>
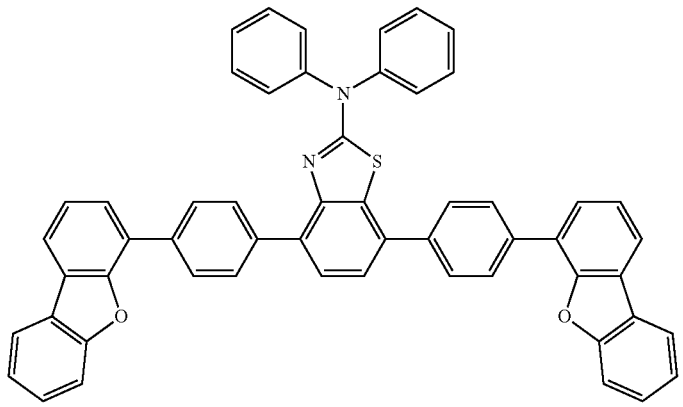
<Compound 8-86>
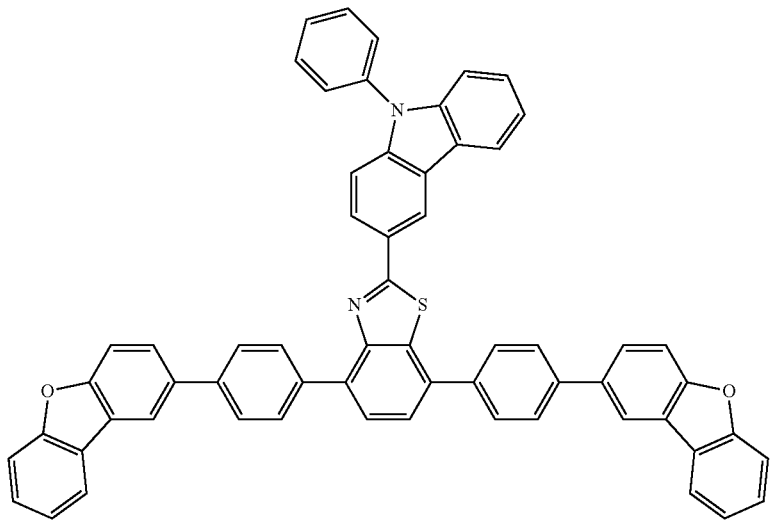

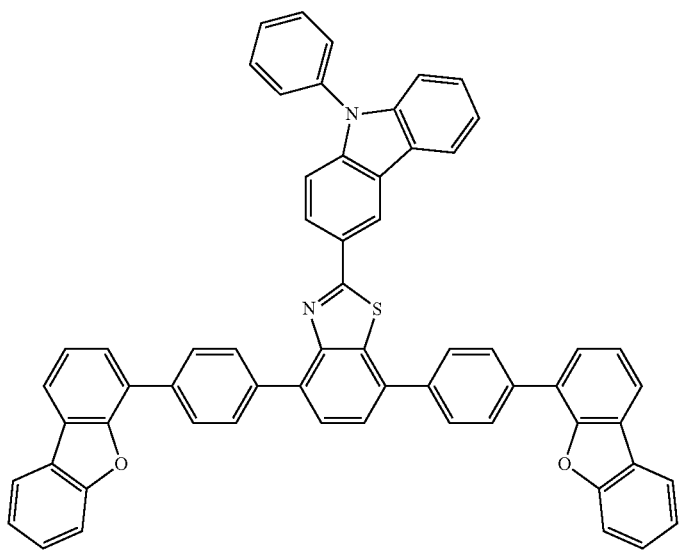
<Compound 8-87>
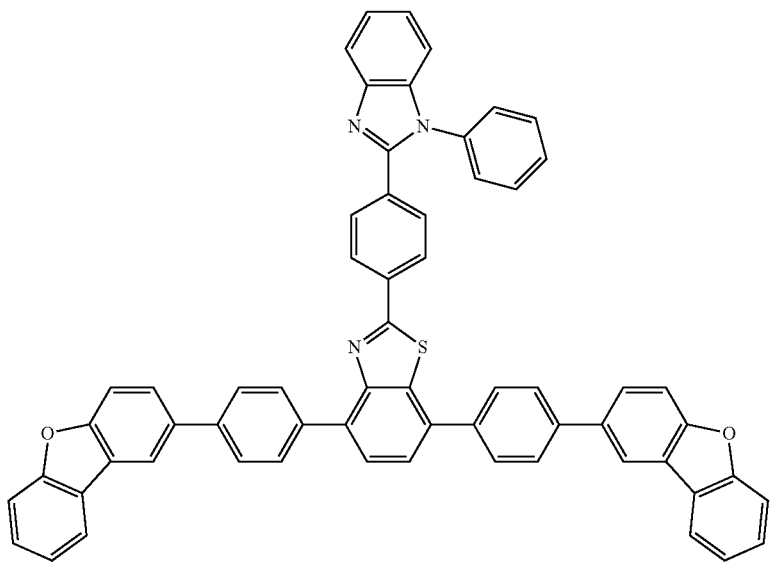
<Compound 8-88>

<Compound 8-89>
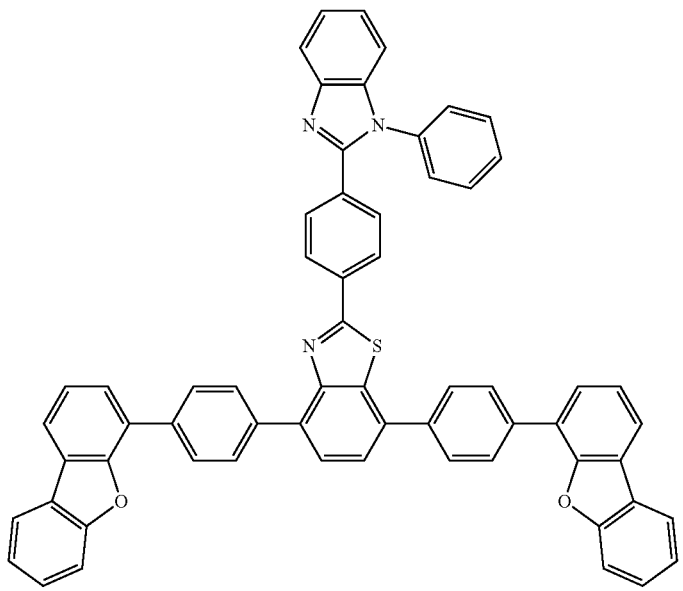
<Compound 8-90>
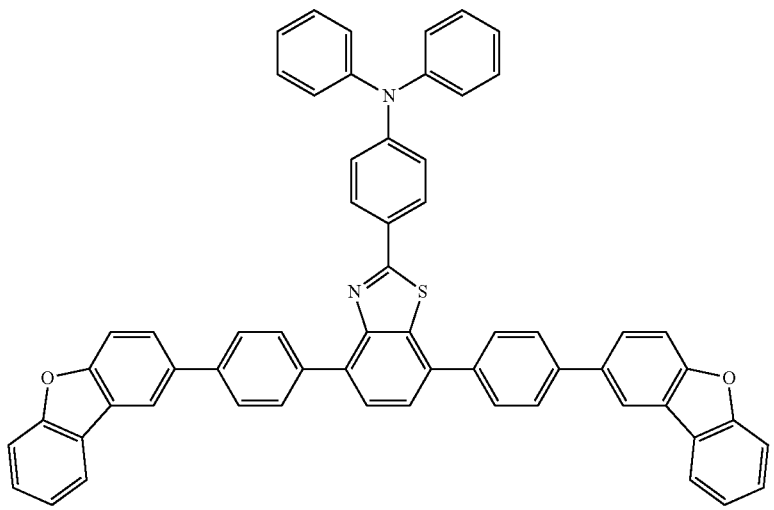
<Compound 8-91>
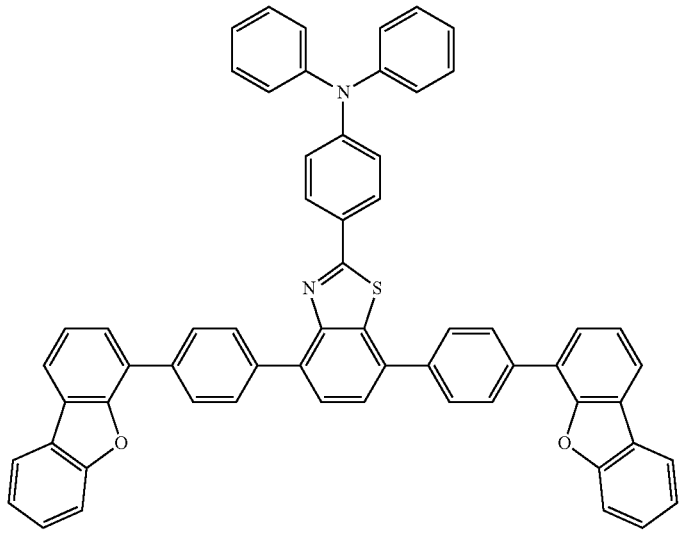

-continued
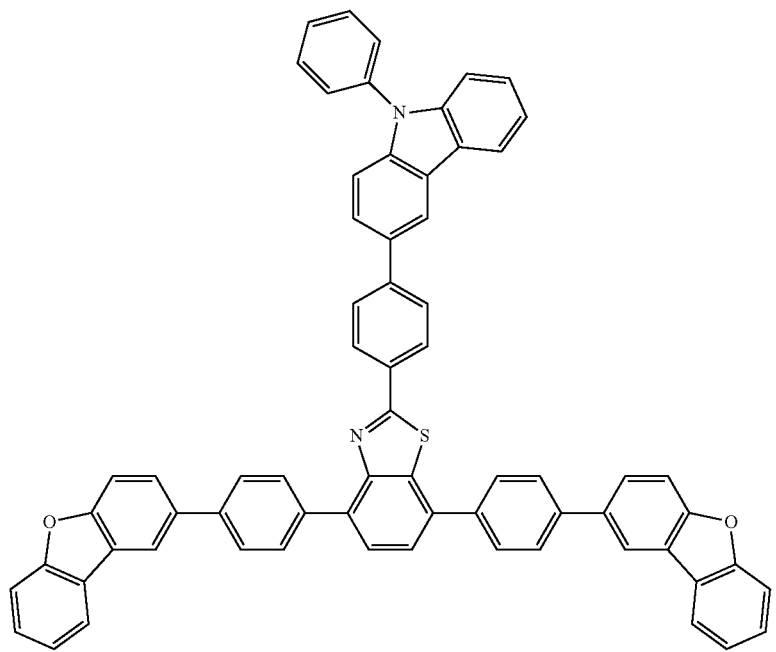
<Compound 8-92>
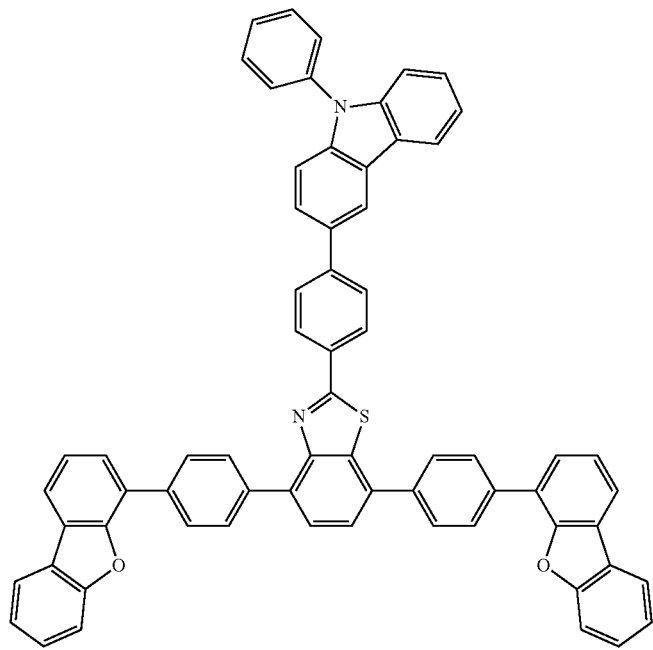
<Compound 8-93>

<Compound 8-94>
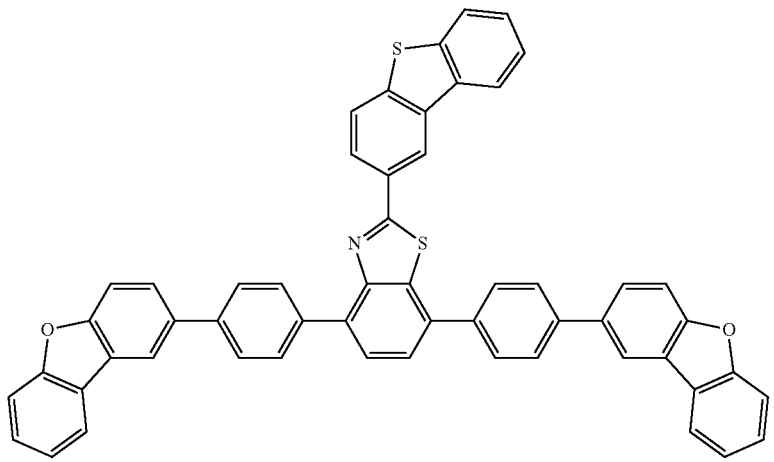
<Compound 8-95>
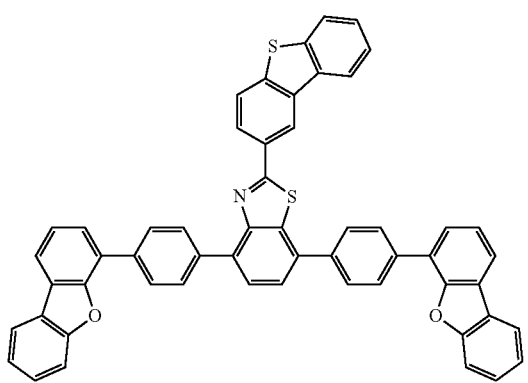
<Compound 8-96>
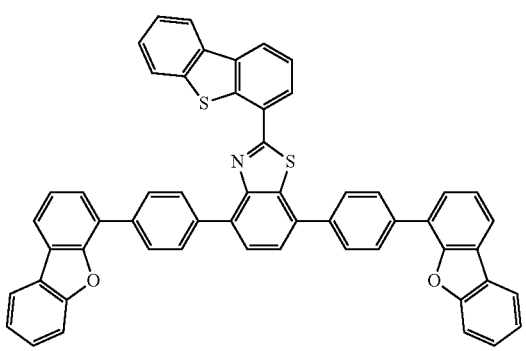
<Compound 8-97>
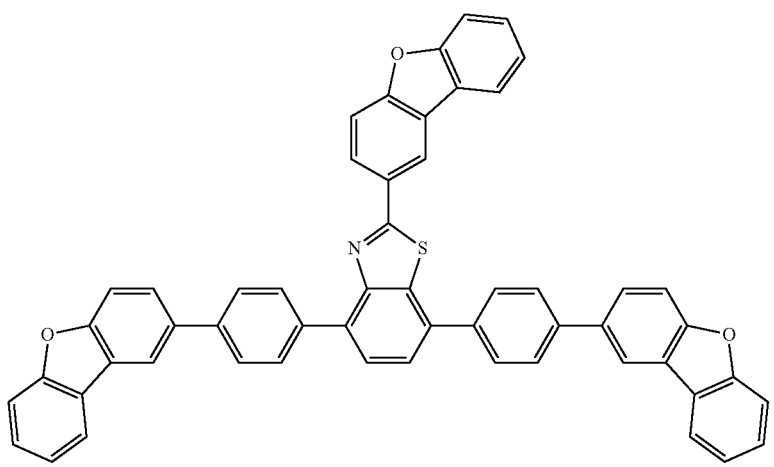

<Compound 8-98>
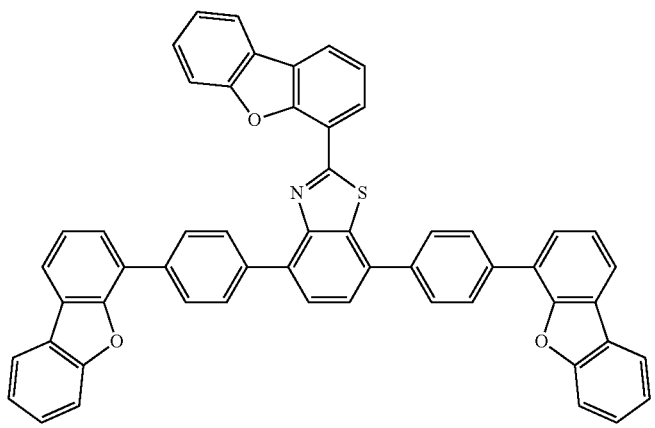
<Compound 8-99>
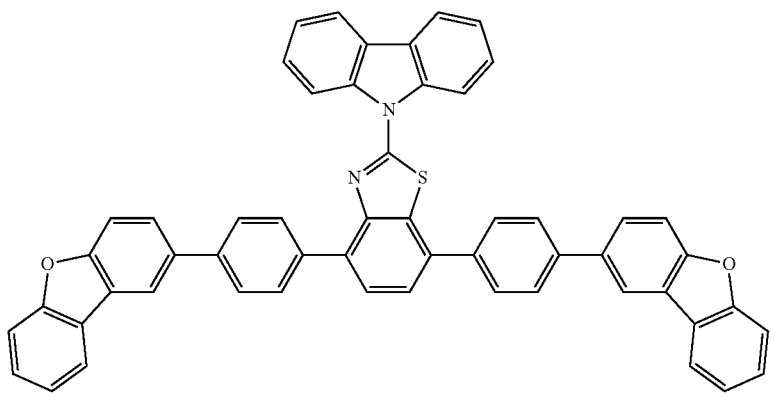
<Compound 8-100>
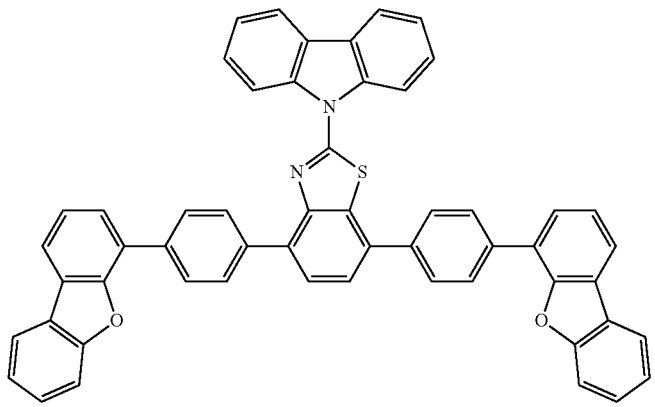

-continued
<Compound 8-101>
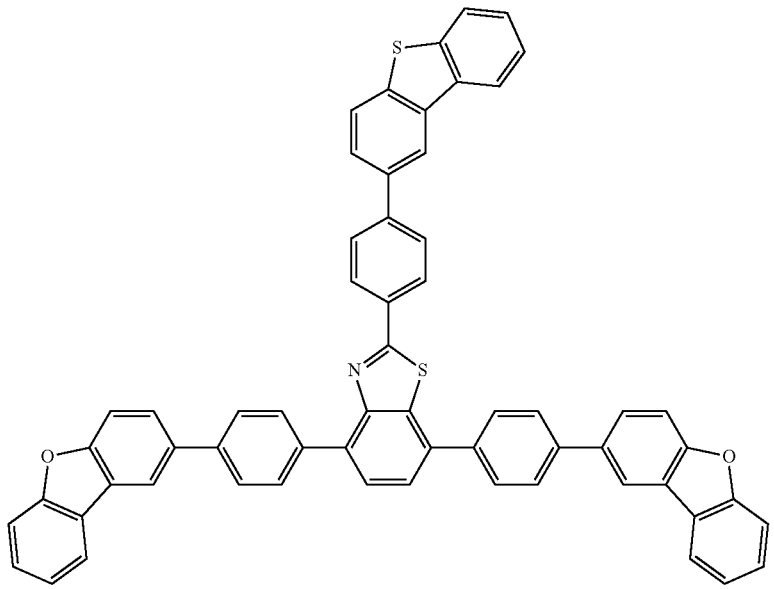
<Compound 8-102>
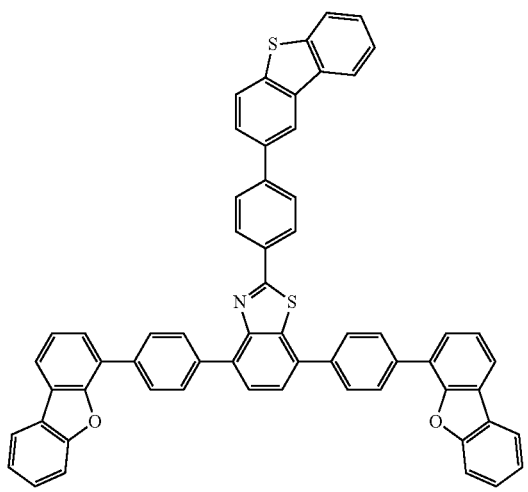
<Compound 8-103>
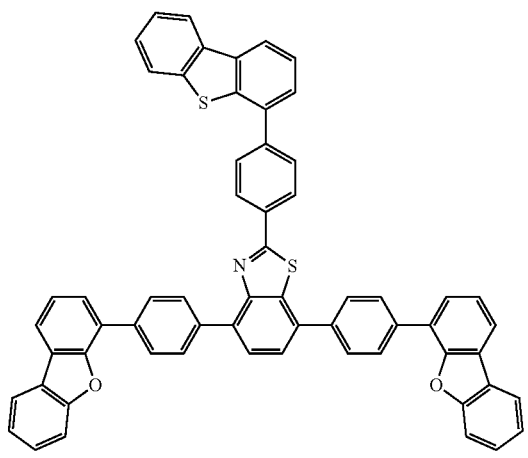

<Compound 8-104>
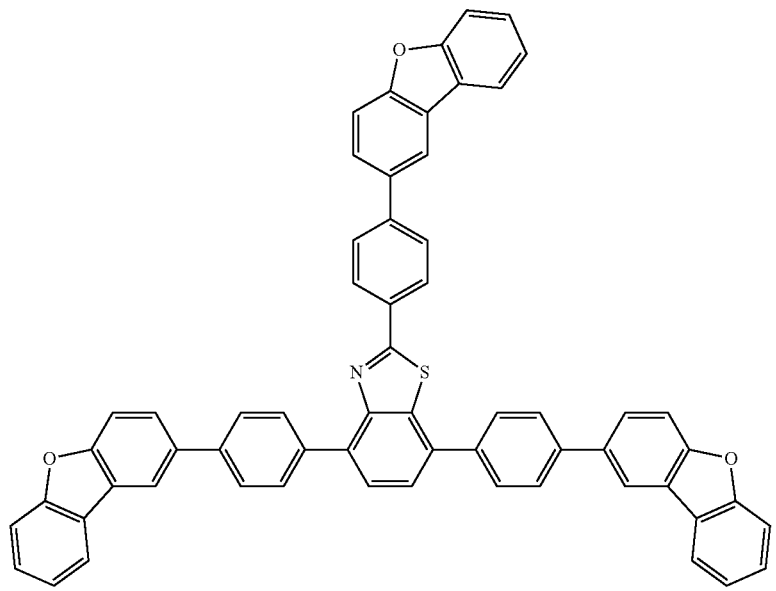
<Compound 8-105>
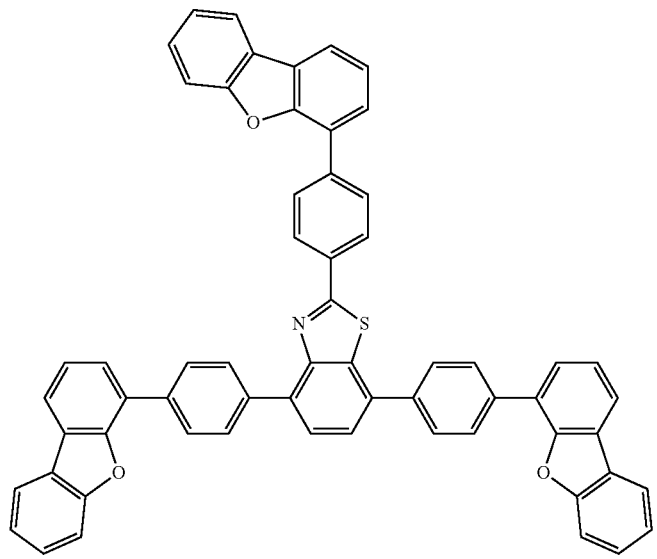
<Compound 8-106>
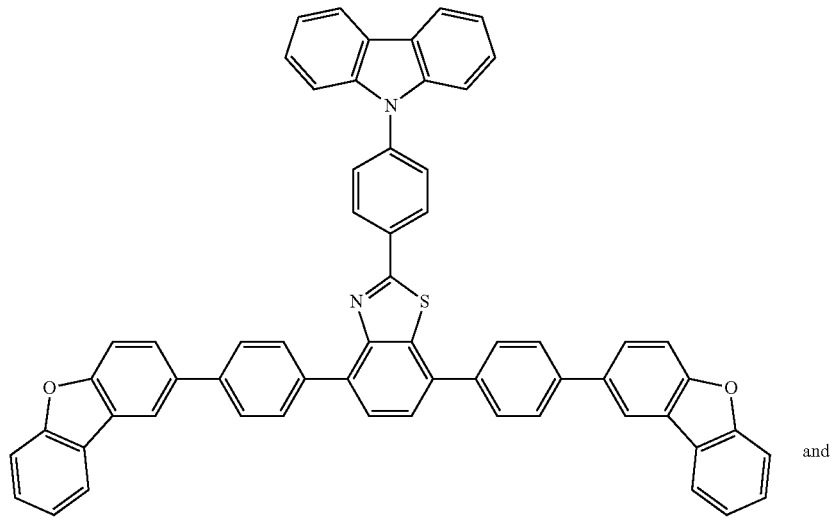
and

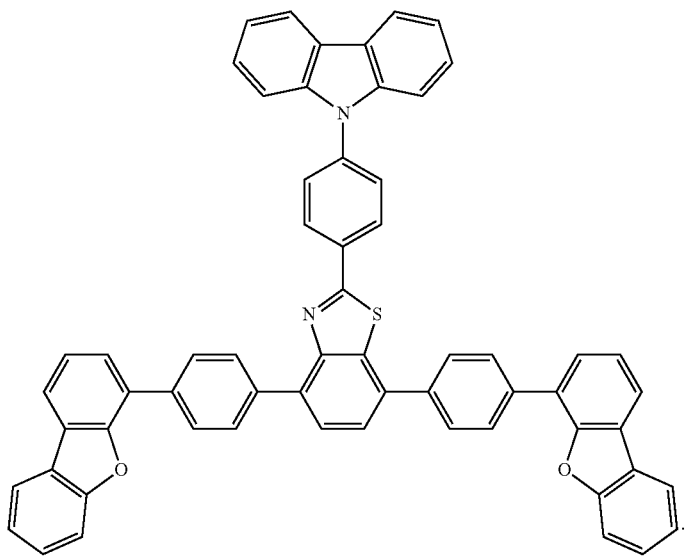

<Compound 8-107>

4. A light-emitting element comprising a compound represented by Formula 1 of claim 1.

5. The light-emitting element of claim 4, wherein the light-emitting element comprises:
a first electrode;
a second electrode;
a light-emitting layer disposed between the first electrode and the second electrode; and
a hole transporting layer disposed between the first electrode and the light-emitting layer, wherein the hole transporting layer comprises the compound represented by Formula 1.

6. The light-emitting element of claim 5, wherein the hole transporting layer further comprises a P-type dopant.

7. The light-emitting element of claim 5, wherein the hole transporting layer comprises a first layer that comprises the compound represented by Formula 1.

8. The light-emitting element of claim 4, wherein the light-emitting element comprises:
a first electrode;
a second electrode;
a light-emitting layer disposed between the first electrode and the second electrode; and
an electron transporting layer disposed between the second electrode and the light-emitting layer, wherein the electron transporting layer comprises the compound represented by Formula 1.

9. The light-emitting element of claim 8, wherein the electron transporting layer further comprises an N-type dopant.

10. The light-emitting element of claim 8, wherein the electron transporting layer comprises a first layer that comprises the compound represented by Formula 1.

11. The light-emitting element of claim 4, wherein the light-emitting element comprises:
a first electrode;
a second electrode; and
a light-emitting layer disposed between the first electrode and the second electrode, wherein the light-emitting layer comprises the compound represented by Formula 1.

12. The light-emitting element of claim 11, wherein the light-emitting layer further comprises a dopant.

13. An electronic device comprising the light-emitting element of claim 4.

14. The electronic device of claim 13, wherein the electronic device is a display device or a lighting device.

* * * * *